(12) United States Patent
Schwink et al.

(10) Patent No.: US 8,501,771 B2
(45) Date of Patent: Aug. 6, 2013

(54) AMINOALCOHOL-SUBSTITUTED ARYLDIHYDROISOQUINOLINONES, PROCESS FOR THEIR PREPARATION AND THEIR USE AS MEDICAMENTS

(75) Inventors: Lothar Schwink, Frankfurt am Main (DE); Siegfried Stengelin, Frankfurt am Main (DE); Matthias Gossel, Frankfurt am Main (DE); Gerhard Hessler, Frankfurt am Main (DE); Torsten Haack, Frankfurt am Main (DE); Petra Lennig, Frankfurt am Main (DE)

(73) Assignee: Sanofi, Paris (FR)

( * ) Notice: Subject to any disclaimer, the term of this patent is extended or adjusted under 35 U.S.C. 154(b) by 1143 days.

(21) Appl. No.: 12/191,697

(22) Filed: Aug. 14, 2008

(65) Prior Publication Data
US 2009/0082391 A1   Mar. 26, 2009

Related U.S. Application Data

(63) Continuation of application No. PCT/EP2007/001214, filed on Feb. 13, 2007.

(30) Foreign Application Priority Data

Feb. 15, 2006   (DE) .......................... 10 2006 007 048

(51) Int. Cl.
*A01N 43/42*   (2006.01)
*A61K 31/47*   (2006.01)
*C07D 217/22*  (2006.01)

(52) U.S. Cl.
USPC .......................................... 514/309; 546/141

(58) Field of Classification Search
USPC .......................................... 514/309; 546/141
See application file for complete search history.

(56) References Cited

U.S. PATENT DOCUMENTS

2005/0182045 A1* 8/2005 Nagase et al. ........... 514/217.06

FOREIGN PATENT DOCUMENTS

| | | |
|---|---|---|
| JP | 10-259176 | 9/1998 |
| WO | WO 01/21577 A2 | 3/2001 |
| WO | WO 01/72712 A1 | 10/2001 |
| WO | WO 02/02744 A2 | 1/2002 |
| WO | WO 02/06245 A1 | 1/2002 |
| WO | WO 02/10146 A1 | 2/2002 |
| WO | WO 02/057233 A1 | 7/2002 |
| WO | WO 02/089729 A2 | 11/2002 |
| WO | WO 03/033476 A1 | 4/2003 |
| WO | WO 03/033480 A1 | 4/2003 |
| WO | WO 03/035624 A1 | 5/2003 |
| WO | WO 03/045313 A2 | 6/2003 |
| WO | WO 03/097047 A1 | 11/2003 |
| WO | WO 2004/024702 A1 | 3/2004 |
| WO | WO 2004/092181 | 10/2004 |
| WO | WO 2005/021533 A1 | 3/2005 |
| WO | WO 2005/042541 | 5/2005 |
| WO | WO 2005/047293 A1 | 5/2005 |
| WO | WO 2005/103039 A1 | 11/2005 |

* cited by examiner

*Primary Examiner* — Kendra D Carter
(74) *Attorney, Agent, or Firm* — Scully, Scott, Murphy & Presser, P.C.

(57) ABSTRACT

The invention relates to aminoalcohol-substituted aryldihydroisoquinolinones and their derivatives, and their physiologically tolerated salts and physiologically functional derivatives, their preparation, medicaments comprising at least one aminoalcohol-substituted aryldihydroisoquinolinone of the invention or its derivative, and the use of the aminoalcohol-substituted aryldihydroisoquinolinones of the invention and their derivatives as MCH antagonists.

36 Claims, No Drawings

AMINOALCOHOL-SUBSTITUTED ARYLDIHYDROISOQUINOLINONES, PROCESS FOR THEIR PREPARATION AND THEIR USE AS MEDICAMENTS

This application is a Continuation of International Application No. PCT/EP2007/001214, filed Feb. 13, 2007, which is incorporated herein by reference in its entirety.

FIELD OF THE INVENTION

The invention relates to aminoalcohol-substituted aryldihydroisoquinolinones and their derivatives, and their physiologically tolerated salts and physiologically functional derivatives, their preparation, medicaments comprising at least one aminoalcohol-substituted aryldihydroisoquinolinone of the invention or its derivative, and the use of the aminoalcohol-substituted aryldihydroisoquinolinones of the invention and their derivatives as medicaments.

BACKGROUND OF THE INVENTION

Compounds similar in their overall structure to the aminoalcohol-substituted aryl-dihydroisoquinolinones and their derivatives described in the present application and having a pharmacological effect have been described in the prior art. Thus, for example, WO 01/72712 describes inhibitors of factor Xa which have a substituted isoquinolinone basic structure. WO 2005/021533 relates to substituted isoquinolinone derivatives which are employed for the treatment of cancer. US 2005/0182045 discloses 4-oxopyrimidine derivatives having a fused ring. The 4-oxopyrimidine derivatives are active as histamine H3 receptor antagonists or have an inverse antagonistic activity. JP 102 59176 A relates to amide derivatives which are suitable as vascularization inhibitors.

Compounds having an MCH-antagonistic effect for the treatment of obesity are described in the prior art (examples: WO2005047293, WO2004092181, WO2005103039, WO2004024702, WO2005042541, WO2003033476, WO2003033480, WO2001021577, WO2003035624, WO2002089729, WO2002006245, WO2002002744, WO2002057233, WO2003045313, WO2003097047, WO2002010146, WO 2003087044).

The invention was based on the object of providing compounds which bring about a weight reduction in mammals and which are suitable for the prevention and treatment of obesity and diabetes and of their diverse sequelae.

Surprisingly, a series of compounds which modulate the activity of MCH receptors has been found. In particular, the compounds are notable for an antagonism of the MCH1R.

SUMMARY OF THE INVENTION

The invention therefore relates to compounds of the formula I,

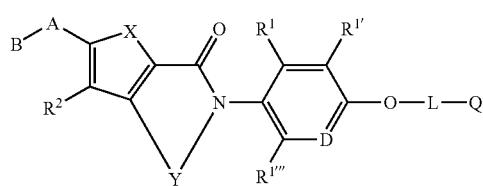

(I)

in which the meanings are
D N, C(R1"); preferably C(R1"):
R1, R1', R1", R1'"
  independently of one another H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R3)(R4), $SO_2$—$CH_3$, COOH, COO—($C_1$-$C_6$)-alkyl, CON(R5)(R6), N(R7)CO(R8), N(R9)$SO_2$(R10), CO(R11), (C(R12)(R13))$_x$-O(R14);
  preferably H, F, Cl, Br, OH, $CF_3$, $NO_2$, CN, $OCF_3$, O—($C_1$-$C_6$)-alkyl, ($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_2$-$C_6$)-alkynyl, O—($C_0$-$C_8$)-alkylene-aryl, CO($C_1$-$C_6$)-alkyl;
  particularly preferably H, F, Cl, Br, $CF_3$, CN, $OCF_3$, O—($C_1$-$C_6$)-alkyl, ($C_1$-$C_4$)-alkoxy-($C_1$-$C_4$)-alkyl, ($C_1$-$C_6$)-alkyl;
  very particularly preferably H, F, Cl, O—($C_1$-$C_6$)-alkyl, ($C_1$-$C_6$)-alkyl;
  where preferably at least two, particularly preferably at least three or all radicals R1, R1', R1" and R1'" are H;
R3, R4, R5, R6, R7, R9
  independently of one another H, ($C_1$-$C_8$)-alkyl;
or
R3 and R4, R5 and R6
  form independently of one another optionally together with the nitrogen atom to which they are bonded a 5-6 membered ring which, apart from the nitrogen atom, may also comprise 0-1 further heteroatoms from the group of NH, N—($C_1$-$C_6$)-alkyl, oxygen and sulfur;
R8, R10, R11
  independently of one another H, ($C_1$-$C_8$)-alkyl, aryl; preferably independently of one another H, ($C_1$-$C_8$)-alkyl;
R12, R13
  independently of one another H, ($C_1$-$C_8$)-alkyl; preferably independently of one another H;
R14 H, ($C_1$-$C_6$)-alkyl, aryl; preferably H, ($C_1$-$C_6$)-alkyl;
x 0, 1, 2, 3, 4, 5, 6;
R2 H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R15)(R16), $SO_2$—$CH_3$, COOH, COO—($C_1$-$C_6$)-alkyl, CON(R17)(R18), N(R19)CO(R20), N(R21)$SO_2$(R22), CO(R23), (C(R24)(R25))$_x$-O(R26);
  preferably H, F, Cl, Br, I, OH, $CF_3$, $NO_2$, CN, $OCF_3$, O—($C_1$-$C_6$)-alkyl, ($C_1$-$C_4$)-alkoxy($C_1$-$C_4$)-alkyl, ($C_1$-$C_6$)-alkyl, ($C_2$-$C_6$)-alkenyl, ($C_2$-$C_6$)-alkynyl;
  particularly preferably H, F, Cl, Br, $CF_3$, CN, $OCF_3$, O—($C_1$-$C_6$)-alkyl, ($C_1$-$C_4$)-alkoxy($C_1$-$C_4$)-alkyl, ($C_1$-$C_6$)-alkyl;
  very particularly preferably H, F, Cl, O—($C_1$-$C_6$)-alkyl, ($C_1$-$C_6$)-alkyl;
  in particular very particularly preferably H;
R15, R16, R17, R18, R19, R21
  independently of one another H, ($C_1$-$C_8$)-alkyl;
or
R15 and R16, R17 and R18
  form independently of one another and optionally together with the nitrogen atom to which they are bonded a 5-6 membered ring which, apart from the nitrogen atom, may also comprise 0-1 further heteroatoms from the group of NH, N—($C_1$-$C_6$)-alkyl, oxygen and sulfur;

R20, R22, R23
  independently of one another H, $(C_1-C_8)$-alkyl, aryl; preferably independently of one another H, $(C_1-C_8)$-alkyl;
R24, R25
  independently of one another H, $(C_1-C_8)$-alkyl;
R26 H, $(C_1-C_6)$-alkyl, aryl; preferably H, $(C_1-C_6)$-alkyl;
x' 0, 1, 2, 3, 4, 5, 6;
Y C(R27)(R27')C(R28)(R28'), C(R29)=C(R29'); preferably C(R27)(R27')C(R28)(R28');
R27, R27', R28, R28', R29, R29'
  independently of one another H, $(C_1-C_8)$-alkyl; preferably H;
X S, O, C(R30)=C(R30'); preferably S, C(R30)=C(R30'); particularly preferably C(R30)=C(R30');
R30, R30'
  independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), (C(R24)(R25))$_{x'}$-O(R26);
  preferably H, F, Cl, Br, I, OH, $CF_3$, $NO_2$, CN, $OCF_3$, O—$(C_1-C_6)$-alkyl, $(C_1-C_4)$-alkoxy$(C_1-C_4)$-alkyl, $(C_1-C_6)$-alkyl, $(C_2-C_6)$-alkenyl, $(C_2-C_6)$-alkynyl;
  particularly preferably H, F, Cl, Br, $CF_3$, CN, $OCF_3$, O—$(C_1-C_6)$-alkyl, $(C_1-C_4)$-alkoxy$(C_1-C_4)$-alkyl, $(C_1-C_6)$-alkyl;
  very particularly preferably H, F, Cl, O—$(C_1-C_6)$-alkyl, $(C_1-C_6)$-alkyl;
  in particular very particularly preferably H;
A a bond or a linker having 1 to 8 members, where the members are selected from the group consisting of O, S, $SO_2$, N(R31), CO, C(R32)(R33), C(R34)=C(R34'), cyclopropylene, C≡C, resulting in a chemically reasonable radical;
  preferably a bond or a linker having 1 to 6 members, where the members are selected from the group consisting of O, $SO_2$, N(R31), CO, C(R32)(R33), C(R34)=C(R34'), C≡C, resulting in a chemically reasonable radical;
  particularly preferably a bond or a linker having 1 to 5 members, where the members are selected from the group consisting of O, $SO_2$, N(R31), CO, C(R32)(R33), C≡C, resulting in a chemically reasonable radical;
  very particularly preferably a bond or a linker having 1 to 5 members, where the members are selected from the group consisting of O, $SO_2$, N(R31), CO, C(R32)(R33), C≡C, resulting in a chemically reasonable radical, where the linker contains no O—CO or CO—O groups;
R31, R34, R34'
  independently of one another H, $(C_1-C_8)$-alkyl;
R32, R33
  independently of one another H, $(C_1-C_6)$-alkyl, OH, O—$(C_1-C_6)$-alkyl;
B H, N(R35)(R36), hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi-, tri- or spirocyclic ring which may comprise 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43), $SO_2CH_3$, $SCF_3$ or S—$(C_1-C_6)$-alkyl;
  preferably H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;
  particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;
  very particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl, N(R42)(R43) or $SO_2CH_3$;
R35, R36, R37, R38, R39, R40, R41, R42, R43
  independently of one another H, $(C_1-C_8)$-alkyl;
or
R38 and R39, R42 and R43
  form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur; where
L a bond, $(C_1-C_3)$-alkylene; preferably a bond, $CH_2$—$(CH_2)_2$, $(CH_2)_3$;
Q N(R53')(R54'), a bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, OXO, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R44), (C(R45)(R46))$_o$-R47, CO(C(R45)(R46))$_p$-R48;
  preferably a bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, OXO, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R44), (C(R45)(R46))$_o$-R47, CO(C(R45)(R46))$_p$-R48;
R44 H, $(C_1-C_8)$-alkyl;
R45, R46
  independently of one another H, $(C_1-C_8)$-alkyl, OH, $(C_3-C_8)$-cycloalkyl, $(C_1-C_4)$-alkoxy-$(C_1-C_4)$-alkyl; preferably H, $(C_1-C_6)$-alkyl; particularly preferably H;

o, p independently of one another 0, 1, 2, 3, 4, 5, 6; preferably 0, 1, 2, 3, 4;

R47, R48
independently of one another OH, F, O—$(C_1-C_8)$-alkyl, CON(R49)(R50), N(R51)CO(R52), N(R53)(R54), $CO_2$(R55), $SO_2$Me, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, $(C_1-C_4)$-alkoxy-$(C_1-C_4)$-alkyl, CO(R56), oxo, OH;

R49, R50, R51, R52, R55, R56
independently of one another H, $(C_1-C_8)$-alkyl;
or
R49 and R50
form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

R53, R54, R53', R54'
independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R57), $(C(R58)(R59))_q$-R60, CO(C(R61)(R62))$_r$-R63, CO—$(CH_2)_o$,, —O—$(C_1-C_6)$-alkyl; or R53 and R54 or R53' and R54' form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R64), oxo, OH, $(C_1-C_4)$-alkoxy-$(C_1-C_4)$-alkyl, hydroxy-$(C_1-C_4)$-alkyl, CON(R65)(R66), N(R67)CO(R68), N(R69)(R70), $CO_2$(R71), $SO_2(C_1-C_6)$-alkyl; R53, R53' are preferably:
independently of one another H, $(C_1-C_8)$-alkyl, $(C(R58)(R59))_q$-R60, $(C_1-C_4)$-alkoxy$(C_1-C_4)$-alkyl, $(C_3-C_8)$-alkenyl, $(C_3-C_8)$-alkynyl, CO—$(C_1-C_8)$-alkyl, CO—$(CH_2)_o$, —O—$(C_1-C_6)$-alkyl, CO(C(R61)(R62))$_r$N(R76)(R77);
R54, R54' are preferably:
H, $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl;
or
R53 and R54 or R53' and R54 form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), CON(R65)(R66), hydroxy, COO(R71), N(R67)CO$(C_1-C_6)$-alkyl, N(R69)(R70) or $SO_2(C_1-C_6)$-alkyl;
R53, R54, R53', R54' are very particularly preferably:
independently of one another $(C_1-C_8)$-alkyl, $(C(R58)(R59))_q$-R60, $(C_1-C_4)$-alkoxy-$(C_1-C_4)$-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), hydroxy, N(R67)CO$(C_1-C_6)$-alkyl, or $SO_2(C_1-C_6)$-alkyl;

o' 0, 1, 2, 3, 4, 5, 6; preferably 0, 1, 2, 3; particularly preferably 0 or 1; very particularly preferably;

R58, R59
independently of one another H, $(C_1-C_6)$-alkyl, OH;
R57, R61, R62, R64, R65, R66, R67, R68, R69, R70, R71
independently of one another H, $(C_1-C_6)$-alkyl;
or
R69 and R70
form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

q, r independently of one another 0, 1, 2, 3, 4, 5, 6;
R60, R63
independently of one another OH, F, O—$(C_1-C_6)$-alkyl, CN, COO(R78), N(R74)CO$(C_1-C_6)$-alkyl, N(R76)(R77), CON(R72)(R73), $SO_2(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, N(R76)(R77), COO(R78), $SO_2(C_1-C_6)$-alkyl and COOH;
preferably OH, F, O—$(C_1-C_6)$-alkyl, N(R74)CO$(C_1-C_6)$-alkyl, $SO_2(C_1-C_6)$-alkyl, 3-12 membered mono-, bi- or spirocyclic ring which may comprise one to three heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, N(R76)(R77) and $SO_2(C_1-C_6)$-alkyl;

R72, R73, R74, R76, R77, R78
independently of one another H, $(C_1-C_8)$-alkyl;
or
R72 and R73, R76 and R77
form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;
where
in the case where L is $(C_1-C_3)$-alkylene,
B is not an aromatic radical, not a cycloalkyl radical, not an alk-2-en-1-yl radical and not a cycloalk-2-en-1-yl radical, and C(R34')=C(R34') is excepted for the group A.

The invention relates to compounds of the formula I in the form of their racemates, enantiomer-enriched mixtures and pure enantiomers, and to their diastereomers and mixtures thereof.

DETAILED DESCRIPTION OF THE INVENTION

The compounds of the formula I are notable for exhibiting an improved solubility compared with compounds of similar structure in an aqueous media and at the same time exhibiting high activity. Preferred compounds of the invention are notable in particular for low blockade of the hERG channel.

The alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R27', R28, R28' R29, R29' R30, R30' R31, R32, R33, R34, R34', R35, R36, R37, R38, R39, R40, R41, R42, R43, R44, R45, R46, R47, R51, R52, R53, R54, R55, R56, R57, R58, R59, R60, R61, R62, R63, R64, R65, R66, R67, R68, R69, R70, R71, R72, R73, R74, R76, R77 and R78 may be either straight-chain, branched and/or optionally substituted by substituents such as $(C_1$-$C_4)$-alkoxy or halogen. This also applies when the alkyl, alkenyl and alkynyl radicals are part of another group, e.g. part of an alkoxy group (such as $(C_1$-$C_4)$-alkoxy-$(C_1$-$C_4)$-alkyl)). Suitable halogens are fluorine, chlorine, bromine and iodine, preferably fluorine, chlorine and bromine, particularly preferably fluorine.

Examples of alkyl groups are: methyl, ethyl, propyl, butyl, pentyl, hexyl, heptyl and octyl. Included therein are both the n-isomers of these radicals and branched isomers such as isopropyl, isobutyl, isopentyl, sec-butyl, tert-butyl, neopentyl, 3,3-dimethylbutyl, etc. Unless described otherwise, the term alkyl additionally also includes alkyl radicals which are unsubstituted or optionally substituted by one or more further radicals, for example by 1, 2, 3 or 4 identical or different radicals such as (C1-C4)-alkoxy or halogen. Examples of alkyl groups substituted by halogen are fluorinated alkyl groups such as CF3, CHF2, CH2F, 3-fluoroprop-1-yl, 2,2,1,1-tetrafluoroethyl. It is moreover possible for the additional substituents to appear in any desired position of the alkyl radical. Unless defined otherwise, the alkyl radicals are preferably unsubstituted.

Cycloalkyl means in the context of the present application cycloalkyl and cycloalkylalkyl (alkyl which is in turn substituted by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as listed by way of example above for the alkyl radicals. Unless defined otherwise, the cycloalkyl radicals are preferably unsubstituted.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl.

Cycloalkenyl means in the context of the present application cycloalkenyl radicals and cycloalkenylalkyl radicals (alkyl which is substituted by cycloalkenyl), which comprise at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or non-conjugated double bonds (i.e. also alk-dienyl and alk-trienyl radicals), preferably one double bond in a linear or branched chain. The same applies to the triple bonds for alkynyl radicals. The alkenyl and alkynyl radicals may be unsubstituted or optionally substituted by one or more further radicals as listed by way of example above for the alkyl radicals. Unless defined otherwise, the alkenyl and alkynyl radicals are preferably unsubstituted.

Aryl refers in the present invention to radicals which are derived from monocyclic or bicyclic aromatic compounds comprising no ring heteroatoms. Where aryl refers to systems which are not monocyclic, the saturated form (perhydro form) or the partly unsaturated form (for example the dihydro form or tetrahydro form) is also possible for the second ring when the respective forms are known and stable. The term aryl also includes in the present invention for example bicyclic radicals in which both rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl. Unless defined otherwise, the aryl radicals are preferably unsubstituted. Aryl is particularly preferably phenyl or naphthyl.

Heteroaryl radicals mean radicals derived from monocyclic or bicyclic aromatic compounds which comprise ring heteroatoms, preferably N, O or S. Otherwise, the statements made about aryl radicals apply to heteroaryl radicals.

A "tricycle" means structures having 3 rings which are linked together by more than one bond. Examples of such systems are fused systems with 3 rings and spirocycles with fused-on ring system.

A polycyclic group (bi-, tri- or spirocyclic ring structure) means in the context of the present application a group which is derived from spiranes, fused ring systems or bridged ring systems. The spiranes are notable for two rings having only one carbon atom in common and the ring planes of the two rings being perpendicular to one another. In the fused ring systems, two rings are linked together in such a way that they have two atoms in common. This type of linkage involves an "ortho fusion". Bridged ring systems are ring systems having a bridge of carbon atoms and/or heteroatoms between two nonadjacent atoms of a ring.

A "chemically reasonable radical" means in the context of the present invention a radical which is stable at room temperature and atmospheric pressure. In the context of the present invention, a "chemically reasonable radical" in the definition of group A in compounds of the formula I preferably means groups which have no heteroatom-heteroatom bonds between the individual members of the groups.

A "nonaromatic" ring means in the context of the present application preferably a ring which is saturated or partly unsaturated. In this connection, a partly unsaturated ring according to the present application has one or, where appropriate, a plurality of double bonds, but the partly unsaturated ring is not aromatic. The term "nonaromatic" in the context of the present application also includes "nonheteroaromatic" rings.

The compounds of the formula I may have one or more centers of asymmetry. The compounds of the formula I may therefore exist in the form of their racemates, enantiomer-enriched mixtures, pure enantiomers, diastereomers and mixtures of diastereomers. The present invention encompasses all these isomeric forms of the compounds of the formula I. These isomeric forms may be obtained by known methods, even if not expressly described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion, such as, for example, trifluoroacetate, likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

If radicals or substituents may occur more than once in the compounds of the formula I, they may all have the stated meanings independently of one another and be identical or different.

The symbols in compound I preferably have independently of one another the following meanings;
where the following compounds are excluded:
in the case where L is $(C_1-C_3)$-alkylene, B is not an aromatic radical, not a cycloalkyl radical, not an alk-2-en-1-yl radical and not a cycloalk-2-en-1-yl radical, and $C(R34')=C(R34')$ is excepted for the group A in this case.

R1, R1', R1", R1'''
 preferably H, F, Cl, Br, OH, $CF_3$, $NO_2$, CN, $OCF_3$, O—$(C_1-C_6)$-alkyl, $(C_1-C_4)$-alkoxy$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_2-C_6)$-alkynyl, O—$(C_0-C_6)$-alkylene-aryl, CO$(C_1-C_6)$-alkyl;
 particularly preferably H, F, Cl, Br, $CF_3$, CN, $OCF_3$, O—$(C_1-C_6)$-alkyl, $(C_1-C_4)$-alkoxy$(C_1-C_4)$-alkyl, $(C_1-C_6)$-alkyl;
 very particularly preferably H, F, Cl, O—$(C_1-C_6)$-alkyl, $(C_1-C_6)$-alkyl;
 where preferably at least two, particularly preferably at least three or all radicals R1, R1', R1" and R1''' are H.

R2 H, F, Cl, Br, I, OH, $CF_3$, $NO_2$, CN, $OCF_3$, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl;
 particularly preferably H, F, Cl, Br, $CF_3$, CN, $OCF_3$, O—$(C_1-C_6)$-alkyl, $(C_1-C_4)$-alkoxy$(C_1-C_4)$-alkyl, $(C_1-C_6)$-alkyl;
 very particularly preferably H, F, Cl, O—$(C_1-C_6)$-alkyl, $(C_1-C_6)$-alkyl;
 in particular very particularly preferably H.

Y C(R27)(R27')C(R28)(R28'); where
 R27, R27', R28, R28', R29, R29'
  are independently of one another H, $(C_1-C_8)$-alkyl; preferably H.

X S, C(R30)=C(R30'); particularly preferably C(R30)=C(R30'); where

R30, R30'
 are independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), $(C(R24)(R25))_x$-O(R6);
 preferably H, F, Cl, Br, I, OH, $CF_3$, $NO_2$, CN, $OCF_3$, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl;
 particularly preferably H, F, Cl, Br, $CF_3$, CN, $OCF_3$, O—$(C_1-C_6)$-alkyl, $(C_1-C_4)$-alkoxy-$(C_1-C_4)$-alkyl, $(C_1-C_6)$-alkyl;
 very particularly preferably H, F, Cl, O—$(C_1-C_6)$-alkyl, $(C_1-C_6)$-alkyl;
 in particular very particularly preferably H.

A a bond or a linker having 1 to 6 members, where the members are selected from the group consisting of O, $SO_2$, N(R31), CO, C(R32)(R33), C(R34)=C(R34'), C≡C, resulting in a chemically reasonable radical;
 particularly preferably a bond or a linker having 1 to 5 members, where the members are selected from the group consisting of O, $SO_2$, N(R31), CO, C(R32)(R33), C≡C, resulting in a chemically reasonable radical;
 very particularly preferably a bond or a linker having 1 to 5 members, where the members are selected from the group consisting of O, $SO_2$, N(R31), CO, C(R32)(R33), C≡C, resulting in a chemically reasonable radical, where the linker comprises no O—CO or CO—O groups;
 in particular preferably a bond, O, C≡C, $CH_2$—O, $CH_2CH_2O$, $COCH_2O$, $CH_2$—C≡C, O—CO—$CH_2$—C≡C, O—CO—$CH_2$—O, $CH_2CH_2CH_2O$, $COCH_2CH_2O$;
 in particular very preferably O, C≡C, $CH_2$—O, $CH_2CH_2O$, $COCH_2O$, $CH_2$—C≡C, O—CO—$CH_2$—C≡C, O—CO—$CH_2$—O, $CH_2CH_2CH_2O$, $COCH_2CH_2O$; where R31, R34, R34'
 are independently of one another H, $(C_1-C_8)$-alkyl;

R32, R33
 are independently of one another H, $(C_1-C_6)$-alkyl, OH, O—$(C_1-C_6)$-alkyl.

B H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;
 particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;

very particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO($C_1-C_6$)-alkyl, N(R42)(R43) or $SO_2CH_3$;

R35, R36, R37, R38, R39, R40, R41, R42, R43
independently of one another H, $(C_1-C_8)$-alkyl;
or R38 and R39, R42 and R43
form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur; where R35, R36, R37, R38, R39, R40, R41, R42, R43
are preferably independently of one another H, $(C_1-C_8)$-alkyl.

In a preferred embodiment, B is:

B H, N(R35)(R36), hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi-, tri- or spirocyclic nonaromatic ring which may comprise 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO($C_1-C_6$)-alkyl, N(R42)(R43), $SO_2CH_3$, $SCF_3$ or S—$(C_1-C_6)$-alkyl;

preferably H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic nonaromatic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO($C_1-C_6$)-alkyl, N(R42)(R43) or $SO_2CH_3$;

particularly preferably H, hydroxy-$(C_1-C_4)$-alkyl, $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO($C_1-C_6$)-alkyl, N(R42)(R43) or $SO_2CH_3$;

very particularly preferably hydroxy-$(C_1-C_4)$-alkyl, $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO($C_1-C_6$)-alkyl, N(R42)(R43) or $SO_2CH_3$;

in particular preferably $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO($C_1-C_6$)-alkyl or $SO_2CH_3$;

in particular particularly preferably hydroxy-$(C_1-C_4)$-alkyl, $(C_1-C_8)$-alkyl, $(C_1-C_4)$-alkoxy-$(C_1-C_4)$-alkyl, a monocyclic ring selected from the group:

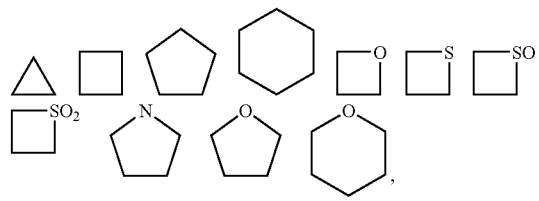

where the ring system may additional be substituted once or twice by F, $CF_3$, CN, methyl, ethyl, methoxy, oxo, hydroxy, $SO_2$-methyl;

in particular very particularly preferably hydroxy-$(C_1-C_4)$-alkyl, $(C_1-C_8)$-alkyl, $(C_1-C_4)$-alkoxy-$(C_1-C_4)$-alkyl, monocyclic ring selected from the group:

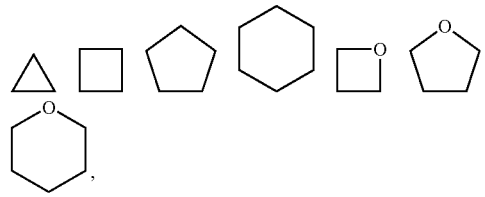

where the ring system may additional be substituted once or twice by F, $CF_3$, methyl, ethyl, methoxy, oxo, hydroxy; where R35, R36, R37, R38, R39, R40, R41, R42, R43 have the meanings mentioned above.

In a very particularly preferred embodiment the group B-A has the meaning:

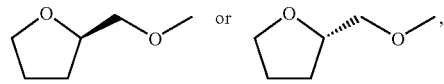

wherein the ring may be substituted
once by methyl or OH.

In a further very particularly preferred embodiment the group B-A has the meaning:

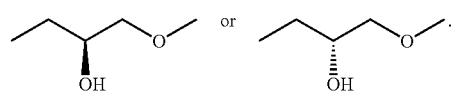

L a bond, $(C_1-C_3)$-alkylene; preferably a bond, $CH_2$, $(CH_2)_2$, $(CH_2)_3$.

Q N(R53')(R54'), a bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, CF$_3$, CN, OCF$_3$, oxo, O—(C$_1$-C$_8$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, CO(R44), (C(R45)(R46))$_o$-R47, CO(C(R45)(R46))$_p$-R48; where R44 is H, (C$_1$-C$_8$)-alkyl;

R45, R46
  are independently of one another H, (C$_1$-C$_6$)-alkyl; particularly preferably H;

o, p are independently of one another 0, 1, 2, 3, 4;

R47, R48
  are independently of one another OH, F, O—(C$_1$-C$_8$)-alkyl, CON(R49)(R50), N(R51)CO(R52), N(R53)(R54), CO$_2$(R55), SO$_2$Me, CN, a 3-10 membered ring system having 0 to 3 heteroatoms selected from the group of N, O and S, which may be substituted by one or more of the following substituents: F, Cl, Br, CF$_3$, (C$_1$-C$_8$)-alkyl, O—(C$_1$-C$_8$)-alkyl, (C$_1$-C$_4$)-alkoxy-(C$_1$-C$_4$)-alkyl, CO(R56), oxo, OH;

R49, R50, R51, R52, R55, R56
  are independently of one another H, (C$_1$-C$_8$)-alkyl;
or
R49 and R50
  form optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur;

R53, R53':
  are independently of one another H, (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl, CO—(C$_1$-C$_8$)-alkyl, CO—(CH$_2$)$_o$—O—(C$_1$-C$_6$)-alkyl, CO(C(R61)(R62))$_r$N(R76)(R77);

R54, R54':
  are independently of one another H, (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl;
or
R53 and R54 or R53' and R54' form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl;

R53, R54, R53', R54' are very particularly preferably:
  independently of one another (C$_1$-C$_8$)-alkyl, (C(R58)(R59))$_q$-R60, (C$_1$-C$_4$)-alkoxy-(C$_1$-C$_4$)-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), hydroxy, N(R67)CO(C$_1$-C$_6$)-alkyl, or SO$_2$(C$_1$-C$_6$)-alkyl;

o' 0, 1, 2, 3; particularly preferably 0 or 1;

R58, R59
  are independently of one another H, (C$_1$-C$_6$)-alkyl, OH;

R57, R61, R62, R64, R65, R66, R67, R69, R70, R71
  are independently of one another H, (C$_1$-C$_6$)-alkyl;
or
R69 and R70
  form optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur;

q, r are independently of one another 0, 1, 2, 3, 4, 5, 6;

R60, R63
  are independently of one another OH, F, O—(C$_1$-C$_6$)-alkyl, N(R74)CO(C$_1$-C$_6$)-alkyl, SO$_2$(C$_1$-C$_6$)-alkyl, 3-12 membered mono-, bi- or spirocyclic ring which may comprise one or more heteroatoms from the group of N, O and S, and the 3-12 membered ring further substituents such as F, Cl, Br, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, N(R76)(R77) and SO$_2$(C$_1$-C$_6$)-alkyl;

R72, R73, R74, R76, R77, R78
  are independently of one another H, (C$_1$-C$_8$)-alkyl;
or
R72 and R73, R76 and R77
  form independently of one another optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur.

In a further preferred embodiment Q is:

Q a bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, CF$_3$, CN, OCF$_3$, oxo, O—(C$_1$-C$_8$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, CO(R44), (C(R45)(R46))$_o$-R47, CO(C(R45)(R46))$_p$-R48;

where the radicals and indices R44, R45, R46, R47, R48, o and p have the meanings mentioned above for Q.

In a preferred embodiment, Q is:

Q N(R53')(R54') or a group selected from

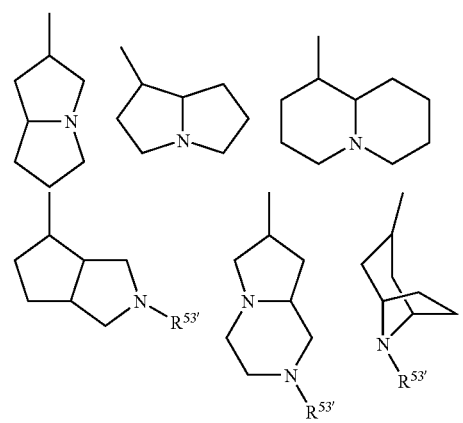

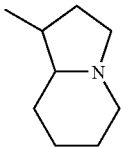

where the groups may, apart from R53', in each case optionally be substituted by one or more of the radicals F, OH, oxo, (C$_1$-C$_8$)-alkyl, O—(C$_1$-C$_8$)-alkyl, (C$_1$-C$_4$)-alkoxy-(C$_1$-C$_4$)-alkyl; the groups are preferably unsubstituted;

preferably N(R53')(R54') or a group selected from

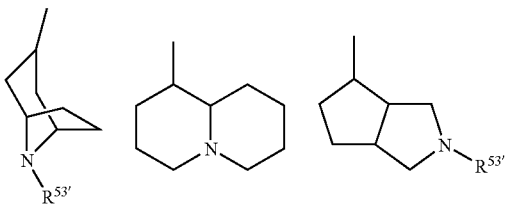

where the groups may, apart from R53', in each case optionally be substituted by one or more of the aforementioned radicals; the groups are preferably unsubstituted;

particularly preferably a group selected from

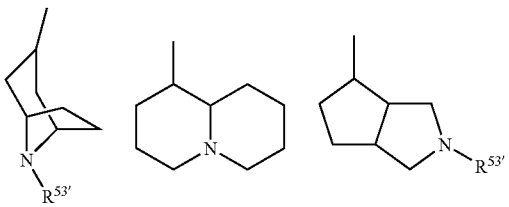

where the groups may, apart from R53', in each case optionally be substituted by one or more of the aforementioned radicals; the groups are preferably unsubstituted;

very particularly preferably

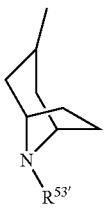

in which the radicals R53' and R54' have the aforementioned meanings.

In a further preferred embodiment the radicals R53' and R54' have the meanings:

R53' H, (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl, CO—(C$_1$-C$_8$)-alkyl, CO—(CH$_2$)$_o$-O—(C$_1$-C$_6$)-alkyl, CO(C(R61)(R62))$_r$N(R76)(R77);

R54' (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl;

or

R53' and R54' form together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl;

o' 0, 1, 2, 3, 4, 5, 6;

q, r independently of one another 0, 1, 2, 3, 4, 5, 6;

particularly preferred:

R53' (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl, CO—(C$_1$-C$_8$)-alkyl, CO—(CH$_2$)$_o$-O—(C$_1$-C$_6$)-alkyl, CO(C(R61)(R62))$_r$N(R76)(R77);

R54' (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl;

or

R53' and R54' form together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl;

o' 0, 1, 2, 3, 4, 5, 6;

q, r independently of one another 0, 1, 2, 3, 4, 5, 6;

very particularly preferred:

R53', R54'
independently of one another (C$_1$-C$_8$)-alkyl, (C(R58)(R59))$_q$-R60, (C$_1$-C$_4$)-alkoxy-(C$_1$-C$_4$)-alkyl; or R53' and R54' form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), hydroxy, N(R67)CO(C$_1$-C$_6$)-alkyl, or SO$_2$(C$_1$-C$_6$)-alkyl;

R60 OH, F, O—(C$_1$-C$_6$)-alkyl, N(R74)CO(C$_1$-C$_6$)-alkyl, SO$_2$(C$_1$-C$_6$)-alkyl, 3-12 membered mono-, bi- or spirocyclic ring which may comprise one or more heteroatoms from the group of N, O and S, and the 3-12 membered ring may comprise further substituents such as F, Cl, Br, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, N(R76)(R77) and SO$_2$(C$_1$-C$_6$)-alkyl.

In a particularly preferred embodiment the radicals R53' and R54' have the meanings:

R53' and R54' form together with the nitrogen atom to which they are bonded a 4 to 7-membered monocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl.

In a further particularly preferred embodiment the radicals R53' and R54' have the meanings:

R53' and R54' form together with the nitrogen atom to which they are bonded a 6 to 10-membered bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl.

In a very particularly preferred embodiment the radicals R53' and R54' have the meanings:

R53' and R54' form together with the nitrogen atom to which they are bonded a 6 to 10-membered bi- or spirocyclic ring which, apart from the nitrogen atom, may comprise 0 to 3 additional heteroatoms selected from the group of oxygen, nitrogen and sulfur, where the heterocyclic ring system is additionally substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl.

In a very particularly preferred embodiment, the radicals R53' and R54' have the meanings: R53' und R54' form together with the nitrogen atom to which they are bonded a 6 to 10-membered bi- or spirocyclic non aromatic ring selected from the group:

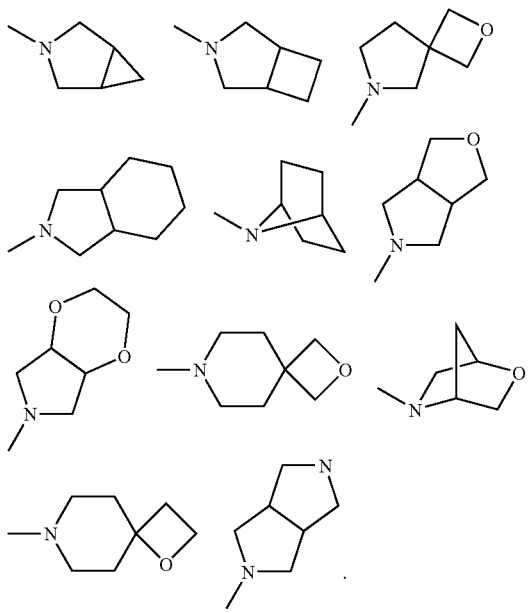

In a further preferred embodiment, the present invention relates to compounds of the general formula I, in which Y and X have the following meanings:

Y C(R27)(R27')C(R28)(R28'); and

R27, R27', R28, R28' independently of one another independently of one another H, (C$_1$-C$_8$)-alkyl; preferably H;

and

X S, O; preferably S.

In a further preferred embodiment, the present invention relates to compounds of the general formula I, in which Y and X have the following meanings:

Y C(R29)=C(R29');

R29, R29' and

X S, O, C(R30)=C(R30'); preferably S, C(R30)=C(R30');

R30, R30' independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$—CH$_3$, COOH, COO—(C$_1$-C$_6$)-alkyl, CON(R17)(R18), N(R19)CO(R20), N(R21)SO$_2$(R22), CO(R23), (CR24R25)$_{x'}$—O(R26);

preferably H, F, Cl, Br, I, OH, CF$_3$, NO$_2$, CN, OCF$_3$, O—(C$_1$-C$_6$)-alkyl, (C$_1$-C$_4$)-alkoxy(C$_1$-C$_4$)-alkyl, (C$_1$-C$_6$)-alkyl, (C$_2$-C$_6$)-alkenyl, (C$_2$-C$_6$)-alkynyl;

particularly preferably H, F, Cl, Br, CF$_3$, CN, OCF$_3$, O—(C$_1$-C$_6$)-alkyl, (C$_1$-C$_4$)-alkoxy(C$_1$-C$_4$)-alkyl, (C$_1$-C$_6$)-alkyl;

very particularly preferably H, F, Cl, O—(C$_1$-C$_6$)-alkyl, (C$_1$-C$_6$)-alkyl;

in particular very particularly preferably H.

In a further embodiment, the present invention relates to compounds of the formula Ia (Ia)

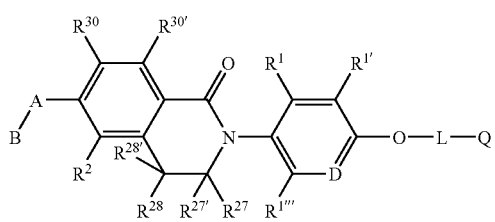

in which the symbols and radicals have the aforementioned meanings.

In a further preferred embodiment, the present invention relates to compounds of the formula I in which O-L-Q is:

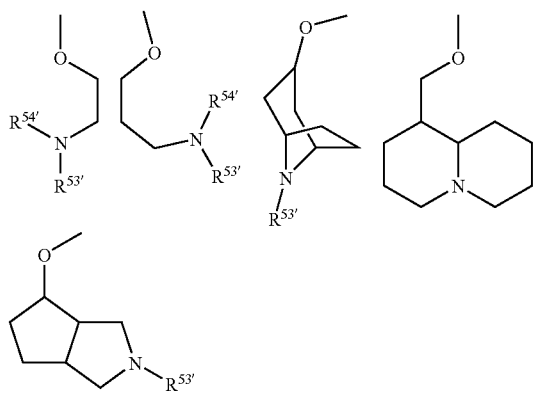

where the groups may, apart from R53', in each case optionally be substituted by one or more of the radicals F, OH, oxo, (C$_1$-C$_8$)-alkyl, O—(C$_1$-C$_8$)-alkyl, (C$_1$-C$_4$)-alkoxy-(C$_1$-C$_4$)-alkyl; the groups are preferably unsubstituted;

O-L-Q is preferably:

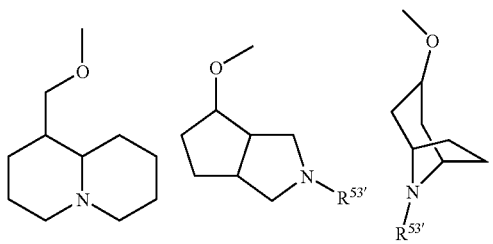

where the groups may, apart from R53', in each case optionally be substituted by one or more of the aforementioned radicals; the groups are preferably unsubstituted;
O-L-Q is particularly preferably:

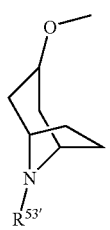

where the group may, apart from R53', optionally be substituted by one or more of the aforementioned radicals; the group is preferably unsubstituted;
in which the radicals R53' and R54' have the following meanings:
R53' $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl, CO—$(C_1-C_8)$-alkyl, CO—$(CH_2)_o$—O—$(C_1-C_6)$-alkyl, CO(C(R61)(R62))$_r$N(R76)(R77);
R54' $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl;
or
R53' and R54' form preferably together with the nitrogen atom to which they are bonded a 4 to 10-membered mono-, bi- or spirocyclic ring which, apart from the nitrogen atom, may comprise 0 to 4 additional heteroatoms selected from the group of oxygen, nitrogen and sulfur, where the heterocyclic ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), CON(R65)(R66), hydroxy, COO(R71), N(R67)CO($C_1-C_6$)-alkyl, N(R69)(R70) or $SO_2(C_1-C_6)$-alkyl;
R53', R54' are preferably:
independently of one another $(C_1-C_8)$-alkyl, $(C(R58)(R59))_q$-R60, $(C_1-C_4)$-alkoxy-$(C_1-C_4)$-alkyl; or R53' and R54' form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), hydroxy, N(R67)CO($C_1-C_6$)-alkyl, or $SO_2(C_1-C_6)$-alkyl;

o' 0, 1, 2, 3, 4, 5, 6; preferably 0, 1, 2, 3; particularly preferably 0 or 1; very particularly preferably 0;
R58, R59
independently of one another H, $(C_1-C_6)$-alkyl, OH;
R61, R62, R64, R65, R66, R67, R69, R70, R71
independently of one another H, $(C_1-C_6)$-alkyl;
or
R69 and R70
form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;
q, r independently of one another 0, 1, 2, 3, 4, 5, 6;
R60 OH, F, O—$(C_1-C_6)$-alkyl, CN, COO(R78), N(R74)CO($C_1-C_6$)-alkyl, N(R76)(R77), CON(R72)(R73), $SO_2(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, N(R76)(R77), COO(R78), $SO_2(C_1-C_6)$-alkyl and COOH;
preferably OH, F, O—$(C_1-C_6)$-alkyl, N(R74)CO($C_1-C_6$)-alkyl, $SO_2(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, N(R76)(R77) and $SO_2(C_1-C_6)$-alkyl;
R72, R73, R74, R76, R77, R78
independently of one another H, $(C_1-C_8)$-alkyl;
or
R72 and R73, R76 and R77
form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur.
In a further particularly preferred embodiment O-L-Q is:

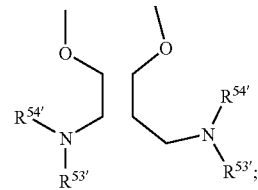

R53' $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl, CO—$(C_1-C_8)$-alkyl, CO—$(CH_2)_o$—O—$(C_1-C_6)$-alkyl, CO(C(R61)(R62))$_r$N(R76)(R77);
R54' $(C(R58)(R59))_q$-R60, $(C_1-C_4)$-alkoxy-$(C_1-C_4)$-alkyl, $(C_3-C_8)$-alkenyl, $(C_3-C_8)$-alkynyl;
or
R53' and R54' form together with the nitrogen atom to which they are bonded a 6 to 10-membered bi- or spirocyclic nonaromatic ring which, apart from the nitrogen atom, may comprise 0 to 3 additional heteroatoms selected from the group of oxygen, nitrogen and sulfur, where the heterocyclic ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl.

In a further very particularly preferred embodiment, the present invention relates to compounds of the formula I in which O-L-Q, X and Y is:
X C(R30)=C(R30');
Y C(R29)=C(R29');

O—L—Q

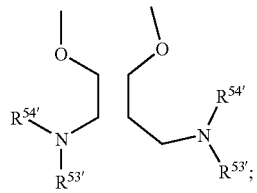

R53' (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl, CO—(C$_1$-C$_8$)-alkyl, CO—(CH$_2$)$_o$—O—(C$_1$-C$_6$)-alkyl, CO(C(R61)(R62))$_r$N(R76)(R77);

R54' (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl; or R53' and R54' form together with the nitrogen atom to which they are bonded a 6 to 10-membered bi- or spirocyclic nonaromatic ring which, apart from the nitrogen atom, may comprise 0 to 3 additional heteroatoms selected from the group of oxygen, nitrogen and sulfur, where the heterocyclic ring system may additionally be substituted by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl;

R60 OH, F, O—(C$_1$-C$_6$)-alkyl, N(R74)CO(C$_1$-C$_6$)-alkyl, 3-12 membered mono-, bi- or spirocyclic nonaromatic ring which may comprise one or more heteroatoms from the group of N, O and S, and the 3-12 membered ring may comprise further substituents such as F, Cl, Br, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, N(R76)(R77) and SO$_2$(C$_1$-C$_6$)-alkyl.

The present invention thus relates in a particularly preferred embodiment to the compounds of the general formula Ib Ib

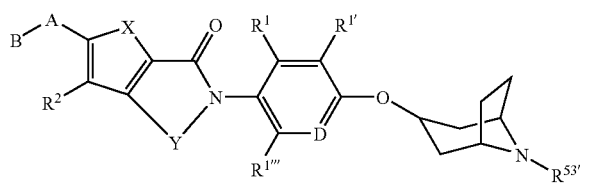

in which radicals and groups in the compound of the formula Ib have the aforementioned meanings.

R53' in the compounds of the formula Ib is preferably (C$_1$-C$_8$)-alkyl, particularly preferably methyl.

In a further preferred embodiment, the present invention relates to compounds of the formula I in which O-L-Q and B are:

O—L—Q:

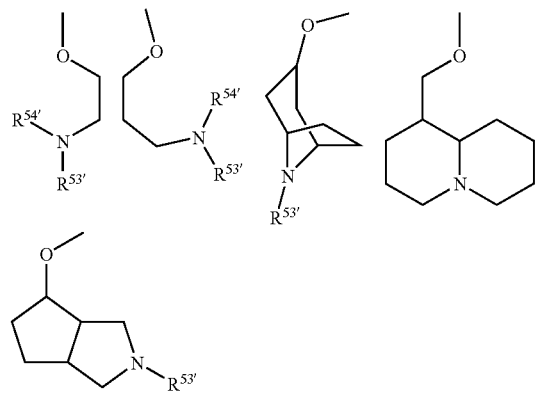

where the groups may, apart from R53' and R54', in each case optionally be substituted by one or more of the radicals F, OH, oxo, (C$_1$-C$_8$)-alkyl, O—(C$_1$-C$_8$)-alkyl, (C$_1$-C$_4$)-alkoxy-(C$_1$-C$_4$)-alkyl; the groups are preferably unsubstituted;

O-L-Q is preferably:

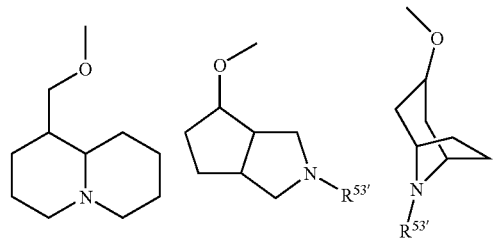

where the groups may, apart from R53', in each case optionally be substituted by one or more of the aforementioned radicals; the groups are preferably unsubstituted;

O-L-Q is particularly preferably:

where the group may, apart from R53', optionally be substituted by one or more of the aforementioned radicals; the group is preferably unsubstituted;

in which the radicals R53' and R54' have the following meanings:

R53' H, (C$_1$-C$_8$)-alkyl, (C(R58)(R59))$_q$-R60, (C$_1$-C$_4$)-alkoxy-(C$_1$-C$_4$)-alkyl, (C$_3$-C$_8$)-alkenyl, (C$_3$-C$_8$)-alkynyl, CO—(C$_1$-C$_8$)-alkyl, CO—(CH$_2$)$_o$—O—(C$_1$-C$_6$)-alkyl, CO(C(R61)(R62))$_r$N(R76)(R77);

R54' H, $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl;

or

R53' and R54 form together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), CON(R65)(R66), hydroxy, COO(R71), N(R67)CO$(C_1-C_6)$-alkyl, N(R69)(R70) or $SO_2$$(C_1-C_6)$-alkyl;

R53', R54' are particularly preferably:

independently of one another $(C_1-C_8)$-alkyl, $(C(R58)(R59))_q$-R60, $(C_1-C_4)$-alkoxy-$(C_1-C_4)$-alkyl; or R53' and R54' form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1-C_6)$-alkyl, O$(C_1-C_8)$-alkyl, $(C_1-C_4)$-alkoxy-$(C_1-C_4)$-alkyl, hydroxy-$(C_1-C_4)$-alkyl, oxo, CO(R64), hydroxy, N(R67)CO$(C_1-C_6)$-alkyl, or $SO_2$$(C_1-C_6)$-alkyl;

o' 0, 1, 2, 3, 4, 5, 6; preferably 0, 1, 2, 3; particularly preferably 0 or 1; very particularly preferably 0;

R58, R59 independently of one another H, $(C_1-C_6)$-alkyl, OH;

R61, R62, R64, R65, R66, R67, R69, R70, R71 independently of one another H, $(C_1-C_6)$-alkyl;

or

R69 and R70 form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

q, r independently of one another 0, 1, 2, 3, 4, 5, 6;

R60 OH, F, O—$(C_1-C_6)$-alkyl, CN, COO(R78), N(R74)CO$(C_1-C_6)$-alkyl, N(R76)(R77), CON(R72)(R73), $SO_2$$(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, N(R76)(R77), COO(R78), $SO_2$$(C_1-C_6)$-alkyl and COOH;

preferably OH, F, O—$(C_1-C_6)$-alkyl, N(R74)CO$(C_1-C_6)$-alkyl, $SO_2$$(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, N(R76)(R77) and $SO_2$$(C_1-C_6)$-alkyl;

R72, R73, R74, R76, R77, R78 independently of one another H, $(C_1-C_8)$-alkyl;

or

R72 and R73, R76 and R77 form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

and

B H, N(R35)(R36), hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi-, tri- or spirocyclic nonaromatic ring which may comprise 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl or $SO_2CH_3$;

preferably H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic nonaromatic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;

particularly preferably H, hydroxy-$(C_1-C_4)$-alkyl, $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;

very particularly preferably hydroxy-$(C_1-C_4)$-alkyl, $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl, N(R42)(R43) or $SO_2CH_3$;

in particular preferably $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl or $SO_2CH_3$;

in particular particularly preferably hydroxy-$(C_1-C_4)$-alkyl, $(C_1-C_8)$-alkyl, $(C_1-C_4)$-alkoxy-$(C_1-C_4)$-alkyl, a monocyclic ring selected from the group:

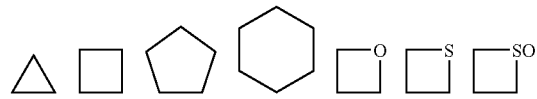

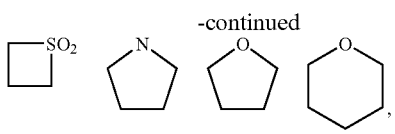

where the ring system may additional be substituted once or twice by F, $CF_3$, CN, methyl, ethyl, methoxy, oxo, hydroxy, $SO_2$-methyl;

in particular very particularly preferably hydroxy-$(C_1$-$C_4)$-alkyl, $(C_1$-$C_8)$-alkyl, $(C_1$-$C_4)$-alkoxy-$(C_1$-$C_4)$-alkyl, monocyclic ring selected from the group:

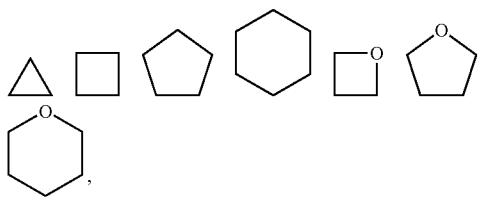

where the ring system may additional be substituted once or twice by F, $CF_3$, methyl, ethyl, methoxy, oxo, hydroxy; where R35, R36, R37, R38, R39, R40, R41, R42, R43 have the meanings mentioned above.

In a further embodiment, the present invention relates to compounds of the formula Ic

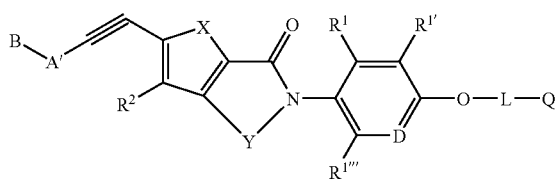

(Ic)

in which the meanings are:

A' a bond or a linker having 1 to 5 members, where the members are selected from the group consisting of O, S, $SO_2$, N(R31), CO, C(R32)R(R33), resulting in a chemically reasonable radical;
  preferably a bond or a linker having 1 to 4 members, where the members are selected from the group consisting of O, $SO_2$, N(R31), CO, C(R32)(R33) resulting in a chemically reasonable radical;
  particularly preferably a bond or a linker having 1 to 4 members, where the members are selected from the group consisting of O, $SO_2$, N(R31), CO, C(R32)(R33) resulting in a chemically reasonable radical, where the linker has no CO—O or CO—O groups;

R31 independently of one another H, $(C_1$-$C_8)$-alkyl;

R32, R33
  independently of one another H, $(C_1$-$C_6)$-alkyl, OH, O—$(C_1$-$C_6)$-alkyl;

Y C(R27)(R27')C(R28)(R28'), C(R29)=C(R29'); preferably C(R29)-C(R29');

R27, R27', R28, R28', R29, R29'
  independently of one another H, $(C_1$-$C_8)$-alkyl; preferably H;

where the further radicals and groups have the aforementioned meanings.

The compounds of the invention of the general formula I can be prepared in analogy to processes known to the skilled worker. Suitable processes for preparing the compounds of the invention of the general formula I are mentioned by way of example below (see in particular methods A, B, C1, C2, D, E, F, G, H, I, J, K, L, M, N, O, P, Q, R, S, T, U, V and schemes 1 to 3).

A novel reaction sequence for preparing the compounds of the invention of the general formula I includes the following steps:

i) dimetallation of aromatic carboxylic acids alkylated, preferably methylated, in the ortho position, to form a dianion, and trapping of the formed dianion with aldehydes or reagents which liberate aldehydes, such as paraformaldehyde, resulting in corresponding substituted aromatic carboxylic acids which have a hydroxyalkyl substituent in the position ortho to the carboxylic acid group, and where appropriate preparation of the corresponding bicyclic lactones from the substituted aromatic carboxylic acids which have a hydroxyalkyl substituent in the position ortho to the carboxylic acid group, by elimination of water;

ii) subsequent reaction of the substituted aromatic carboxylic acids which have a hydroxyalkyl substituent in the position ortho to the carboxylic acid group, or where appropriate of the corresponding bicyclic lactones, with a halogenating agent, resulting in the corresponding haloalkyl-substituted aroyl halides;

iii) subsequent reaction of the haloalkyl-substituted aroyl halides with primary aromatic amines, and subsequent cyclization of the resulting reaction products by addition of base to give pyridone-fused aromatic compounds; and iv) where appropriate further reaction of the pyridone-fused aromatic compounds;

resulting in the compounds of the formula I.

Depending on the substitution pattern of the compounds of the general formula I, the desired compounds are obtained directly after the reaction in step iii), or a further reaction (step iv)) is necessary where appropriate in order to obtain the desired compounds of the general formula I. Suitable reaction conditions for carrying out the individual steps of the aforementioned process are known to the skilled worker.

Preferred embodiments of said steps, as well as the preparation of the starting substances employed in the steps, are known to the skilled worker below and mentioned by way of example in said schemes and methods, and examples.

This invention further relates to the use of compounds of the formula I and their pharmaceutical compositions as MCH receptor ligands. The MCH receptor ligands of the invention are particularly suitable as modulators of the activity of the MCH1R. The role of MCH in regulating the energy balance has now been well documented (Qu, D. et al. Nature 1996, 380, 243-7; Shimada, M. et al. Nature 1998, 396, 670-4; Chen, Y et al. Endocrinology 2002, 143, 2469-77; Endocrinology 2003, 144, 4831-40; Review: G. Hervieu, Expert Opin. Ther. Targets 2003, 7, 495-511; Shi, Y., Peptides 2004, 25, 1605-11).

There are also indications that MCH antagonists can have a beneficial influence on centrally related disorders such as, for example, anxiety states, depressions (Borowsky, B. et al. Nature Medicine 2002, 8, 825-30; Review: G. Hervieu, Expert Opin. Ther. Targets 2003, 7, 495-511; Chaki, S. et al., Drug Dev. Res. 2005, 65, 278-290; Dyck, B., Drug Dev. Res. 2005, 65, 291-300).

Compounds of this type are particularly suitable for the treatment and/or prevention of
1. Obesity
2. Diabetes mellitus, especially type 2 diabetes, including the prevention of the sequelae associated therewith.
    Particular aspects in this connection are
    hyperglycemia,
    improvement in insulin resistance,
    improvement in glucose tolerance,
    protection of the pancreatic β cells
    prevention of macro- and microvascular disorders
3. Dyslipidemias and the sequelae thereof such as, for example, atherosclerosis, coronary heart disease, cerebrovascular disorders etc, especially those (but not restricted thereto) which are characterized by one or more of the following factors:
    high plasma triglyceride concentrations, high postprandial plasma triglyceride concentrations
    low HDL cholesterol concentration
4. Various other conditions which may be associated with the metabolic syndrome, such as:
    thromboses, hypercoagulable and prothrombotic stages (arterial and venous)
    high blood pressure
    heart failure such as, for example (but not restricted thereto), following myocardial infarction, hypertensive heart disease or cardiomyopathy
5. Psychiatric indications such as
    depressions
    anxiety states
    disturbances of the circadian rhythm
    affection disorders
    schizophrenia
    addictive disorders Formulations The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of body weight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contains a defined amount of at least one compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain at least one compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of at least one compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing at least one compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished as selective MCH1R antagonists by their low toxicity, the small effect on metabolizing enzymes and their few side effects. In particular, preferred compounds of the invention are notable for low blockade of the hERG channel. In addition, preferred compounds of the formula I are noticeably soluble in aqueous systems and thus particularly suitable for pharmaceutical development. The pharmacological effect is moreover achieved in in vivo test models after oral administration from well-tolerated vehicles.

The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure.

Combinations with Other Medicaments

The compounds of the invention can be administered alone or in combination with one or more further pharmacologically active substances which have, for example, beneficial effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes
11. active ingredients for the treatment of neurodegenerative conditions
12. active ingredients for the treatment of diseases of the central nervous system
13. active ingredients for the treatment of medicament-, nicotine- or alcohol addiction
14. pain killers They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples of active ingredients suitable for combination products are listed below:

All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus®9 (see www.lantus.com) or Apidra® (HMR 1964) or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1-derivatives such as, for example, exenatide, liraglutide or those which have been disclosed in WO98/08871 or WO2005027978 of Novo Nordisk A/S, in WO01/04156 of Zealand or in WO0/34331 of Beaufour-Ipsen, Pramlintide Acetate (Symlin; Amylin Pharmaceuticals), and orally effective hypoglycemic active ingredients.

The active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase
modulators of glucose transporter 4 (GLUT4),
inhibitors of glutamine-fructose-6-phosphate amidotransferase (GFAT),
GLP-1 agonists, potassium channel openers such as, for example, those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis, PPAR and RXR modulators and
active ingredients which act on the ATP-dependent potassium channel of the beta cells.

In one embodiment of the invention, at least one compound of the formula I is administered in combination with an HMGCoA reductase inhibitor such as simvastatin, fluvastatin, pravastatin, lovastatin, atorvastatin, cerivastatin, rosuvastatin or L-659699

In one embodiment of the invention, at least one compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, at least one compound of the formula I is administered in combination with a PPAR gamma agonist such as, for example, rosiglitazone, pioglitazone, JTT-501, GI 262570, R-483 or CS-011 (rivoglitazone).

In one embodiment of the invention, at least one compound of the formula I is administered in combination with a PPAR alpha agonist such as, for example, GW9578, GW-590735, K-111, LY-674, KRP-101 or DRF-10945.

In one embodiment of the invention, at least one compound of the formula I is administered in combination with a mixed PPAR alpha/gamma agonist such as, for example, muraglitazar, tesaglitazar, naveglitazar, LY-510929, ONO-5129, E-3030 or as described in WO00/64888, WO00/64876, WO03/020269, WO2004075891, WO2004076402, WO2004075815, WO2004076447, WO2004076428, WO2004076401, WO2004076426, WO2004076427, WO2006018118, WO2006018115, und WO2006018116 or in J. P. Berger et al., TRENDS in Pharmacological Sciences 28(5), 244-251, 2005.

In one embodiment of the invention, at least one compound of the formula I is administered in combination with a PPAR delta agonist such as, for example, GW-501516 or as described in WO2005097762, WO2005097786, WO2005097763, und WO2006029699.

In one embodiment, at least one compound of the formula I is administered in combination with metaglidasen or with MBX-2044 or other partial PPAR gamma agonists/antagonists.

In one embodiment of the invention, at least one compound of the formula I is administered in combination with a fibrate such as, for example, fenofibrate, clofibrate or bezafibrate.

In one embodiment of the invention, at least one compound of the formula I is administered in combination with an MTP inhibitor such as, for example, implitapide, BMS-201038, R-103757 or those described in WO2005085226.

In one embodiment of the invention, at least one compound of the formula I is administered in combination with a CETP inhibitor such as, for example, torcetrapib or JTT-705.

In one embodiment of the invention, at least one compound of the formula I is administered in combination with a bile acid absorption inhibitor (see, for example, U.S. Pat. Nos. 6,245,744, 6,221,897 or WO00/61568), such as, for example, HMR 1741 or those as described in DE 10 2005 033099.1 and DE 10 2005 033100.9.

In one embodiment of the invention, at least one compound of the formula I is administered in combination with a polymeric bile acid adsorbent such as, for example, cholestyramine or colesevelam.

In one embodiment of the invention, at least one compound of the formula I is administered in combination with an LDL receptor inducer (see U.S. Pat. No. 6,342,512), such as, for example, HMR1171, HMR1586 or those as described in WO2005097738.

In one embodiment, at least one compound of the formula I is administered in combination with Omacor® (omega-3 fatty acids; highly concentrated ethyl esters of eicosapentaenoic acid and of docosahexaenoic acid).

In one embodiment of the invention, at least one compound of the formula I is administered in combination with an ACAT inhibitor such as, for example, avasimibe.

In one embodiment of the invention, at least one compound of the formula I is administered in combination with an antioxidant such as, for example, OPC-14117, probucol, tocopherol, ascorbic acid, β-carotene or selenium.

In one embodiment of the invention, at least one compound of the formula I is administered in combination with a vitamin such as, for example, vitamin B6 or vitamin B12.

In one embodiment of the invention, at least one compound of the formula I is administered in combination with a lipoprotein lipase modulator such as, for example, ibrolipim (NO-1886).

In one embodiment of the invention, at least one compound of the formula I is administered in combination with an ATP citrate lyase inhibitor such as, for example, SB-204990.

In one embodiment of the invention, at least one compound of the formula I is administered in combination with a squalene synthetase inhibitor such as, for example, BMS-188494 or as described in WO2005077907.

In one embodiment of the invention, at least one compound of the formula I is administered in combination with a lipoprotein(a) antagonist such as, for example, gemcabene (CI-1027).

In one embodiment of the invention, at least one compound of the formula I is administered in combination with an HM74A receptor agonist such as, for example, nicotinic acid.

In one embodiment of the invention, at least one compound of the formula I is administered in combination with a lipase inhibitor such as, for example, orlistat or cetilistat (ATL-962).

In one embodiment, at least one compound of the formula I is administered in combination with insulin.

In one embodiment, at least one compound of the formula I is administered in combination with a sulfonylurea such as, for example, tolbutamide, glibenclamide, glipizide or glimepiride.

In one embodiment, at least one compound of the formula I is administered in combination with a biguanide such as, for example, metformin.

In another embodiment, at least one compound of the formula I is administered in combination with a meglitinide such as, for example, repaglinide or nateglinide.

In one embodiment, at least one compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, at least one compound of the formula I is administered in combination with an α-glucosidase inhibitor such as, for example, miglitol or acarbose.

In one embodiment, at least one compound of the formula I is administered in combination with an active ingredient which acts on the ATP-dependent potassium channel of the beta cells, such as, for example, tolbutamide, glibenclamide, glipizide, glimepiride or repaglinide.

In one embodiment, at least one compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, at least one compound of the formula I is administered in combination with substances which influence hepatic glucose production, such as, for example an inhibitor of glycogen phosphorylase, such as, for example, PSN-357 or FR-258900 or those as described in WO2003084922, WO2004007455, WO2005073229-31 or WO2005067932.

In one embodiment, at least one compound of the formula I is administered in combination with glucagon receptor antagonists such as, for example, A-770077, NNC-25-2504 or as described in WO2004100875 or WO2005065680.

In one embodiment, at least one compound of the formula I is administered in combination with activators of glucokinase, such as, for example, RO-4389620, LY-2121260 (WO2004063179), PSN-105, PSN-110, GKA-50 or such as described in WO2004072031, WO2004072066, WO 05103021, WO 06016178, WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 4,067,939, WO 04052869, EP 1532980, WO 03055482, WO 04002481, WO 05049019, WO 05066145, WO 05123132, WO 03080585, WO 03097824, WO 04081001, WO 05063738, WO 05090332, WO 04063194, WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment, at least one compound of the formula I is administered in combination with an inhibitor of gluconeogenesis, such as, for example, FR-225654.

In one embodiment, at least one compound of the formula I is administered in combination with inhibitors of fructose-1,6-bisphosphatase (FBPase), such as, for example, CS-917.

In one embodiment, at least one compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, at least one compound of the formula I is administered in combination with inhibitors of glutamine-fructose-6-phosphate amidotransferase (GFAT), as are described for example in WO2004101528.

In one embodiment, at least one compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964× or as are described in WO2003074500, WO2003106456, WO200450658, WO2005058901, WO2005012312, WO2005012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, at least one compound of the formula I is administered in combination with inhibitors of 11-beta-hydroxysteroid dehydrogenase 1 (11β-HSD1), such as, for example, BVT-2733 or those as are described for example in WO200190090-94, WO200343999, WO2004112782, WO200344000, WO200344009, WO2004112779, WO2004113310, WO2004103980, WO2004112784, WO 2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment, at least one compound of the formula I is administered in combination with inhibitors of protein tyrosine phosphatase 1B (PTP1B), as are described for example in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment, at least one compound of the formula I is administered in combination with modulators of the sodium-dependent glucose transporter 1 or 2 (SGLT1, SGLT2), such as, for example, KGA-2727, T-1095, SGL-0010, AVE 2268 and SAR 7226 or as are described for example in WO2004007517, WO200452903, WO200452902, WO2005121161, PCT/EP2005/005959, WO2005085237, JP2004359630 or by A. L. Handlon in Expert Opin. Ther. Patents (2005) 15(11), 1531-1540.

In one embodiment, at least one compound of the formula I is administered in combination with modulators of GPR40.

In one embodiment, at least one compound of the formula I is administered in combination with inhibitors of hormone-sensitive lipase (HSL) as described for example in WO01/17981, WO01/66531, WO2004035550, WO2005073199 or WO03/051842.

In one embodiment, at least one compound of the formula I is administered in combination with inhibitors of acetyl-CoA carboxylase (ACC), such as, for example, those as described in WO199946262, WO200372197, WO2003072197 or WO2005044814.

In one embodiment, at least one compound of the formula I is administered in combination with an inhibitor of phosphoenolpyruvate carboxykinase (PEPCK), such as, for example, those as described in WO2004074288.

In one embodiment, at least one compound of the formula I is administered in combination with an inhibitor of glycogen synthase kinase 3 beta (GSK-3 beta), as described for example in US2005222220, WO2005085230, WO2005111018, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, at least one compound of the formula I is administered in combination with an inhibitor of protein kinase C beta (PKC beta), such as, for example, ruboxistaurin.

In one embodiment, at least one compound of the formula I is administered in combination with an endothelin A receptor antagonist such as, for example, avosentan (SPP-301).

In one embodiment, at least one compound of the formula I is administered in combination with inhibitors of "I-kappaB kinase" (IKK inhibitors), as are described for example in WO2001000610, WO2001030774, WO2004022553 or WO2005097129.

In one embodiment, at least one compound of the formula I is administered in combination with modulators of the glucocorticoid receptor, like those described for example in WO2005090336.

In a further embodiment, at least one compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-amino-quinazolin-2-ylamino)methyl] cyclohexylmethyl}amide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;

cannabinoid receptor 1 antagonists (such as, for example, rimonabant, SR147778 or those as are described for example in EP 0656354, WO 00/15609, WO02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897);

MC4 agonists (e.g. 1-amino-1,2,3,4-tetrahydronaphthalene-2-carboxylic acid [2-(3a-benzyl-2-methyl-3-oxo-2,3, 3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076 or WO2004072077;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403 or WO2005075458);

histamine H3 receptor agonists (e.g. ABT-834, ABT-239, 3-cyclohexyl-1-(4,4-dimethyl-1,4,6,7-tetrahydroimidazo[4, 5-c]pyridin-5-yl)propan-1-one oxalic acid salt (WO 00/63208) or those as are described in WO200064884, WO2005082893, FR2870846WO2005037810, Celanire, S., et al. Drug Discovery Today 2005, 10, 1613-1627);

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);
urocortin agonists;
β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;
MCH (melanin-concentrating hormone) receptor antagonists (such as, for example, NGD-4715, AMG-076, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002002744, WO2003004027 or FR2868780);

CCK-A agonists (such as, for example, {2-[4-(4-chloro-2, 5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);
mixed serotoninergic and noradrenergic compounds (e.g. WO 00/71549);

5-HT receptor agonists, e.g. 1-(3-ethylbenzofuran-7-yl) piperazine oxalic acid salt (WO 01/09111);

5-HT6 receptor agonists (such as, for example, APD-356, BVT-933 or those as are described in WO200077010, WO20077001-02, WO2005019180, WO2003064423, WO200242304 or WO2005082859);

5-HT6 receptor antagonists as are described for example in WO2005058858;

bombesin receptor agonists (BRS-3 agonists);
galanin receptor antagonists;
growth hormone (e.g. human growth hormone or AOD-9604);

growth hormone-releasing compounds (tertiary butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);
uncoupling protein 2 or 3 modulators;
leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);

DA agonists (bromocriptine or Doprexin);
lipase/amylase inhibitors (like those described for example in WO 00/40569);

inhibitors of diacylglycerol O-acyltransferases (DGATs) as described for example in US2004/0224997, WO2004094618, WO200058491, WO2005044250, WO2005072740, JP2005206492 or WO2005013907;

inhibitors of fatty acid synthase (FAS) such as, for example, C75 or those as described in WO2004005277;
oxyntomodulin;
oleoyl-estrone;
or thyroid hormone receptor agonists such as, for example: KB-2115 or those as described in WO20058279, WO200172692, WO200194293, WO2003084915, WO2004018421 or WO2005092316.

In one embodiment, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, at least one compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main. Combination with Caromax® is possible in one preparation or by separate administration of compounds of the formula I and Caromax®. Caromax® can in this connection also be administered in the form of food products such as, for example, in bakery products or muesli bars.

In one embodiment, at least one compound of the formula I is administered in combination with PDE (Phosphodiesterase) inhibitors such as, for example, described in WO2003/077949 or WO2005012485.

In one embodiment, at least one compound of the formula I is administered in combination with NAR-1 (Nicotinic acid receptor) agonists such as for example described in WO2004094429.

In one embodiment, at least one compound of the formula I is administered in combination with CB2 (Cannabinoid receptor 2) agonists such as for example described in US2005/143448.

In one embodiment, at least one compound of the formula I is administered in combination with H1 (Histamine receptor 1) agonists such as for example described in WO2005101979.

In one embodiment, at least one compound of the formula I is administered in combination with Bupropion, such as for example described in WO2006017504.

In one embodiment, at least one compound of the formula I is administered in combination with Opiate receptor-antagonists such as for example described in WO2005107806 or WO2004094429.

In one embodiment, at least one compound of the formula I is administered in combination with inhibitors of the neutral Endopeptidase such as for example described in WO200202513, WO2002/06492, WO 2002040008, WO2002040022 or WO2002047670.

In one embodiment, at least one compound of the formula I is administered in combination with NPY (Neuropeptide Y) modulators such as for example described in WO2002047670.

In one embodiment, at least one compound of the formula I is administered in combination with a inhibitor of the sodium/hydrogen replacement protein such as described for example in WO2003092694.

In one embodiment, at least one compound of the formula I is administered in combination with modulators of the glucocorticoid receptor such as for example described in WO2005090336.

In one embodiment, at least one compound of the formula I is administered in combination with nicotine receptor-agonists such as for example described in WO2004094429.

In one embodiment, at least one compound of the formula I is administered in combination with NRIs (Norepinephrine reuptake inhibitor) such as for example described in WO2002053140.

In one embodiment, at least one compound of the formula I is administered in combination with MOA (E-beta-Methoxyacrylate), such as for example segeline, or such as for example described in WO2002053140.

In one embodiment, at least one compound of the formula I is administered in combination with an antithrombotic active ingredient such as for example Clopidogrel.

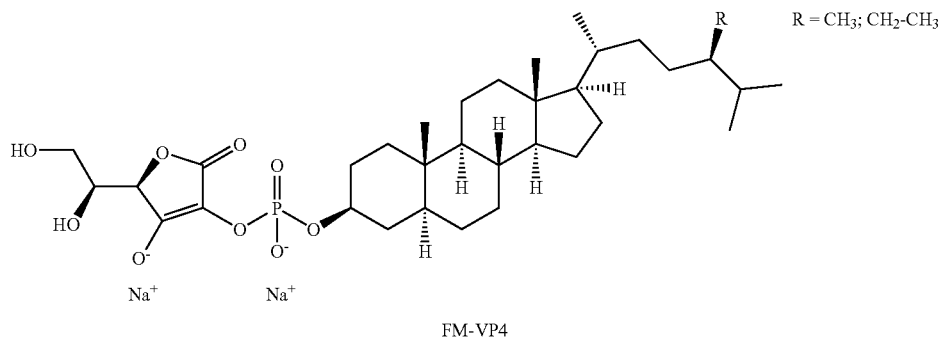

FM-VP4

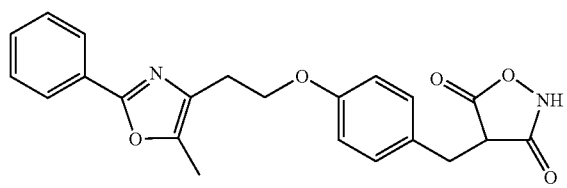

JTT-501

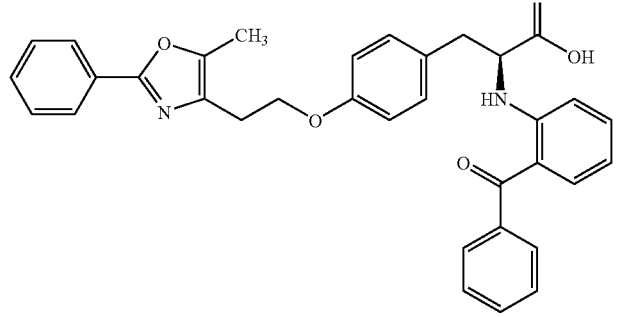
GI 262570
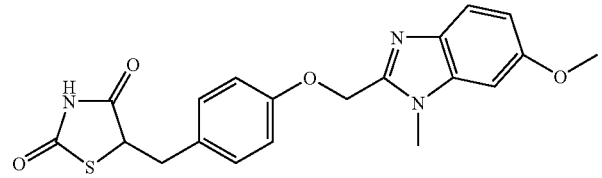
CS-011
rivoglitazone
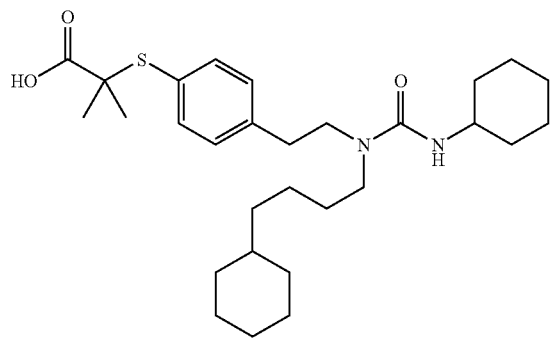
GW-9578
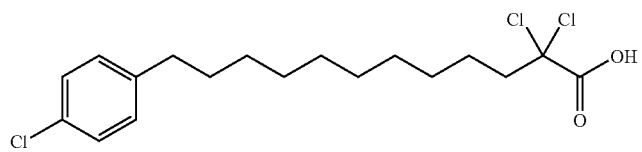
K-111
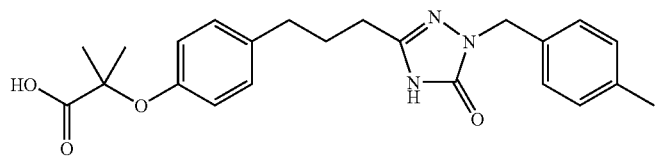
LY-674
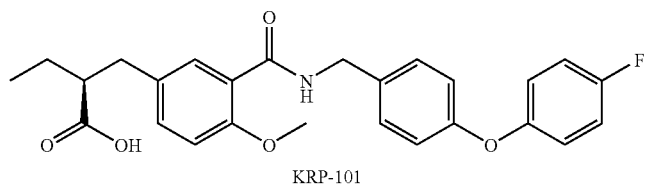
KRP-101
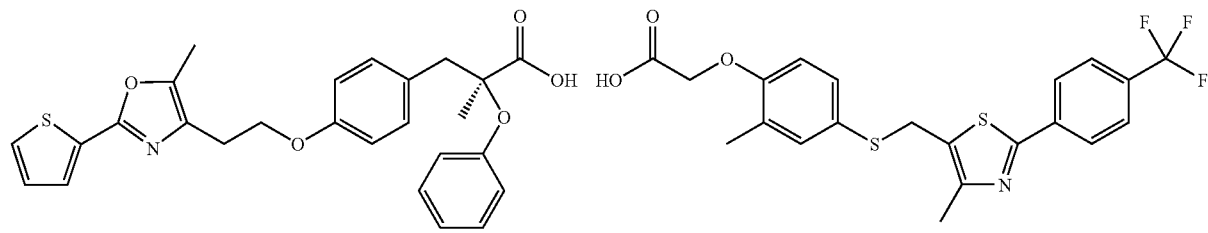
LY-510929
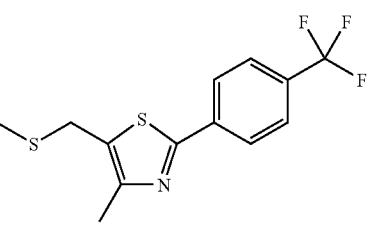
GW-501516

-continued
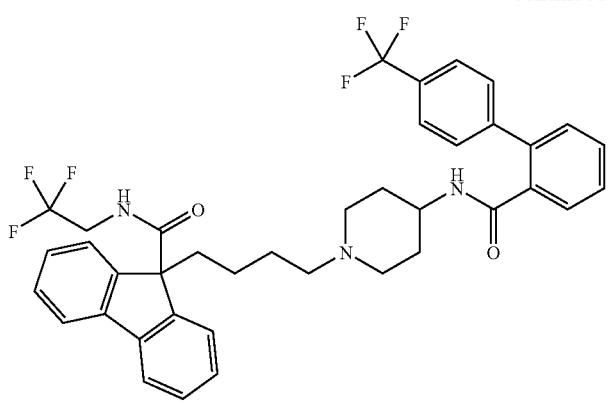
BMS-201038
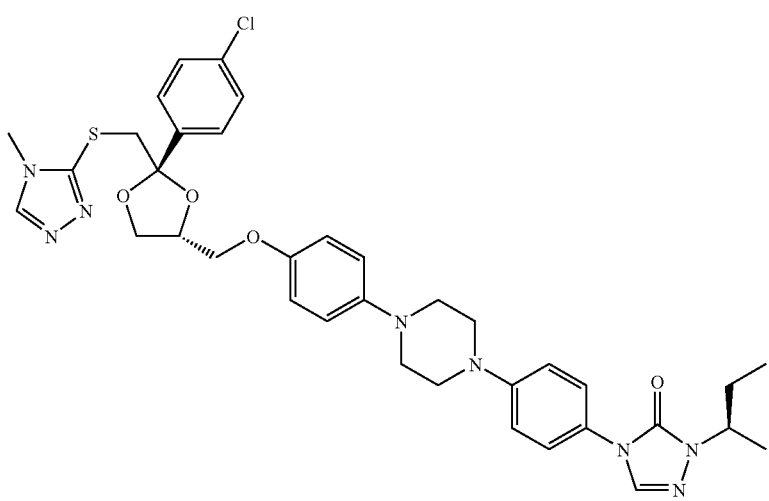
R-103757
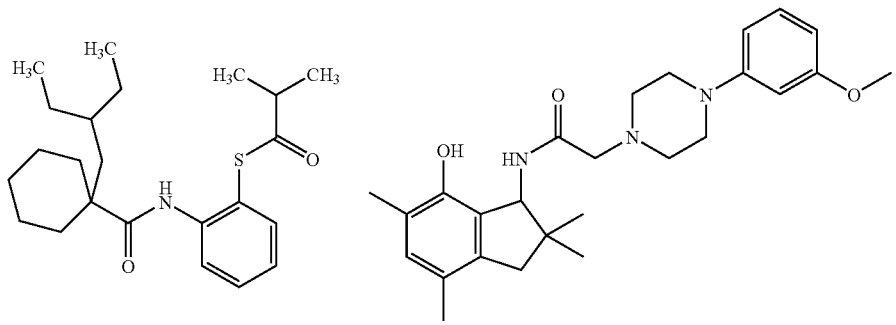
JTT-705      OPC-14117
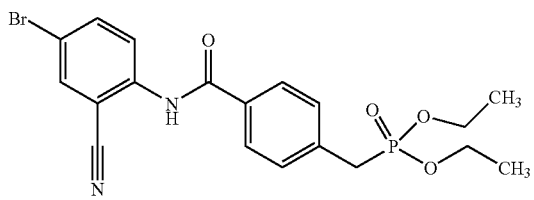
NO-1886
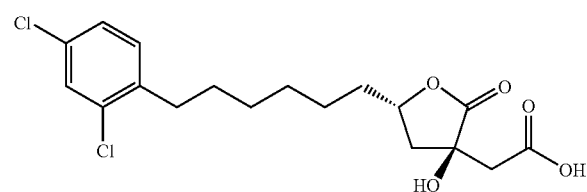
SB-204990

-continued
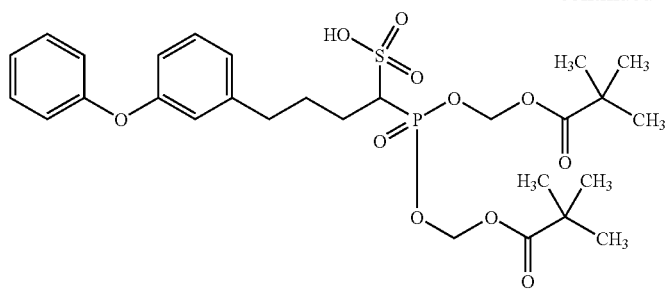
BMS-188494
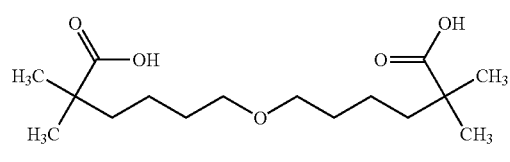
Cl-1027
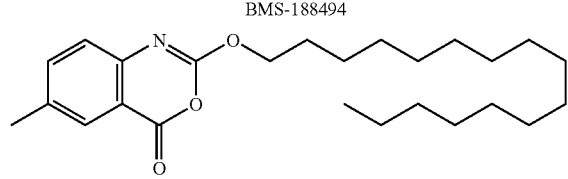
ATL-962
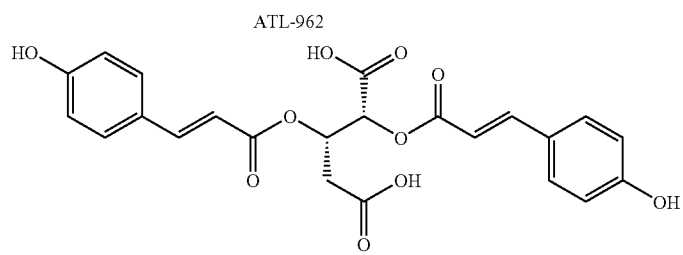
FR-258900
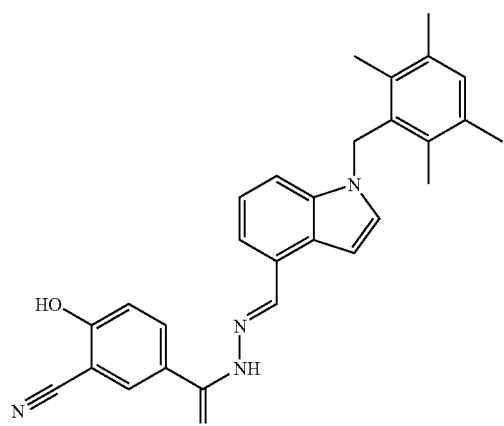
NNC-25-2504
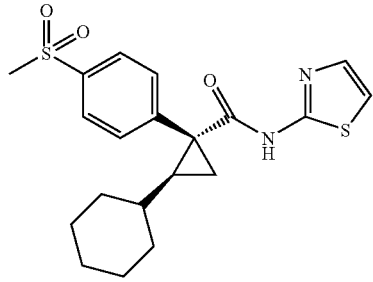
LY-2121260
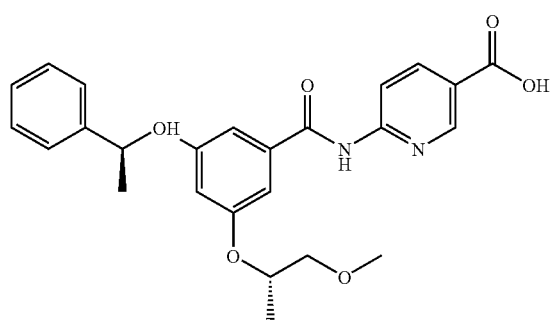
GKA-50
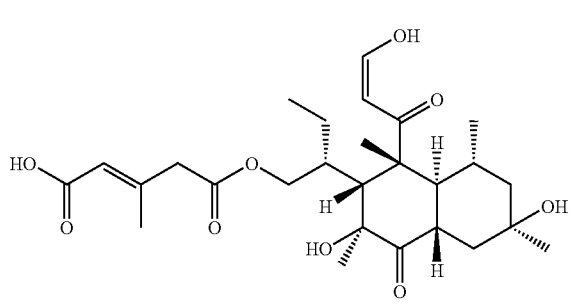
FR-225654

-continued
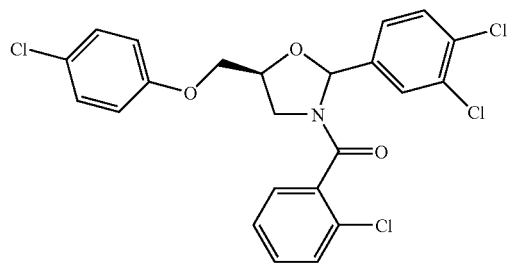
KST-48
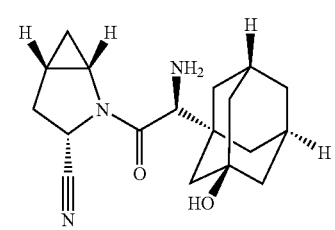
BMS-477118
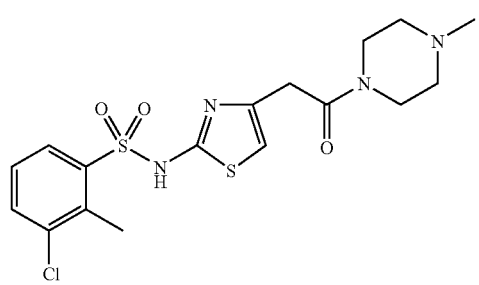
BVT-2733
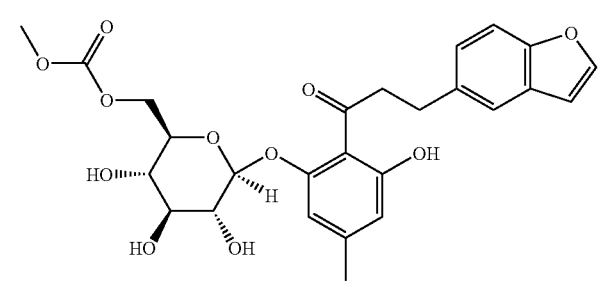
T-1095
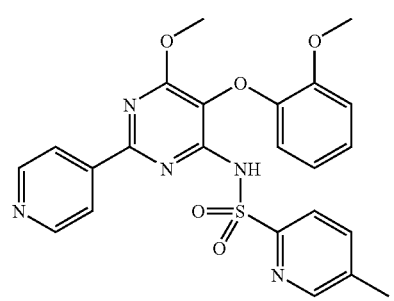
SPP-301
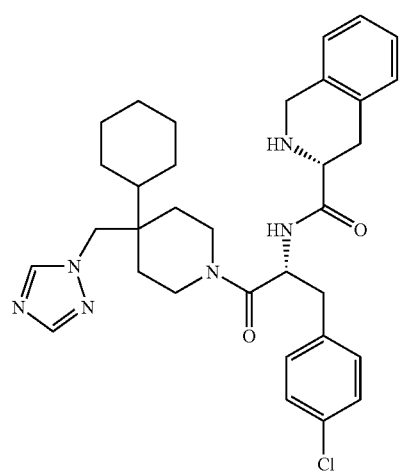
THIQ
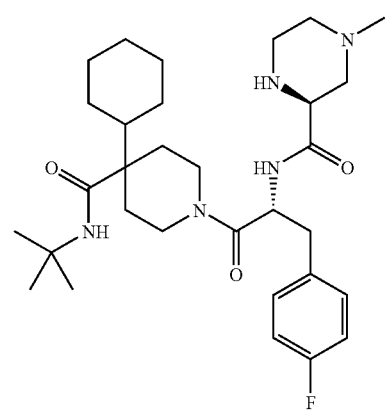
MB243
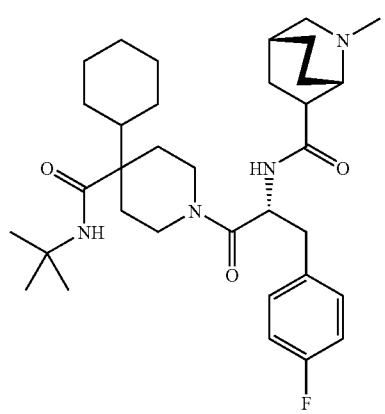
RY764
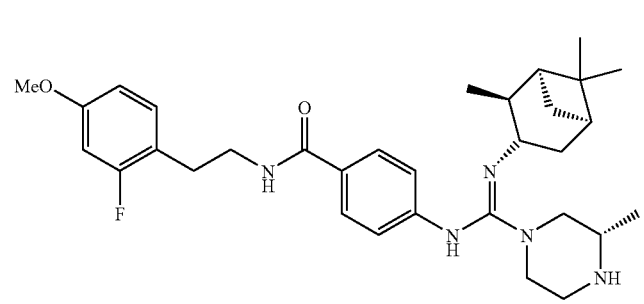
CHIR-785

47
-continued
48
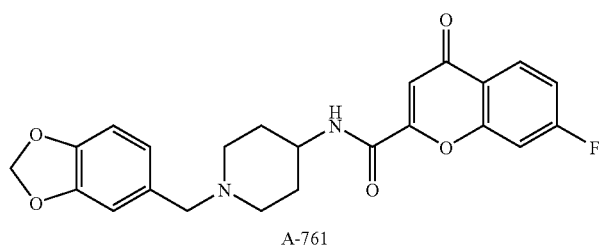
A-761
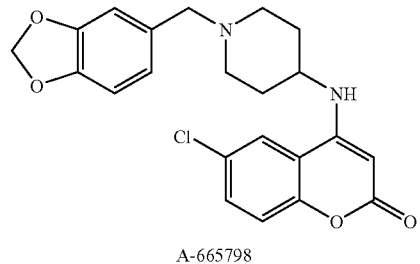
A-665798
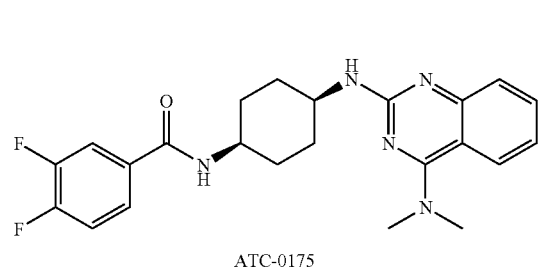
ATC-0175
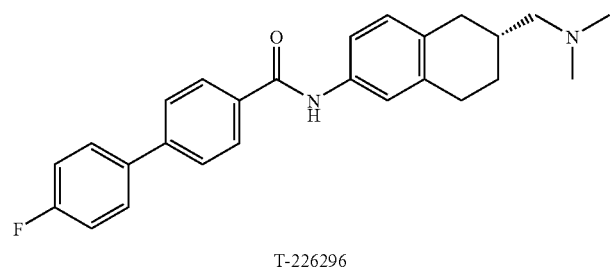
T-226296
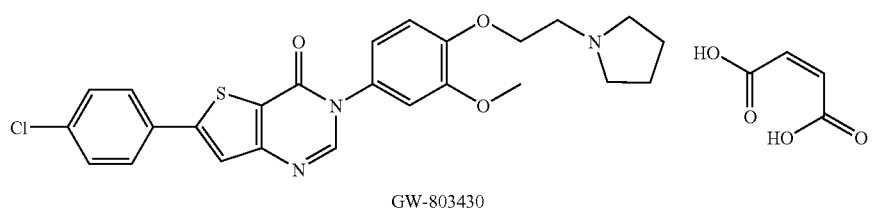
GW-803430
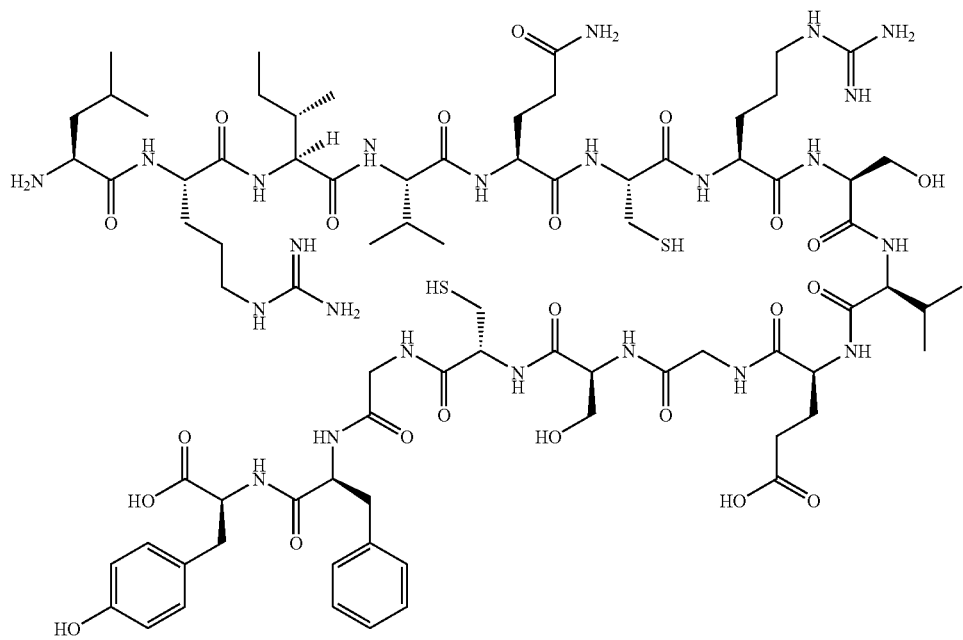
AOD-9604

-continued

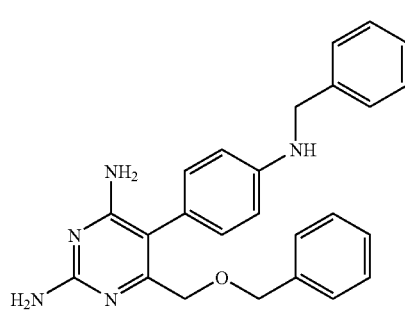
A-778193

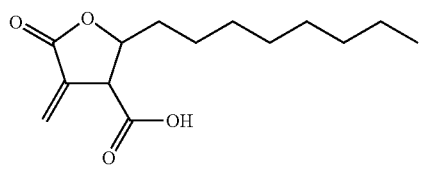
C75

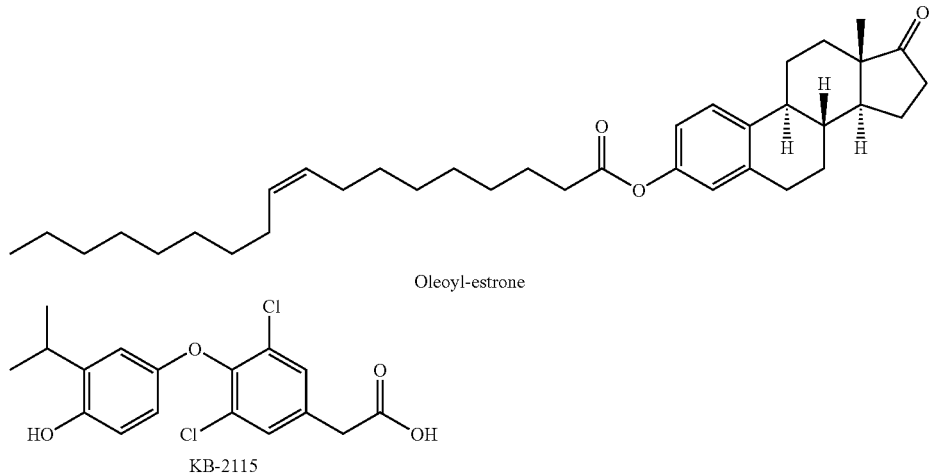
Oleoyl-estrone

KB-2115

In one embodiment, the compounds of the formula I are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

Pharmacological Testing

Test Models

Suitability of the compounds of the invention as active pharmaceutical ingredient can be tested by means of various test models. Descriptions are given of such test models by way of example below.

Influence on the MCH receptor in vitro; determination of functional IC50 values of MCH1R antagonists Cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 276, 13554-13562, 2001). A difference from the reference was, however, the use of the plasmid pEAK8 from EDGE Biosystems (USA) for the construction of the expression vector. The host used for the transfection was a transformed HEK cell line named "PEAK Stable Cells" (likewise from EDGE Biosystems). Functional measurements of the cellular calcium flux after addition of agonist (MCH) in the presence of ligand of the invention took place with the aid of the FLIPR apparatus from Molecular Devices (USA), using protocols of the apparatus manufacturer. The compounds of the invention show a significant inhibition (>30%) of the signal induced by the agonist at a concentration of 100 µM, preferably at 10 µM, particularly preferably at 1 µM, very particularly preferably at 100 nM and even more particularly preferably at 10 nM.

Besides the functional activity it is also possible to determine the affinity for the MCH1R according to Audinot et al. (Br. J. Pharmacol. 2001, 133, 371-378). Preferred compounds of the invention show an IC50 of less than 1 µM, particularly preferably of less than 100 nM, very particularly preferably of less than 10 nM and even more particularly preferably of less than 1 mM.

Milk Intake by Female NMRI Mice

The anorectic effect is tested on female NMRI mice. After withdrawal of feed for 24 hours, the test substance is administered intraperitoneally or preferably orally by gavage. The animals are housed singly with free access to drinking water and, 30 minutes after administration of product, are offered condensed milk. The condensed milk consumption is determined every half hour for 7 hours, and the general condition of the animals is observed. The measured milk consumption is compared with the vehicle-treated control animals. The vehicle itself has no influence on feed intake. Preferred tolerated vehicles for the administration are, for example, hydroxyethylcellulose (0.5% in water) or Solutol HS15 (5% in hydroxyethylcellulose (0.5% in water)).

Feed and Water Intake of Female Wistar Rats

As alternative to testing the anorectic effect on NMRI mice, it is also possible analogously to use female Wistar rats weighing about 220-250 g. The animals are accustomed to the experimental environment before the start of the study. In one embodiment, the animals have free access to feed and water up to the start of the experiment. In another embodiment, access of the animals to feed is withdrawn 24 hours before the administration. For the investigation of the test substance, the animals are housed singly with free access to feed and water. Feed intake and water intake are measured continuously every 30 minutes over a period of 22 hours using a computer-assisted system (TSE Drinking & Feeding Monitor). The measured feed and water consumption is compared with the vehicle-treated control animals.

Body Weight Gain of Diet-Induced Obese and Standard-Fed Mice

For these investigations, male C57BL6J mice 5 weeks old (weaning age) are accustomed either to a standard maintenance diet or to a high-fat and thus high-energy diet. After 12 weeks, the normally fed, slim mice have typically reached a body weight of about 25 g, and the fat-fed mice have reached one of about 35 g. The animals are housed singly, and the feed intake and water intake are determined individually. There is free access to feed and water during the experiment.

The test substances are administered orally in a vehicle and always tested by comparison with the vehicle control which is included in parallel. The vehicle itself has no influence on the feed intake, and is normally hydroxyethylcellulose (0.5% in water) or Solutol HS15 (5% in hydroxyethylcellulose (0.5% in water)). A corresponding group of slim mice is kept for each group of diet-induced obese mice.

Feed consumption and water consumption are determined each day in the first week and then once per week by reweighing the offered feed and water, respectively. The body weight is measured each day.

Blood samples are taken before and at the end of the treatment in order to determine serum parameters which provide information about changes in intermediary metabolism. It is additionally possible to determine the body fat content on the living animal by means of an impedance measurement (TOBEC method).

Micronucleus Test (In Vitro)

The aim of the micronucleus test (in vitro) is to examine whether a test compound has the potential to elicit the formation of micronuclei (small membrane-bound DNA fragments) in various cell lines or primary cultures, with or without metabolic activation by S9 liver homogenate. The test system allows differentiation between the clastogenic and aneugenic potential of a test compound by an immunochemical labeling of the kinetochores or by staining the DNA fragments by the FISH (fluorescence in situ hybridization) method.

Brief description: The cells are treated in a 96-well microtiter plate with the test compound. The treatment time is typically 3 hours with metabolic activation or 24 hours without metabolic activation. Twenty four hours after the end of the treatment, the cells are isolated, fixed and stained. The cytotoxicity of the test compound is assessed according to the relative cell growth expressed as percentage growth or taking account of the doubling time as population doubling compared with the negative control. The highest test concentration should show not less than 30% surviving cells, or should be the concentration at which a precipitate of the test compound is observed. Duplicate determinations should be carried out with each test concentration. An accurate detailed description of the experiment is to be found in Kirsch-Volders et al. (Mutation Res. 2003, 540, 153-163).

Evaluation: The structural or numerical chromosomal damage is reported as the increase in the number of cells with micronuclei in an ensemble of 1000 cells at three analyzable test concentrations. The test is regarded as positive in the following cases:

a) the increase in the number of cells with micronuclei is significant by comparison with the negative control (solvent or untreated), or b) the number of micronuclei is increased to a biologically relevant extent, concentration-dependently by comparison with the negative control.

A positive control must show a clear statistically significant effect by comparison with the negative control.

Preferred compounds of the invention are negative in the micronucleus test.

AMES II Test

The aim of the AMES II test is to examine whether a test compound has mutagenic potential.

Brief description: A mixed bacterial strain (mixed strains, 6 different *Salmonella typhimurium* strains with in each case a missence point mutation in the histidine operon) and the *Salmonella typhimurium* strain TA98 for detecting frame shift mutations is treated in a 384-well microtiter plate with various concentrations of the test substance with or without metabolic activation through addition of S9 liver homogenate (accurate descriptions of the experiment are to be found in the literature: P. Gee, D. M. Maron, B. N. Ames; Proc. Natl. Acad. Sci. USA 1994, 91, 11606 and Flückiger-Isler et al.; Mutation Res. 2004, 558, 181 and cit. lit.).

Mutagenic test compounds cause back-mutations and thus restore the functionality of endogenous histidine biosynthesis. Mutated bacteria are thus able to divide and expand to bacterial colonies.

Evaluation: If there is enhanced bacterial growth owing to mutations of the bacteria, then enzymes are digested in the growth medium. As a result, the pH in the medium falls and the color of the added indicator (bromocresol purple) changes from pale violet to yellow. The test is regarded as positive if the number of wells in which a color change is observed per concentration increases significantly by comparison with the control.

Preferred compounds of the invention are negative in the AMES II test.

Cytotoxicity Tests a) LDH Release

The aim of the test for LDH (lactate dehydrogenase) release is to examine whether a compound damages the integrity of the cell wall and may thus cause cell death.

Brief description: The LDH activity which enters the cell supernatant from the cytosol due to cell damage is measured by colorimetry. The cells are treated with the test compound. Fifty microliters of the culture supernatant are removed and mixed with the reaction solution (LDH kit, Roche, Mannheim) in accordance with the manufacturer's information. LDH catalyzes the conversion of lactate into pyruvate. During this, NAD+ is reduced to NADH/H+. The latter in turn reduces, under the influence of the added diaphorase, a likewise added yellow tetrazolium salt to the red formazan.

Evaluation: The formazan is quantified by measuring the absorption at 492 nM (e.g. with TECAN SPECTRAFluor Plus).

Preferred compounds of the invention show no significant increase in LDH activity at concentrations below 10 µM.

Particularly preferred compounds show no increase below a concentration of 50 μM. Even further preferred compounds show no increase below a concentration of 250 μM.

b) Intracellular ATP Content

The aim of the test is to determine the total intracellular ATP content, which is a measure of the energy level and thus the vitality of a cell.

Brief description: 100 μL of cell culture medium are mixed in a well of a microtiter plate with 100 μL of the CellTiter-Glo reagent (following the manufacturer's instructions: Promega Technical Bulletin No. 228, CellTiter-Glo Luminesent Cell Viability Assay). The cultures are shaken at room temperature for 2 minutes and then incubated for 10 minutes until the luminescence signal has stabilized.

Evaluation: The luminescence is recorded, integrating over one second (e.g. with TECAN SPECTRAFluor Plus).

Preferred compounds of the invention show no significant reduction in the ATP levels at concentrations below 10 μM. Particularly preferred compounds show no reduction below a concentration of 50 μM. Even further preferred compounds show no reduction below a concentration of 250 μM.

c) Neutral Red Uptake

The aim of the test is to measure the uptake of neutral red (NR) into the lysosomes/endosomes and vacuoles of living cells, which is a quantitative measure of the number and vitality of the cells.

Brief description: The cells are washed with 150 μL of a preheated phosphate buffer solution (PBS) and incubated with 100 μL of the NR medium at 37° C. in a humidified atmosphere with 7.5% carbon dioxide for 3 hours. After the incubation, the NR medium is removed and the cells are washed with 150 μL of PBS. Removal of the PBS is followed by addition of exactly 150 μL of an ethanol/glacial acetic acid solution. After shaking for 10 minutes, the dye is extracted from the cells to give a homogeneous dye solution. An exact description of the test is to be found in the literature (E. Borenfreund, J. A. Puemer, Toxicol. Lett. 1985, 24(2-3), 119-124).

Evaluation: The absorption of the dye solution is determined at 540 nM using a microtiter plate reader as difference from the absorption of the ethanol/glacial acetic acid solution.

HERG Channel Blockade

The aim of the test is to determine the concentration range in which the test compound blocks the cardiac hERG channel. Blockade of the hERG channel, which is responsible for the Ikr current in the human heart, is associated with potentially fatal arrhythmias.

For expression of the cDNA encoding the HERG channel it was cloned into the pcDNA3 vector (Invitrogen). Chinese hamster oocytes (CHO, American Type Culture Collection, Rockville, Md.) were transfected using lipofectamine (GIBCO/BRL, Grand Island, N.Y.) with the hERG cDNA and selected using G418 (GIBCO/BRL, Grand Island, N.Y.; 500 μg/mL). CHO cells with stable expression of the HERG channel were cultured on a HAM F-12 medium which was supplemented with 10% native bovine serum, 1× penicillin/streptomycin and 500 μg/mL G418 in an atmosphere of 95% air/5% carbon dioxide.

The cells selected for the patch clamp experiment are seeded on a plastic support 18-24 hours before the experiment. HERG channel currents are recorded at room temperature by the whole-cell variant of the patch clamp technique using an Axopatch 200B amplifier (Axon Instruments, Foster City, Calif.). The electrodes (3-6 megaohms resistance) are prepared from TW150F glass capillaries (World Precision Instruments, Sarasota, Fla.) and filled with the pipette solution (120 mM potassium aspartate, 20 mM KCl, 4 mM Na2ATP, 5 mM HEPES, 1 mM MgCl2; adjusted to pH 7.2 with KOH). The HERG channel currents are induced by a positive voltage pulse (20 mV) followed by a negative pulse (−40 mV) and are recorded for later analysis. As soon as the HERG channel current of the cell flushed with the control solution (130 mM NaCl, 5 mM KCl, 2.8 mM NaOAc, 1 mM MgCl2, 10 mM HEPES; 10 mM glucose, 1 mM CaCl2; adjusted to pH 7.4 with NaOH) is stable, the cell is perfused with the test compound dissolved in the above control solution (by dilution of a 10 or 100 mM DMSO solution of the test compound so that the DMSO content is no more than 0.1%). The current is followed continuously until no further changes occur. The same procedure is repeated with increasing concentrations of the test compound. The maximum amplitude of the hERG current is measured in picoAmperes (pA) for each concentration and for each cell. The maximum amplitude in pA for each concentration of the test compound is compared with that of the pure control solution in the same cell and calculated as % of the control value.

Evaluation: The test compound is tested at various concentrations in 3-5 CHO cells which express hERG channel. The IC50 is obtained by use of nonlinear least squares regression (GraphPAD Software, San Diego, Calif.).

General Selectivity

In order to minimize the risk of unwanted side effects, it is desirable to keep the nonselective effect on biologically important functional units (e.g. receptors, ion channels and enzymes; for lists, see, for example, Whitebread, S. et al.; Drug Discovery Today 2005, 10, 1421-33 and Rolland, C. et al.; J. Med. Chem. 2005, 48, 6563-6574) by an active pharmaceutical ingredient as small as possible. General selectivity tests in a large number of in vitro test systems can be carried out by various specialized services (e.g. Cerep, Panlabs).

The compounds of the invention of the formula I exhibit, as selective MCH1R antagonists, selectivity factors of at least 30, preferably of 100, more preferably of 300 and even more preferably of 1000 vis àvis the affinity to other proteins. Examples of such proteins are serotonin receptor subtypes (e.g. the 5-HT2a receptor), muscarine receptor subtypes (e.g. the M1 receptor), adrenergic receptor subtypes (e.g. AR alpha1a), sodium and calcium channels (e.g. the L-type calcium channel).

Solubility in Aqueous Systems

Adequate solubility of a substance in aqueous solvent systems is an important prerequisite for a (reproducible) pharmacological effect. Solubilities in aqueous systems can be determined by various methods. Suitable examples of solution precipitation methods ("kinetic solubility") and methods which investigate the dissolution of a solid sample until an equilibrium is set up ("thermodynamic solubility").

a) Kinetic Solubility

A DMSO solution of the test compound (2.5 mM; 0.5 μL) is pipetted into 200 μL of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 μM using a nephelometer (e.g. Nephelostar Galaxy, BMG Labtech). The concentration of the test compound in the aqueous test solution is then raised to a theoretical 12.5 μM by adding further DMSO solution (2.5 mM; 0.5 μL), and the turbidity measurement is repeated. Further additions of DMSO solutions (1 μL, 2.5 mM; 0.5 μL, 10 mM; then 9×1 μL, 10 mM resulting in theoretical concentrations of 25 μM, 50 μM, 100 μM, 150 μM, 200 μM, 250 μM, 300 μM, 350 μM, 400 μM, 450 μM and 500 μM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values<6.25 µM, 6.25-500 µM and >500 µM.

Preferred compounds of the invention show a kinetic solubility in phosphate buffer (pH 7.4) of at least 12.5 µM; more preferably of at least 50 µM and even more preferably of at least 250 µM.

b) Thermodynamic Solubility

The integrated UV absorption from HPLC UV measurement of serial dilutions of the test compound in DMSO (500 µM, 100 µM, 50 µM, 10 µM and 1 µM) shows a linear correlation with the concentration in a calibration line. The test compound (500 µg) is shaken together with the aqueous test solution (250 mL) in a closed vessel (capacity: 1.5 mL) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration lines and stated as solubility of the test compound in the respective aqueous test solution.

Examples of aqueous test solutions are deionized water or aqueous phosphate buffer with various pH values (e.g. pH 1.2; pH 4.0; pH 6.8; pH 7.4; pH 9.0) which can be prepared from the commercial solution (phosphate buffered saline, 10×, Sigma) by dilution and adjustment with phosphoric acid or sodium hydroxide solution by standard methods.

Preferred compounds of the invention show a solubility in phosphate buffer (pH 7.4) of at least 12.5 µM; more preferably of at least 50 µM and even more preferably of at least 250 µM.

Permeability

The test for permeability is carried out in CACO-2/TC7 cells which have been cultured (DMEM/Glutamax I/Gibco with high glucose content, HEPES 25 mM, 1% NEAA, 10% FBS, 40 µg/mL gentamycin; 37° C. surrounding temperature; 95% humidity and 10% CO2 content) on Becton Dickinson filters (24-well, uncoated) for 21 days. The permeability is tested at a concentration of 20 µM for the test compound (1% DMSO in HBSS) with a pH gradient (apical: pH 6.5 and 0.5% BSA; basolateral: pH 7.4 and 5% BSA). Analysis takes place by means of LCMS/MS. Further descriptions of the test system and references for the experimental procedure are to be found in Balimane, P. V.; Drug Discovery Today 2005, 10(5), 335-343.

Inhibition of CYP Enzymes

The inhibition of CYP enzymes is determined on recombinant enzymes (obtained from Becton Dickinson) and fluorescent substrates (BD/Gentest) as recommended by the manufacturer (see Website http://www.bdbiosciences.com). Further descriptions of the test system and references for the experimental procedure are to be found in Zlokarnik, G.; Drug Discovery Today 2005, 10(21), 1443-1450.

Metabolic Stability

The metabolic stability is determined by incubating the test compound (5 µM) with microsomal liver fractions (1 mg/mL protein with 0.1% w/v BSA; 1 mM NADPH, 0.5% DMSO) at 37° C. Analysis at an incubation time of 0 and 20 minutes takes place by means of LCMS/MS. Further descriptions of the test system and references for the experimental procedure are to be found in Plant, N.; Drug Discovery Today 2004, 9(7), 328-336 and Lau, Y. Y. et al.; Pharmaceutical Res. 2002, 19(11), 1606-1610.

EXAMPLES

The examples and preparation methods detailed below serve to illustrate the invention without, however, restricting it.

The compounds of the invention of the formula I can be prepared by means of reactions known in principle. Thus, isoquinolinones can be prepared for example by the processes described by Alvarez, M. et al., Science of Synthesis 2005, 15, 839-906. A novel reaction sequence (scheme 1) for preparing isoquinolinones consists of initially subjecting substituted benzoic acid derivatives to an ortho metallation, and trapping the formed dianion with, for example, methyl iodide (method C2). The 2-methylbenzoic acids obtained in this way can again be dimetallated and this time the dianion trapped with, for example, paraformaldehyde (method C1). Reaction of the 2-(2-hydroxyethyl)-benzoic acids, or of the bicyclic lactones resulting therefrom by acid-catalyzed intramolecular water elimination, with thionyl chloride affords 2-(2-chloroethyl)benzoyl chlorides as central intermediates (method B). These are cyclized by reaction with primary (aromatic) amines and subsequent addition of strong bases (e.g. sodium hydride or potassium tert-butoxide) to the reaction mixture to give the desired isoquinolinones (method A).

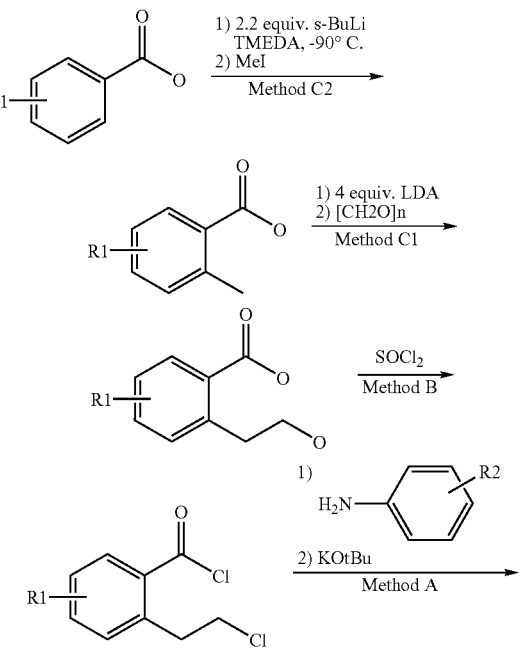

Scheme 1

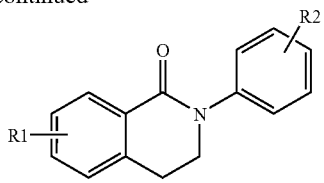

Alternatively, isoquinolinones can be obtained from 2-(2-hydroxyethyl)benzoic acids via the routes shown in scheme 1A. Treatment of the 2-(2-hydroxyethyl)benzoic acids with acid affords the corresponding isochromanones which can undergo a benzylic bromination by treatment for example with N-bromosuccinimide (NBS) and can subsequently be converted into the corresponding isochromenone by treatment for example with triethylamine. Trimethylaluminum-catalyzed opening of the isochromanones with aromatic amines leads to 2-(2-hydroxyethyl)benzanilides which can on the one hand be converted into dihydroisoquinolnones by converting the alcohol function into a leaving group (e.g. mesylate) and subsequent base treatment. A further possibility is for the 2-(2-hydroxyethyl)benzanilides first to be oxidized with oxidizing agents such as, for example, Dess-Martin reagent and subsequently converted by treatment with acid into isoquinolinones. Trimethylaluminum-mediated reaction of isochromenones with aromatic amides is also possible. Working up with acid leads directly to isoquinolinones (method K). dihydroisoquinolinones can be prepared from isoquinolinones by hydrogenation.

In a further variant for synthesizing isoquinolinones (scheme 1b), 2-methylbenzoic acids can be reacted with aromatic amines initially by one of the diverse methods for forming amide linkages (for example via the acid chloride or TOTU-mediated) to give 2-methylbenzanilides. These can then be doubly deprotonated with a strong base (for example lithium 2,2,6,6-tetramethylpiperidide (LTMP)) and reacted with acylating reagents (for example N-formylmorpholine or N-methoxy-N-methylacetamide). Final treatment with acid affords the desired isoquinolinones.

Scheme 1b

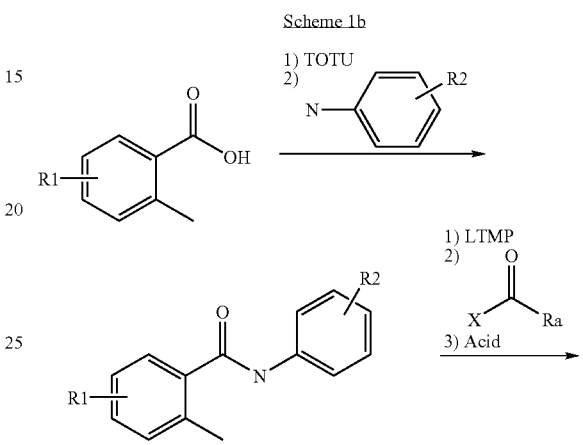

Scheme 1a

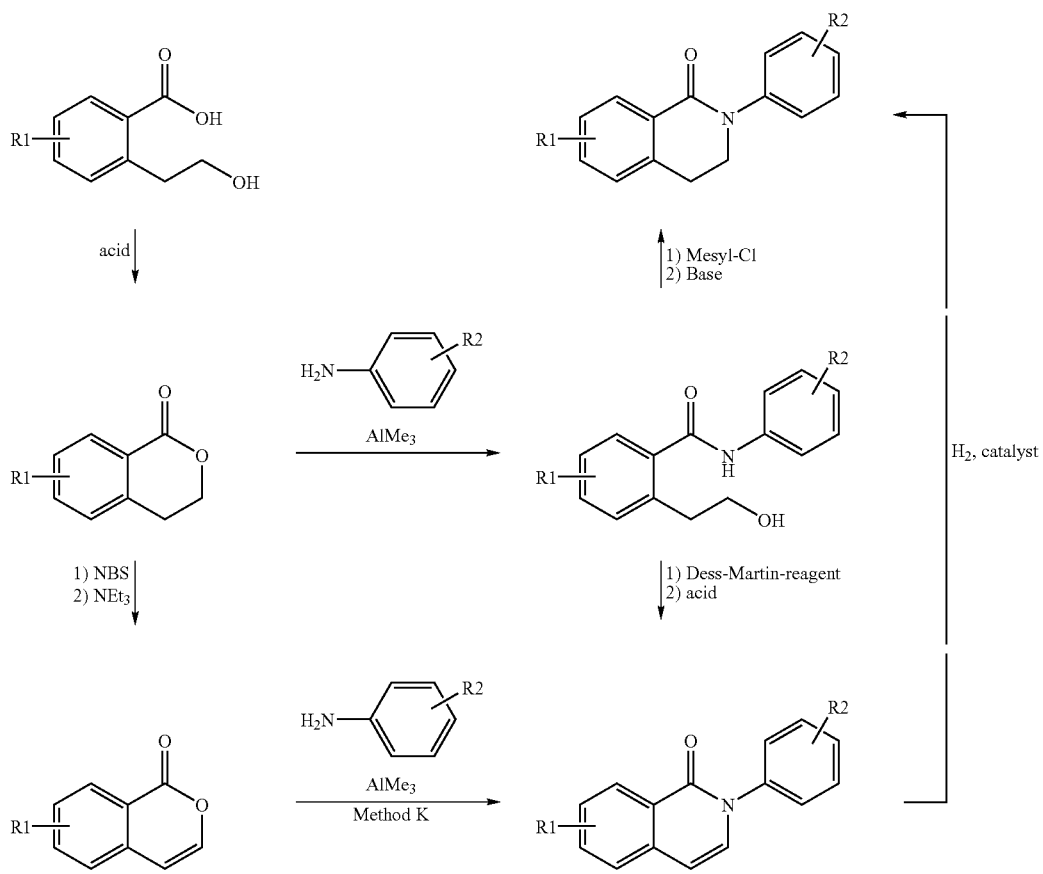

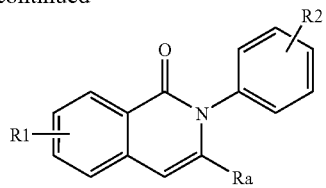

In a further novel variant for synthesizing isoquinolinones, 3-hydroxyisochroman-1-ones, which may also be in the form of 2-(2-oxoethyl)benzoic acids, can be reacted at elevated temperature with aromatic amines (scheme 1c). 3-Hydroxy-isochroman-1-ones can be obtained for example by oxidizing appropriate precursors containing the indane structure.

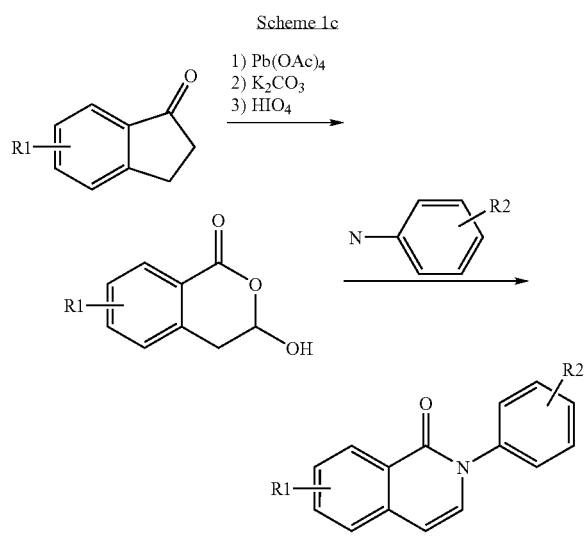

The required substituted aromatic amines can be obtained by nucleophilic substitution with aminoalcohols on suitable fluoronitrobenzenes (method E) and subsequent reduction of the nitro group (methods D and F respectively) (scheme 2).

PG therein is a group which is present 0-2 times according to the topology of the aminoalcohol and is generally unreactive under the conditions of methods E, F and D. Examples include alkyl groups and carbamates.

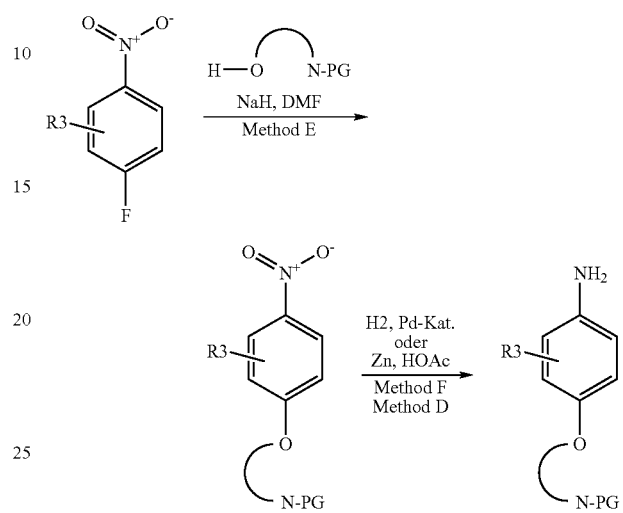

The N-PG group can be modified in diverse ways by known methods. For example, elimination of the protective group PG can be followed by alkylations e.g. with alkyl halides, epoxides or in the manner of a reductive alkylation with aldehydes or ketones.

Variation of the substitution on the dihydroisoquinolinone structure is possible inter alia also by modification of functional groups (scheme 3). Thus, for example, ethers can be cleaved (method H) and the resulting OH group be reacted with various alkylating agents (method G). After conversion of the OH group into a trifluoromethanesulfonate it is possible to carry out normal substitution reactions by nucleophiles, e.g. with transition metal catalysts (methods I and J).

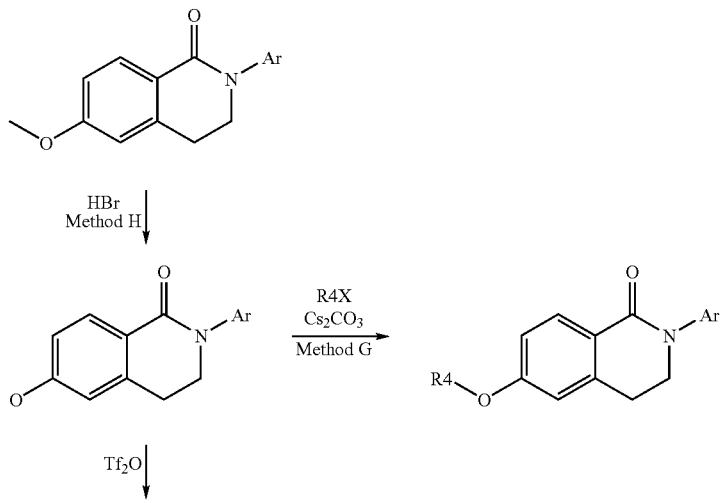

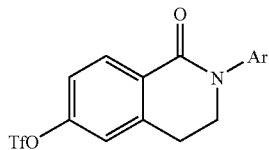 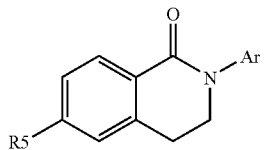

-continued

R5-B(OR)$_2$
Suzuki-Bed.
Method J

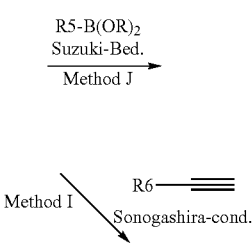

Method I, R6—≡, Sonogashira-cond.

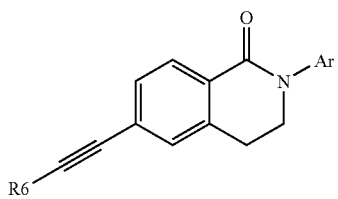

Descriptions of the general methods used are described by way of example in the following places:
Method A, B, C1, C2, D, E in example 1;
Method F according to table 1;
Method G, H in example 13;
Method I in example 29;
Method J in example 51;
Method K, L, M, N, O in example 56;
Method P, Q according to table 5:
Method R in example 82;
Method S, T, U, V in example 83.

General Explanations a) Mode of Drawing the Structural Formulae

Only non-hydrogen atoms are depicted for clarity in the structural formulae of the given examples.

b) Salt Forms

Many of the compounds of the invention are bases and can form salts with appropriately strong acids. The compounds can in particular be in the form of hydrotrifluoroacetates after purification by HPLC chromatography using a mobile phase containing trifluoroacetic acid. These can be converted into the free bases shown by simple treatment of a solution of the salts for example with sodium carbonate solution.

c) Units of the Characterizing Data

The unit of the indicated molecular weights is "g/mol". Peaks observed in the mass spectrum are stated as integral quotient of the molar molecular ion mass and the charge of the molecular ion (m/z).

Example 1

6-Butoxy-2-[3-chloro-4-((1R,3R,5S)-8-methyl-8-azabicyclo[3.2.1]oct-3-yloxy)-phenyl]-3,4-dihydro-2H-isoquinolin-1-one

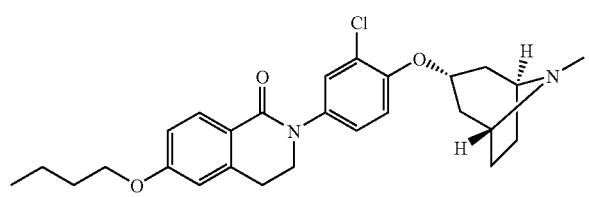 [SMILES: CCCCOc1ccc2c(c1)CCN(c1ccc(O[C@H]3C[C@H]4CC[C@@H](C3)N4C)c(Cl)c1)C2=O]

Method A

A solution of 3-chloro-4-((1R,3R,5S)-8-methyl-8-azabicyclo[3.2.1]oct-3-yloxy)phenylamine (97 mg) in THF (3 mL) was added dropwise to a solution of 4-butoxy-2-(2-chloroethyl)benzoyl chloride (100 mg) in THF (4 mL). Sodium hydride (55% in oil; 40 mg) was added to the resulting suspension and heated at 60° C. for 3 hours. An alternative possibility is also to employ potassium tert-butoxide as base at room temperature. After cooling, the precipitate was removed by filtration and the filtrate was concentrated. The residue was purified by preparative HPLC. The product with the molecular weight of 469.03 (C27H33ClN2O3) was obtained in this way; MS (ESI): 469 (M+H+).

Method B

4-Butoxy-2-(2-chloroethyl)benzoyl chloride

Thionyl chloride (5 g) was cooled to −10° C., and 4-butoxy-2-(2-hydroxyethyl)benzoic acid (1.0 g) was added in portions so that the internal temperature did not rise above −3° C. After 20 minutes at 0° C., the mixture was heated to reflux for 4 hours. Volatiles were removed in a rotary evaporator, and the residue was mixed twice with toluene (20 mL) and re-evaporated. The resulting oil was reacted further without further purification.

Method C1

Butoxy-2-(2-hydroxyethyl)benzoic acid

A solution of 4-butoxy-2-methylbenzoic acid (2.5 g) in THF (15 mL) was added dropwise to a solution of LDA (freshly prepared from diisopropylamine (4.86 g) and n-butyllithium (32 mL; 1.5 M in hexane)) in THF (50 mL) at −78° C. After 10 minutes, paraformaldehyde (1.44 g) was added, and the mixture was allowed slowly to warm to room temperature. After 4 hours, water (10 mL) was added, and the volatile organic constituents were removed in a rotary evaporator. The residue was partitioned between water and diethyl ether. The aqueous phase was mixed with dichloromethane and cautiously acidified with hydrochloric acid at 0° C. Concentration of the organic phase afforded the desired product with the molecular weight of 238.29 (C13H18O4); MS (ESI): 239 (M+H+).

Method C2

Butoxy-2-methylbenzoic acid

A mixture of 4-butoxybenzoic acid (10 g), N,N,N',N'-tetramethylethylenediamine (13.2 g) and THF (75 mL) was cooled to −90° C., and sec-butyllithium (81 mL; 1.4 M in hexane) was added over the course of 30 minutes. After a further 30 minutes, the mixture was warmed to −78° C., and a solution of methyl iodide (12.8 mL) in THF (10 mL) was added dropwise. The reaction solution was allowed to warm to room temperature and the mixture was hydrolyzed with water and extracted with ethyl acetate. The organic phase was dried over magnesium sulfate and concentrated. The residue was purified by chromatography on silica gel. The product with the molecular weight of 208.26 (C12H16O3) was obtained in this way; MS (ESI): 209 (M+H+).

Method D

3-Chloro-4-((1R,3R,5S)-8-methyl-8-azabicyclo[3.2.1]oct-3-yloxy)phenylamine

Zinc powder (3.0 g) was added in portions to a solution of (1R,3R,5S)-3-(2-chloro-4-nitrophenoxy)-8-methyl-8-azabicyclo[3.2.1]octane (2.1 g) in glacial acetic acid (50 mL) cooled to 0° C. After the addition was complete, the mixture was stirred at room temperature for 30 minutes and then insolubles were filtered off with suction. The filtrate was concentrated in a rotary evaporator, and the residue was partitioned between sodium hydroxide solution and ethyl acetate. The organic phase was dried over magnesium sulfate and concentrated. The product with the molecular weight of 266.77 (C14H19ClN2O) was obtained in this way; MS (ESI): 267 (M+H+).

Method E (1R,3R,5S)-3-(2-Chloro-4-nitrophenoxy)-8-methyl-8-azabicyclo[3.2.1]octane Sodium hydride (55% in oil; 1.05 g) was added in portions to a mixture of tropine (3.06 g) and DMF (50 mL). After gas evolution ceased, 3-chloro-4-fluoronitrobenzene (4.0 g) was added and the mixture was heated at 50° C. for 8 hours. The cooled reaction mixture was cautiously hydrolyzed with water and extracted with ethyl acetate. The organic phase was dried over magnesium sulfate and concentrated. The product with the molecular weight of 296.76 (C14H17ClN2O3) was obtained in this way; MS (ESI): 297 (M+H+).

The exemplary compounds in table 1 were obtained by method A from 4-butoxy-2-(2-chloroethyl)benzoyl chloride or 4-methoxy-2-(2-chlorethyl)benzoyl chloride and the appropriate anilines.

TABLE 1

| EX. No. | Structure | Molecular formula | Molecular weight | ESI-MS [M + H]+ |
|---|---|---|---|---|
| 2 | | C23H30N2O3 | 382.51 | 383 |
| 3 | | C25H31FN2O3 | 426.54 | 427 |
| 4 | | C27H33FN2O3 | 452.57 | 453 |
| 5 | | C26H33N3O3 | 435.57 | 436 |
| 6 | | C26H34N2O4 | 438.57 | 439 |

TABLE 1-continued

| EX. No. | | Molecular formula | Molecular weight | ESI-MS [M + H]+ |
|---|---|---|---|---|
| 7 | 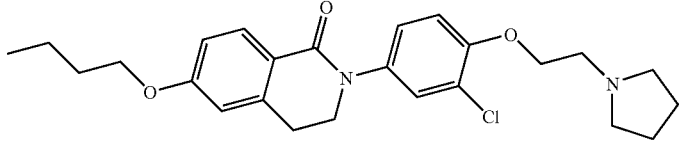 [SMILES: CCCCOc1ccc2c(c1)CCN(c1ccc(OCCN3CCCC3)c(Cl)c1)C2=O] | C25H31ClN2O3 | 442.99 | 443 |
| 8 | 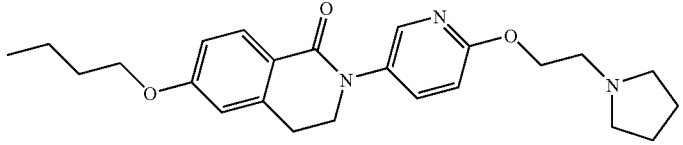 [SMILES: CCCCOc1ccc2c(c1)CCN(c1ccc(OCCN3CCCC3)nc1)C2=O] | C24H31N3O3 | 409.53 | 410 |
| 9 | 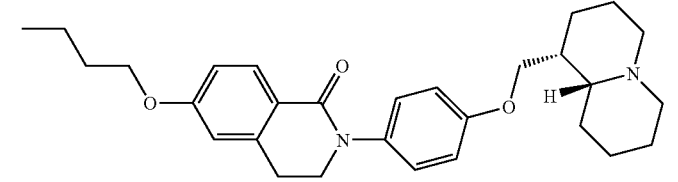 [SMILES: CCCCOc1ccc2c(c1)CCN(c1ccc(OC[C@@H]3CCCN4CCCC[C@H]34)cc1)C2=O] | C29H38N2O3 | 462.64 | 463 |
| 10 | 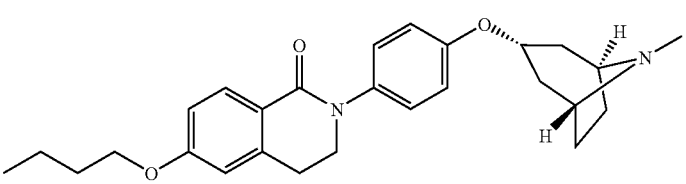 [SMILES: CCCCOc1ccc2c(c1)CCN(c1ccc(O[C@H]3C[C@H]4CC[C@@H](C3)N4C)cc1)C2=O] | C27H34N2O3 | 434.58 | 435 |
| 11 | 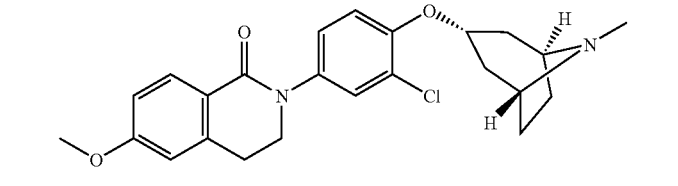 | C24H27ClN2O3 | 426.95 | 427 |
| 12 | 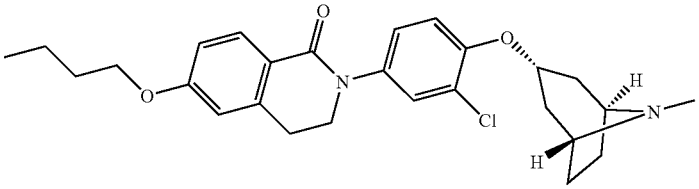 [SMILES: CCCCOc1ccc2c(c1)CCN(c1ccc(O[C@H]3C[C@H]4CC[C@@H](C3)N4C)c(Cl)c1)C2=O] | C27H33ClN2O3 | 469.03 | 469 |

4-Methoxy-2-(2-chloroethyl)benzoyl chloride

4-Methoxy-2-methylbenzoic acid was firstly reacted with paraformaldehyde by method C, and the product was then reacted with thionyl chloride by method B.

Method F

3-Fluoro-4-((1R,3R,5S)-8-methyl-8-azabicyclo[3.2.1]oct-3-yloxy)phenylamine

A suspension of (1R,3R,5S)-3-(2-fluoro-4-nitrophenoxy)-8-methyl-8-azabicyclo[3.2.1]octane (3.0 g) and palladium (II) hydroxide (20% on carbon; 0.9 g) in ethanol (150 mL) was vigorously stirred under a hydrogen atmosphere (atmospheric pressure) for 3 hours. The catalyst was then removed by filtration and the filtrate was concentrated. The product with the molecular weight of 250.32 (C14H19FN2O) was obtained in this way; MS (ESI): 251 (M+H+). It is possible as alternative to use 5% or 10% palladium on carbon as catalyst. (1R,3R,5S)-3-(2-Fluoro-4-nitro-phenoxy)-8-methyl-8-azabicyclo[3.2.1]octane was obtained by method E from 1,2-difluoro-4-nitro-benzene and tropine.

The following anilines were prepared analogously by method E and F:

4-(2-dimethylaminoethoxy)phenylamine;

3-fluoro-4-(2-pyrrolidin-1-yl-ethoxy)phenylamine;

6-(2-pyrrolidin-1-yl-ethoxy)pyridin-3-ylamine;

4-[(1R,9aR)-1-(octahydroquinolizin-1-yl)methoxy]phenylamine;

6-((1R,3R,5S)-8-methyl-8-azabicyclo[3.2.1]oct-3-yloxy)pyridin-3-ylamine (from tropine and 2-bromo-5-nitro-pyridine);

4-((1R,3R,5S)-8-methyl-8-azabicyclo[3.2.1]oct-3-yloxy)phenylamine;

3-methoxy-4-(2-pyrrolidin-1-yl-ethoxy)phenylamine (1-[2-(2-Methoxy-4-nitrophenoxy)ethyl]pyrrolidine was prepared by alkylation of 2-methoxy-4-nitrophenol with 1-(2-chloroethyl)pyrrolidine).

3-Chloro-4-((1R,3S,5S)-8-methyl-8-azabicyclo[3.2.1]oct-3-yloxy)phenylamine was obtained by reduction of ((1R,3S,5S)-3-(2-chloro-4-nitrophenoxy)-8-methyl-8-azabicyclo[3.2.1]octane with zinc by method D.

((1R,3S,5S)-3-(2-Chloro-4-nitrophenoxy)-8-methyl-8-azabicyclo[3.2.1]octane

A solution of 2-chloro-4-nitrophenol (3.0 g) and tropine (2.69 g) in dichloromethane (100 μL) was mixed with triphenylphosphine (polymer; 6.8 g), and then di-tert-butyl azodicarboxylate (4.78 g) was added dropwise. After stirring at room temperature for 12 hours, the polymer was filtered off with suction and the filtrate was concentrated. The residue was purified by preparative HPLC. The product with the molecular weight of 266.77 (C14H19ClN2O) was obtained in this way; MS (ESI): 267 (M+H+).)

Reaction of the appropriate starting materials by method E and D resulted in 3-chloro-4-(2-pyrrolidin-1-ylethoxy)phenylamine.

Example 13

2-[3-Chloro-4-((1R,3R,5S)-8-methyl-8-azabicyclo[3.2.1]oct-3-yloxy)phenyl]-6-propoxy-3,4-dihydro-2H-isoquinolin-1-one

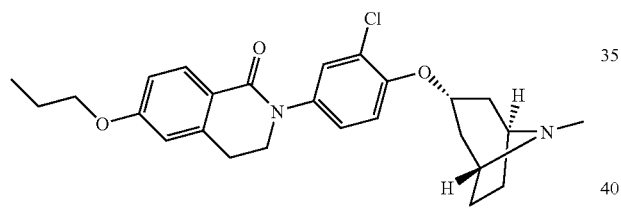

Method G

Sodium hydride (55% strength in oil; 5.3 mg) was added to a solution of 2-[3-chloro-4-((1R,3R,5S)-8-methyl-8-azabicyclo[3.2.1]oct-3-yloxy)phenyl]-6-hydroxy-3,4-dihydro-2H-isoquinolin-1-one (50 mg) in NMP (2 mL). After gas evolution ceased, 1-iodopropane (21 mg) was added. After 12 hours, the reaction mixture was cautiously hydrolyzed with water and extracted with ethyl acetate. The organic phase was concentrated and purified by preparative HPLC. The product with the molecular weight of 455.00 (C26H31ClN2O3) was obtained in this way; MS (ESI): 455 (M+H+). An alternative possibility is also to use alkali metal carbonates (e.g. potassium carbonate or cesium carbonate) or triethylamine as base, and DMF as solvent. Furthermore, alkyl bromides can also be used.

Method H

2-[3-Chloro-4-((1R,3R,5S)-8-methyl-8-azabicyclo[3.2.1]oct-3-yloxy)phenyl]-6-hydroxy-3,4-dihydro-2H-isoquinolin-1-one A solution of 2-[3-chloro-4-((1R,3R,5S)-8-methyl-8-azabicyclo[3.2.1]oct-3-yloxy)phenyl]-6-methoxy-3,4-dihydro-2H-isoquinolin-1-one (4.0 g) in hydrobromic acid (48% strength in water; 40 mL) was heated at 100° C. for 20 hours. Volatiles were evaporated off, and the residue was suspended in water/methanol (600/400 mL) and heated to 70° C. The pH was adjusted to 10.3 by adding saturated sodium carbonate solution. The mixture was cooled to room temperature, and the precipitate was isolated by filtration and washing with methanol. The product with the molecular weight of 412.92 (C23H25ClN2O3) was obtained in this way; MS (ESI): 413 (M+H+).

Alkylation of 2-[3-chloro-4-((1R,3R,5S)-8-methyl-8-azabicyclo[3.2.1]oct-3-yloxy)phenyl]-6-hydroxy-3,4-dihydro-2H-isoquinolin-1-one or 6-hydroxy-2-[3-methoxy-4-(2-pyrrolidin-1-ylethoxy)phenyl]-3,4-dihydro-2H-isoquinolin-1-one by method G resulted in the exemplary compounds in table 2.

TABLE 2

| EX. No. | Structure | Molecular formula | Molecular weight | ESI-MS [M + H]+ |
|---|---|---|---|---|
| 14 | 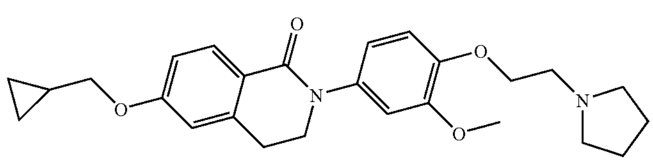 [SMILES: COc1cc(N2CCc3cc(OCC4CC4)ccc3C2=O)ccc1OCCN1CCCC1] | C26H32N2O4 | 436.56 | 437 |
| 15 | 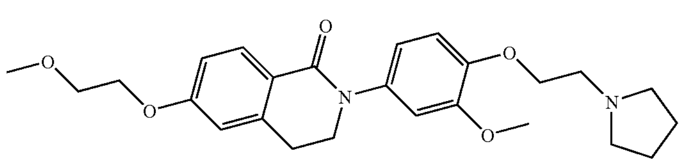 [SMILES: COCCOc1ccc2c(c1)CCN(c1ccc(OCCN3CCCC3)c(OC)c1)C2=O] | C25H32N2O5 | 440.54 | 441 |

TABLE 2-continued
| EX. No. | Structure | Molecular formula | Molecular weight | ESI-MS [M + H]+ |
|---|---|---|---|---|
| 16 | 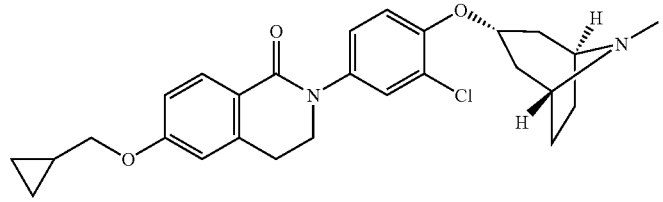 [SMILES: CN1[C@@H]2CC[C@H]1C[C@@H](Oc1ccc(N3CCc4cc(OCC5CC5)ccc4C3=O)cc1Cl)C2] | C27H31ClN2O3 | 467.01 | 467 |
| 17 | 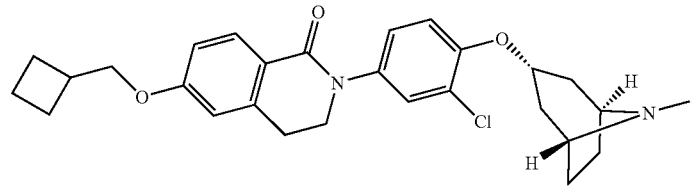 [SMILES: CN1[C@@H]2CC[C@H]1C[C@@H](Oc1ccc(N3CCc4cc(OCC5CCC5)ccc4C3=O)cc1Cl)C2] | C28H33ClN2O3 | 481.04 | 481 |
| 18 | 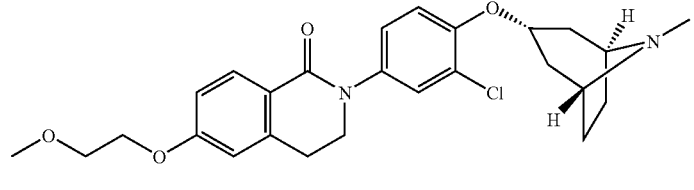 | C26H31ClN2O4 | 471.00 | 471 |
| 19 | 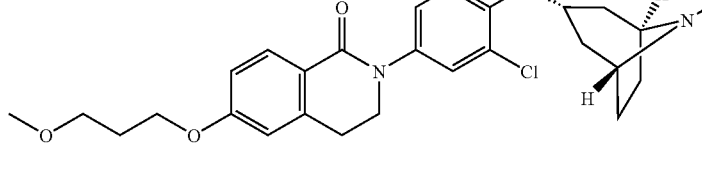 | C27H33ClN2O4 | 485.03 | 485 |
| 20 | 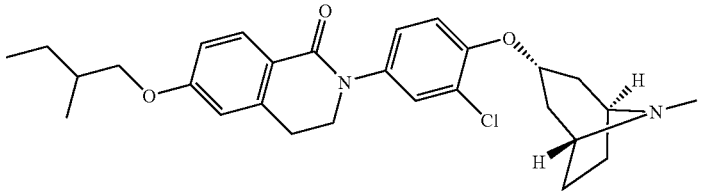 [SMILES: CCC(C)COc1ccc2c(c1)CCN(c1ccc(O[C@H]3C[C@H]4CC[C@@H](C3)N4C)c(Cl)c1)C2=O] | C28H35ClN2O3 | 483.06 | 483 |
| 21 | 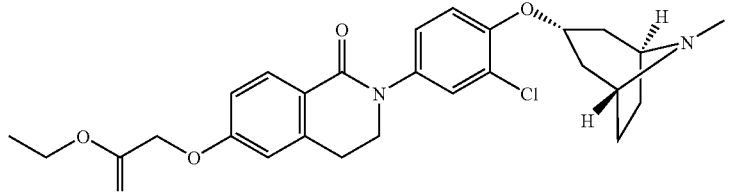 | C27H31ClN2O5 | 499.01 | 499 |
| 22 | 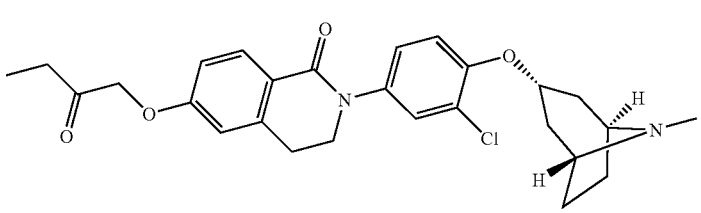 [SMILES: CCC(=O)COc1ccc2c(c1)CCN(c1ccc(O[C@H]3C[C@H]4CC[C@@H](C3)N4C)c(Cl)c1)C2=O] | C27H31ClN2O4 | 483.01 | 483 |

TABLE 2-continued

| EX. No. | Structure | Molecular formula | Molecular weight | ESI-MS [M + H]+ |
|---|---|---|---|---|
| 23 | 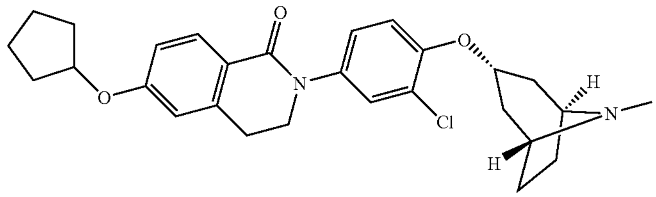 [SMILES: CN1[C@@H]2CC[C@H]1C[C@@H](Oc1ccc(N3CCc4cc(OC5CCCC5)ccc4C3=O)cc1Cl)C2] | C28H33ClN2O3 | 481.04 | 481 |
| 24 | 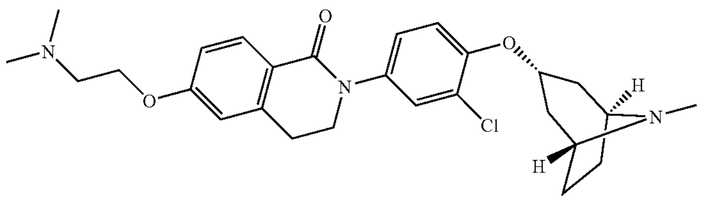 | C27H34ClN3O3 | 484.04 | 484 |
| 25 | 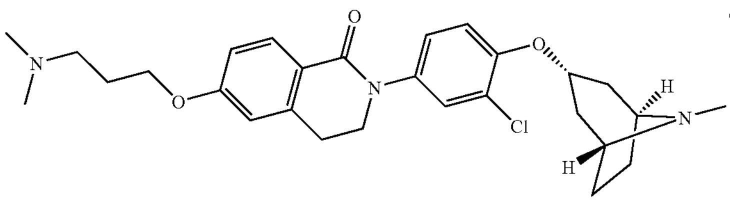 | C28H36ClN3O3 | 498.07 | 498 |

6-Hydroxy-2-[3-methoxy-4-(2-pyrrolidin-1-ylethoxy)phenyl]-3,4-dihydro-2H-isoquinolin-1-one Hydrogenation of 6-benzyloxy-2-[3-methoxy-4-(2-pyrrolidin-1-ylethoxy)phenyl]-3,4-dihydro-2H-isoquinolin-1-one under the conditions indicated in method F afforded the product with the molecular weight of 382.46 (C22H26N2O4); MS (ESI): 383 (M+H+). 6-Benzyloxy-2-[3-methoxy-4-(2-pyrrolidin-1-ylethoxy)phenyl]-3,4-dihydro-2H-isoquinolin-1-one was prepared from 4-benzyloxy-2-methylbenzoic acid and 3-methoxy-4-(2-pyrrolidin-1-ylethoxy)phenylamine by method C, B and A.

4-Benzyloxy-2-methylbenzoic acid

A solution of 4-benzyloxy-2-methylbenzaldehyde (20 g) in 1,4-dioxane (300 mL) was mixed with sodium dihydrogen phosphate (42.4 g) and sulfamic acid (13.7 g) and, while cooling, a solution of sodium chlorite (11.2 g) in water (200 mL) was added in such a way that the temperature did not rise above 10° C. After 20 minutes, sodium sulfite (14.5 g) was added, and the mixture was stirred at 10° C. for a further 15 minutes. The reaction mixture was acidified with hydrochloric acid and extracted with ethyl acetate. The organic phase was dried over magnesium sulfate and concentrated.

The product with the molecular weight of 242.28 (C15H14O3) was obtained in this way; MS (ESI): 243 (M+H+).

Example 26

2-[3-Chloro-4-((1R,3R,5S)-8-methyl-8-azabicyclo [3.2.1]oct-3-yloxy)phenyl]-6-(thietan-3-yloxy)-3,4-dihydro-2H-isoquinolin-1-one

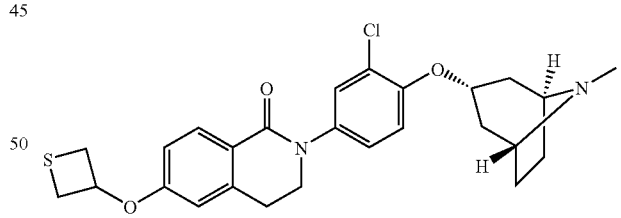

Sodium hydroxide solution (2M; 0.375 mL) and 2-chloromethylthiirane (35 mg) were added to a mixture of 2-[3-chloro-4-((1R,3R,5S)-8-methyl-8-azabicyclo[3.2.1]oct-3-yloxy)phenyl]-6-hydroxy-3,4-dihydro-2H-isoquinolin-1-one (hydrobromide; 100 mg), ethanol (0.9 mL) and water (1 mL). The mixture was heated at 50-60° C. for 3 hours. Then sodium hydroxide solution (2M; 0.15 mL) and 2-chloromethylthiirane (35 mg) were again added. This procedure was repeated three more times. The reaction solution was concentrated. The residue was purified by preparative HPLC. The product with the molecular weight of 485.05 (C26H29ClN2O3S) was obtained in this way; MS (ESI): 485 (M+H+).

Example 27

2-[3-Chloro-4-((1R,3R,5S)-8-methyl-8-azabicyclo[3.2.1]oct-3-yloxy)phenyl]-6-(1-oxo-1lambda*4*-thietan-3-yloxy)-3,4-dihydro-2H-isoquinolin-1-one

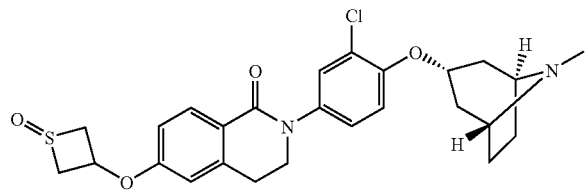 [SMILES: CN1[C@@H]2CC[C@H]1C[C@@H](Oc1ccc(N3CCc4cc(OC5CS(=O)C5)ccc4C3=O)cc1Cl)C2]

Hydrogen chloride (4M in dioxane; 1 mL) was added to a solution of 2-[3-chloro-4-((1R,3R,5S)-8-methyl-8-azabicyclo[3.2.1]oct-3-yloxy)phenyl]-6-(thietan-3-yloxy)-3,4-dihydro-2H-isoquinolin-1-one (52 mg) in ethanol (2 mL), and volatiles were removed. The residue was suspended in ethanol (0.5 mL), and a solution of sodium metaperiodate (34.4 mg) in water (0.32 mL) was added. After 18 hours, half of the reaction solution was concentrated. The residue was purified by preparative HPLC. The product with the molecular weight of 501.05 (C26H29ClN2O4S) was obtained in this way; MS (ESI): 501 (+H+).

Example 28

2-[3-Chloro-4-((1R,3R,5S)-8-methyl-8-azabicyclo[3.2.1]oct-3-yloxy)phenyl]-6-(1,1-dioxo-1lambda*6*-thietan-3-yloxy)-3,4-dihydro-2H-isoquinolin-1-one

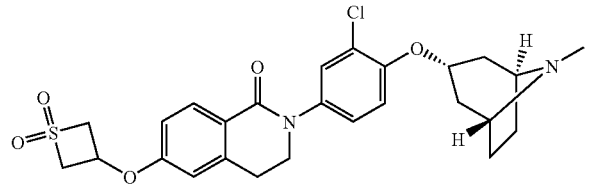 [SMILES: CN1[C@@H]2CC[C@H]1C[C@@H](Oc1ccc(N3CCc4cc(OC5CS(=O)(=O)C5)ccc4C3=O)cc1Cl)C2]

The second half of the reaction solution from example 27 was mixed with Oxone (potassium monopersulfate triple salt; 39.5 mg), and the mixture was left to stand for 48 hours. The reaction solution was concentrated. The residue was purified by preparative HPLC. The product with the molecular weight of 517.05 (C26H29ClN2O5S) was obtained in this way; MS (ESI): 517 (M+H+).

Example 29

2-[3-Chloro-4-((1S,3R,5R)-8-methyl-8-azabicyclo[3.2.1]oct-3-yloxy)phenyl]-6-(3-hydroxy-4-methylpent-1-ynyl)-3,4-dihydro-2H-isoquinolin-1-one

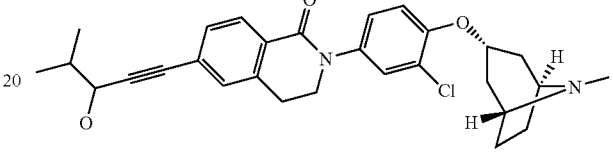

Method I

4-Methylpent-1-yn-3-ol (36 mg), triphenylphosphine (9.6 mg), cesium carbonate (120 mg), bis(triphenylphosphine)palladium(II) chloride (6.4 mg) and copper(I) iodide (7.0 mg) were successively added to a solution of trifluoromethanesulfonic acid 2-[3-chloro-4-((1S,3R,5R)-8-methyl-8-azabicyclo[3.2.1]oct-3-yloxy)phenyl]-1-oxo-1,2,3,4-tetrahydroisoquinolin-6-yl ester (100 mg) in NMP (2 mL). The mixture was heated at 85° C. for 3 hours. The reaction solution was concentrated. The residue was purified by preparative HPLC. The product with the molecular weight of 493.05 (C29H33ClN2O3) was obtained in this way; MS (ESI): 493 (M+H+).

Trifluoromethanesulfonic acid 2-[3-chloro-4-((1S,3R,5R)-8-methyl-8-azabicyclo[3.2.1]oct-3-yloxy)phenyl]-1-oxo-1,2,3,4-tetrahydroisoquinolin-6-yl ester Trifluoromethanesulfonic anhydride (0.58 mL) was added to a solution of 2-[3-chloro-4-((1S,3R,5R)-8-methyl-8-azabicyclo[3.2.1]oct-3-yloxy)phenyl]-6-hydroxy-3,4-dihydro-2H-isoquinolin-1-one (0.8 g) and pyridine (0.31 mL) in dichloromethane (50 mL) at 0° C. After 30 minutes, the mixture was partitioned between water and dichloromethane, and the organic phase was dried over magnesium sulfate and concentrated. The product with the molecular weight of 544.98 (C24H24ClF3N2O5S) was obtained in this way; MS (ESI): 545 (M+H+).

Reaction of trifluoromethanesulfonic acid 2-[3-chloro-4-((1S,3R,5R)-8-methyl-8-azabicyclo[3.2.1]oct-3-yloxy)phenyl]-1-oxo-1,2,3,4-tetrahydroisoquinolin-6-yl ester with the appropriate alkynes by method I resulted in the exemplary compounds in table 3.

TABLE 3

| EX. No. | Structure | Molecular formula | Molecular weight | ESI-MS [M + H]+ |
|---|---|---|---|---|
| 30 | 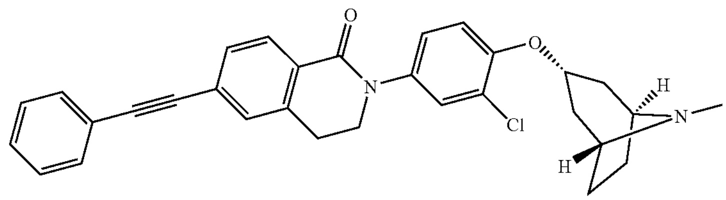 [SMILES: CN1[C@@H]2CC[C@H]1C[C@@H](Oc1ccc(N3CCc4cc(C#Cc5ccccc5)ccc4C3=O)cc1Cl)C2] | C31H29ClN2O2 | 497.04 | 497 |
| 31 | 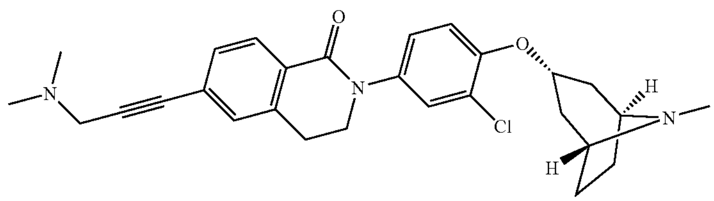 | C28H32ClN3O2 | 478.04 | 478 |
| 32 | 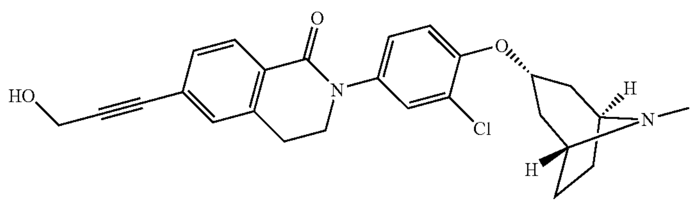 [SMILES: CN1[C@@H]2CC[C@H]1C[C@@H](Oc1ccc(N3CCc4cc(C#CCO)ccc4C3=O)cc1Cl)C2] | C26H27ClN2O3 | 450.97 | 451 |
| 33 | 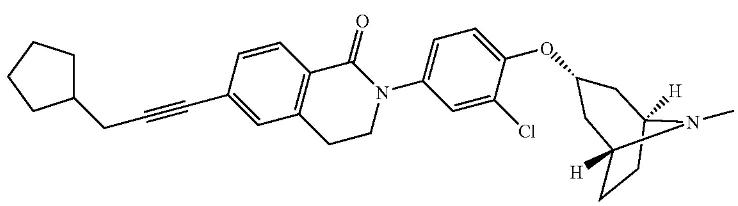 [SMILES: CN1[C@@H]2CC[C@H]1C[C@@H](Oc1ccc(N3CCc4cc(C#CCC5CCCC5)ccc4C3=O)cc1Cl)C2] | C31H35ClN2O2 | 503.09 | 503 |
| 34 | 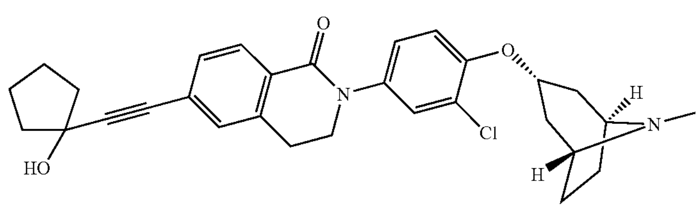 [SMILES: CN1[C@@H]2CC[C@H]1C[C@@H](Oc1ccc(N3CCc4cc(C#CC5(O)CCCC5)ccc4C3=O)cc1Cl)C2] | C30H33ClN2O3 | 505.06 | 505 |
| 35 | 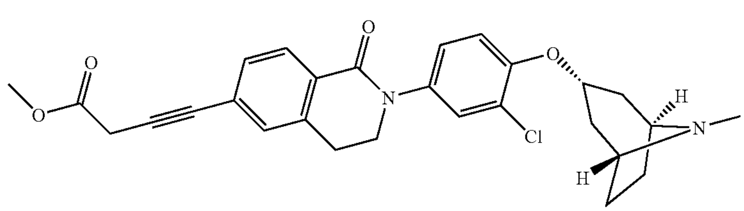 | C28H29ClN2O4 | 493.01 | 493 |
| 36 | 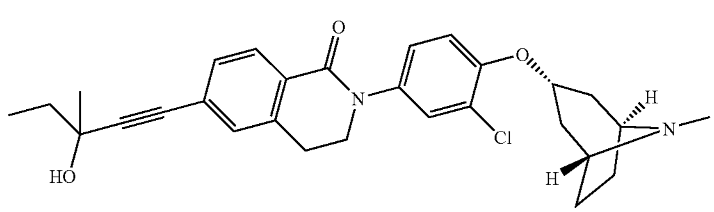 [SMILES: CCC(C)(O)C#Cc1ccc2c(c1)CCN(c1ccc(O[C@H]3C[C@H]4CC[C@@H](C3)N4C)c(Cl)c1)C2=O] | C29H33ClN2O3 | 493.05 | 493 |

TABLE 3-continued

| EX. No. | Structure | Molecular formula | Molecular weight | ESI-MS [M + H]+ |
|---|---|---|---|---|
| 37 | 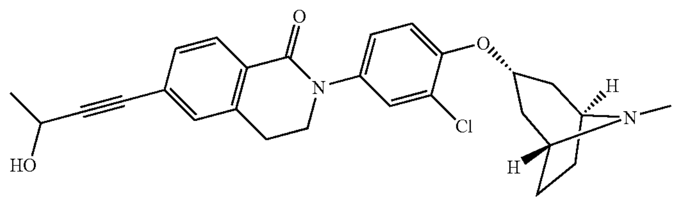 [SMILES: CC(O)C#Cc1ccc2c(c1)CCN(c1ccc(O[C@H]3C[C@H]4CC[C@@H](C3)N4C)c(Cl)c1)C2=O] | C27H29ClN2O3 | 465.00 | 465 |
| 38 | 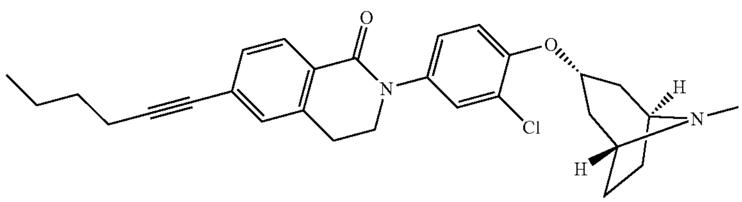 [SMILES: CCCCC#Cc1ccc2c(c1)CCN(c1ccc(O[C@H]3C[C@H]4CC[C@@H](C3)N4C)c(Cl)c1)C2=O] | C29H33ClN2O2 | 477.05 | 477 |
| 39 | 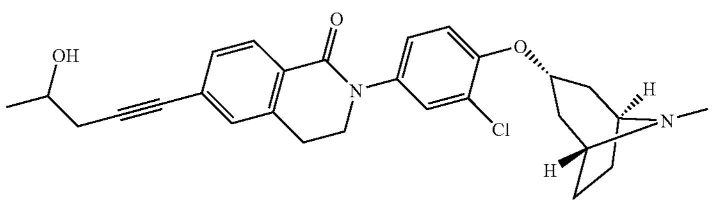 [SMILES: CC(O)CC#Cc1ccc2c(c1)CCN(c1ccc(O[C@H]3C[C@H]4CC[C@@H](C3)N4C)c(Cl)c1)C2=O] | C28H31ClN2O3 | 479.02 | 479 |
| 40 | 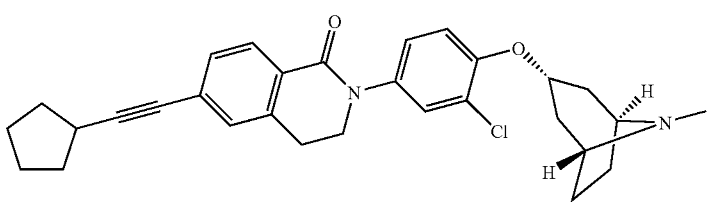 [SMILES: CN1[C@@H]2CC[C@H]1C[C@@H](Oc1ccc(N3CCc4cc(C#CC5CCCC5)ccc4C3=O)cc1Cl)C2] | C30H33ClN2O2 | 489.06 | 489 |
| 41 | 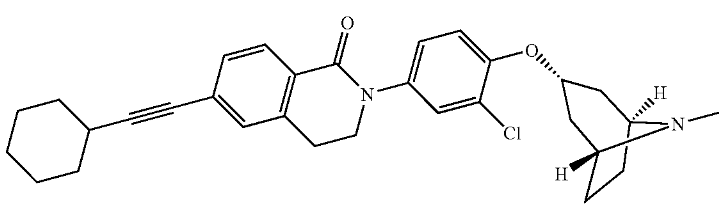 [SMILES: CN1[C@@H]2CC[C@H]1C[C@@H](Oc1ccc(N3CCc4cc(C#CC5CCCCC5)ccc4C3=O)cc1Cl)C2] | C31H35ClN2O2 | 503.09 | 503 |
| 42 | 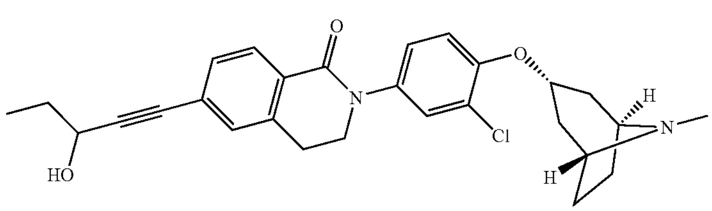 [SMILES: CCC(O)C#Cc1ccc2c(c1)CCN(c1ccc(O[C@H]3C[C@H]4CC[C@@H](C3)N4C)c(Cl)c1)C2=O] | C28H31ClN2O3 | 479.02 | 479 |
| 43 | 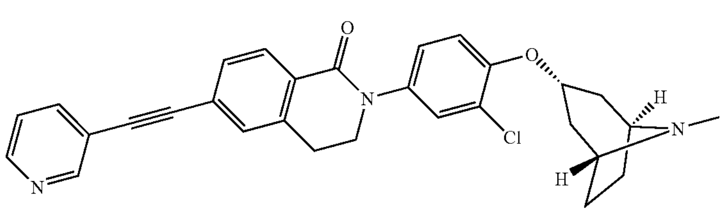 [SMILES: CN1[C@@H]2CC[C@H]1C[C@@H](Oc1ccc(N3CCc4cc(C#Cc5cccnc5)ccc4C3=O)cc1Cl)C2] | C30H28ClN3O2 | 498.03 | 498 |

TABLE 3-continued

| EX. No. | Structure | Molecular formula | Molecular weight | ESI-MS [M + H]+ |
|---|---|---|---|---|
| 44 | 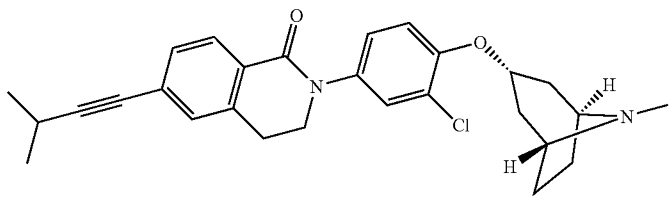 [SMILES: CC(C)C#Cc1ccc2c(c1)CCN(c1ccc(O[C@H]3C[C@H]4CC[C@@H](C3)N4C)c(Cl)c1)C2=O] | C28H31ClN2O2 | 463.02 | 463 |
| 45 | 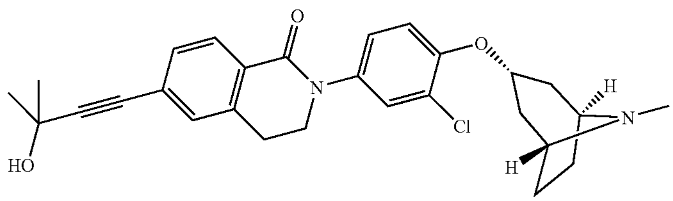 | C28H31ClN2O3 | 479.02 | 479 |
| 46 | 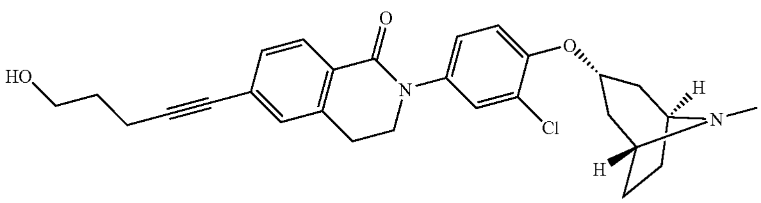 [SMILES: CN1[C@@H]2CC[C@H]1C[C@@H](Oc1ccc(N3CCc4cc(C#CCCCO)ccc4C3=O)cc1Cl)C2] | C28H31ClN2O3 | 479.02 | 479 |
| 47 | 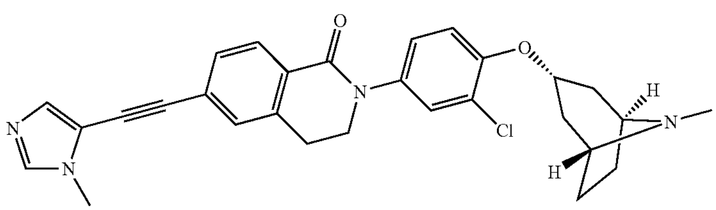 [SMILES: CN1[C@@H]2CC[C@H]1C[C@@H](Oc1ccc(N3CCc4cc(C#Cc5cncn5C)ccc4C3=O)cc1Cl)C2] | C29H29ClN4O2 | 501.03 | 501 |
| 48 | 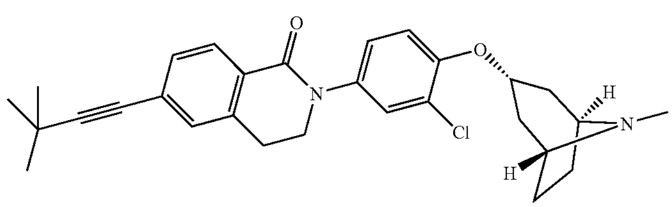 [SMILES: CN1[C@@H]2CC[C@H]1C[C@@H](Oc1ccc(N3CCc4cc(C#CC(C)(C)C)ccc4C3=O)cc1Cl)C2] | C29H33ClN2O2 | 477.05 | 477 |
| 49 | 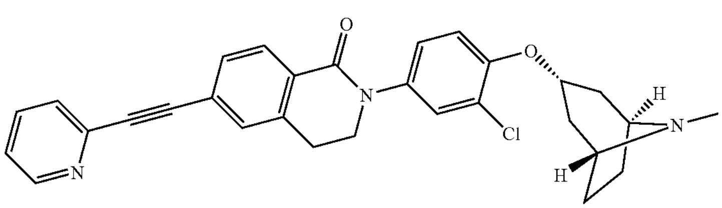 | C30H28ClN3O2 | 498.03 | 498 |
| 50 | 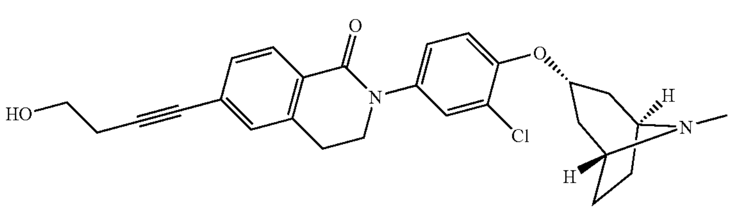 [SMILES: CN1[C@@H]2CC[C@H]1C[C@@H](Oc1ccc(N3CCc4cc(C#CCCO)ccc4C3=O)cc1Cl)C2] | C27H29ClN2O3 | 465.00 | 465 |

Example 51

2-[3-Chloro-4-((1S,3R,5R)-8-methyl-8-azabicyclo[3.2.1]oct-3-yloxy)phenyl]-6-phenyl-3,4-dihydro-2H-isoquinolin-1-one

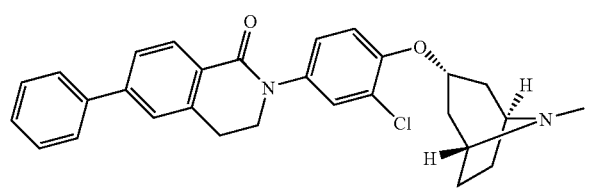 [SMILES: CN1[C@@H]2CC[C@H]1C[C@@H](Oc1ccc(N3CCc4cc(-c5ccccc5)ccc4C3=O)cc1Cl)C2]

Method J

Phenyl boronic acid (22.4 mg), cesium carbonate (60 mg) in water/ethanol (0.5 mL/0.5 mL) and tetrakis(triphenylphosphine)palladium (5.3 mg) were successively added to a solution of trifluoromethanesulfonic acid 2-[3-chloro-4-((1S,3R,5R)-8-methyl-8-azabicyclo[3.2.1]oct-3-yloxy)phenyl]-1-oxo-1,2,3,4-tetrahydroisoquinolin-6-yl ester (100 mg) in toluene (2 mL). The mixture was heated to reflux for 5 hours. After cooling, the organic phase was separated off and concentrated. The residue was purified by preparative HPLC. The product with the molecular weight of 473.02 (C29H29ClN2O2) was obtained in this way; MS (ESI): 473 (M+H+).

Reaction of trifluoromethanesulfonic acid 2-[3-chloro-4-((1S,3R,5R,)-8-methyl-azabicyclo[3.2.1]oct-3-ylocy)-phenyl]-1-oxo-1,2,3,4-tetrahydroisoquinolin-6-yl ester with the corresponding boronic acids by method J resulted in the exemplary compounds in table 4.

Example 55

6-[4-(2-Dimethylaminoethoxy)phenyl]-2-p-tolyl-5,6-dihydro-4H-thieno[2,3-c]pyridin-7-one

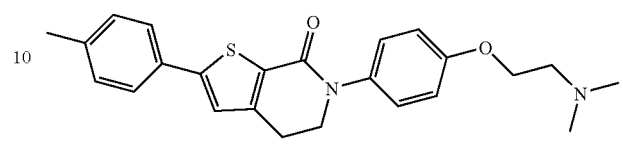

Firstly 3-methyl-5-p-tolylthiophene-2-carboxylic acid was reacted with paraformaldehyde by method C1, and then the product was treated with thionyl chloride by method B. The resulting dichloride was finally reacted with 4-(2-dimethylaminoethoxy)phenylamine by method A. The product with the molecular weight of 406.55 (C24H26N2O2S) was obtained in this way; MS (ESI): 407 (M+H+).

3-Methyl-5-p-tolylthiophene-2-carboxylic acid

A solution of 3-methyl-5-p-tolylthiophene-2-carbaldehyde (2.6 g) in 1,4-dioxane (30 mL) was mixed with a solution of sodium dihydrogenphosphate (5.77 g) in water, and sulfamic acid (1.87 g) was added. At 10° C., a solution of sodium chlorite (1.52 g) in water (20 mL) was added dropwise in such a way that the temperature did not rise above 10° C.

Twenty minutes after the addition was complete, sodium sulfite (1.98 g) was added and the mixture was stirred for 15 minutes. The reaction mixture was acidified with hydrochloric acid and extracted with ethyl acetate. The organic phase

TABLE 4

| EX. No. | Structure | Molecular formula | Molecular weight | ESI-MS [M + H]+ |
|---|---|---|---|---|
| 52 | 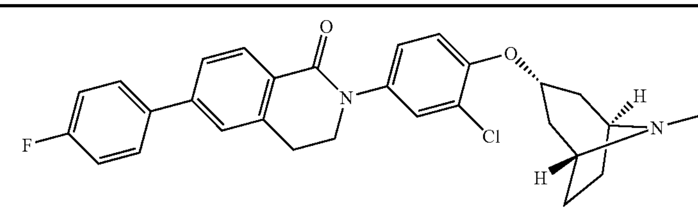 | C29H28ClFN2O2 | 491.01 | 491 |
| 53 | 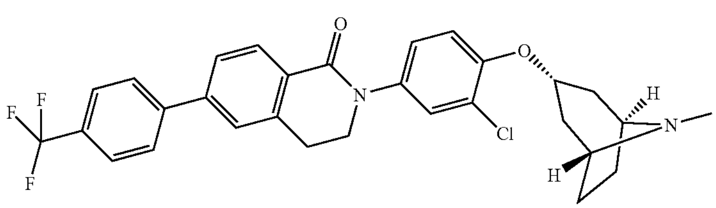 [SMILES: CN1[C@@H]2CC[C@H]1C[C@@H](Oc1ccc(N3CCc4cc(-c5ccc(C(F)(F)F)cc5)ccc4C3=O)cc1Cl)C2] | C30H28ClF3N2O2 | 541.02 | 541 |
| 54 | | C29H28Cl2N2O2 | 507.46 | 507 | was dried and concentrated. The product with the molecular weight of 232.30 (C13H12O2S) was obtained in this way; MS (ESI): 233 (M+H+).

3-Methyl-5-p-tolylthiophene-2-carbaldehyde

5-Bromo-3-methylthiophene-2-carbaldehyde (Spinelli, D. et al., J. Chem. Soc. Perkin Trans. 2, 1972, (12), 1866-9) was reacted with 4-methylphenylboronic acid by method J. The product with the molecular weight of 216.30 (C13H12OS) was obtained in this way; MS (ESI): 217 (M+H+).

Example 56

2-[4-((1R,3R,5S)-8-Methyl-8-azabicyclo[3.2.1]oct-3-yloxy)phenyl]-6-[(S)-1-(tetrahydrofuran-2-yl)methoxy]-2H-isoquinolin-1-one

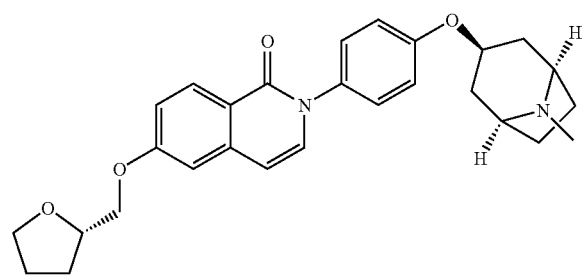 [SMILES: CN1[C@@H]2CC[C@H]1C[C@@H](Oc1ccc(-n3ccc4cc(OC[C@@H]5CCCO5)ccc4c3=O)cc1)C2]

Method K

A solution of trimethylaluminum (2M in toluene, 250 µL) was added to a solution of 4-((1R,3R,5S)-8-methyl-8-azabicyclo[3.2.1]oct-3-yloxy)phenylamine (52 mg) in dichloromethane (2 mL) at 0° C., and the mixture was stirred at room temperature for 15 min.

A solution of 6-[(S)-1-(tetrahydrofuran-2-yl)methoxy]isochromen-1-one (50 mg) in dichloromethane (1 mL) was added thereto, and the resulting solution was stirred at room temperature for 3 h. Addition of Rochelle's salt solution was followed by extraction of the mixture with dichloromethane, drying over magnesium sulfate and concentration. The residue was treated with 4N HCl in dioxane (5 mL), concentrated and purified by preparative HPLC. The product with the molecular weight of 460.58 (C28H32N2O4) was obtained in this way; MS (ESI): 461 (M+H+).

6-[(S)-1-(Tetrahydrofuran-2-yl)methoxy]isochromen-1-one

Method L

Methanesulfonic acid tetrahydrofuran-2-ylmethyl ester (2.7 g) and cesium carbonate (12 g) were added to a solution of 6-hydroxyisochromen-1-one (2 g) in DMF (50 mL) and the mixture was stirred at 80° C. for 7 h. After addition of water, the mixture was extracted with dichloromethane, dried over magnesium sulfate and concentrated. The product with the molecular weight of 246.27 (C14H14O4) was obtained in this way; MS (ESI): 247 (M+H+). 6-[(R)-1-(Tetrahydrofuran-2-yl)methoxy]isochromen-1-one was synthesized analogously.

Methanesulfonic acid (S)-1-(tetrahydro-furan-2-yl)methyl ester

To a solution of (S)-1-(Tetrahydro-furan-2-yl)-methanol (7.95 g) in pyridine (35 mL) methanesulfonyl chloride (7.47 g) was added at −15° C. and stirred for 5 h at 0° C. After addition of water, the mixture was extracted with dichloromethane, dried over magnesium sulfate and concentrated. The product with the molecular weight of 180.22 (C6H12O4S); was obtained in this way; MS (ESI): 181 (M+H+). Methanesulfonic acid (R)-1-(tetrahydro-furan-2-yl)methyl ester was prepared analogously.

6-Hydroxyisochromen-1-one

Method M

A solution of boron tribromide (1M in dichloromethane, 130 mL) was added to a solution of 6-methoxyisochromen-1-one (9.3 g) in dichloromethane (300 mL) at 0° C., and the mixture was stirred at room temperature for 16 h. After addition of sodium carbonate solution, the mixture was washed with ethyl acetate, and the aqueous phase was acidified with 2N HCl, extracted with ethyl acetate, dried over magnesium sulfate and concentrated. The residue was chromatographed on silica gel. The product with the molecular weight of 162.15 (C9H6O3) was obtained in this way; MS (ESI): 163 (M+H+).

6-Methoxyisochromen-1-one

Method N

A solution of 6-methoxyisochroman-1-one (15.1 g), NBS (27 g) and benzoyl peroxide (500 mg) in tetrachloromethane (250 mL) was heated to reflux while irradiating with light for 3 h. The mixture was filtered and the filtrate was concentrated. The residue was dissolved in triethylamine (100 mL) and stirred at room temperature for 48 h. The reaction mixture was partitioned between water and ethyl acetate and brought to pH 1 with concentrated hydrochloric acid. The organic phase was separated off, dried over magnesium sulfate and concentrated. The residue was chromatographed on silica gel. The product with the molecular weight of 176.17 (C10H8O3) was obtained in this way; MS (ESI): 177 (M+H+).

6-Methoxyisochroman-1-one

Method O

A 1.6M solution of n-butyllithium in hexane (145.9 mL) was added dropwise to a solution of diisopropylamine (33.5 mL) in dry THF (190 mL) at −78° C. The reaction mixture was then warmed to room temperature for 5 min and again cooled to −78° C., and a solution of 4-methoxy-2-methylbenzoic acid in dry THF (210 mL) was added dropwise. After stirring at this temperature for 10 min, paraformaldehyde (7 g) was added. The reaction mixture was then allowed to reach room temperature and was stirred at this temperature for 4 h. Water was added to the reaction mixture, and then the THF was removed in vacuo and the aqueous phase was extracted with diethyl ether. The aqueous phase was acidified with conc. HCl, and the resulting precipitate was filtered off and washed with water several times. The product with the molecular weight of 178.06 (C10H10O3) was obtained in this way; MS (ESI): 179 (M+H+).

The compounds in table 5 were obtained analogously.

TABLE 5

| EX. No. | Structure | Molecular formula | Molecular weight | ESI-MS [M + H]+ |
|---|---|---|---|---|
| 57 | 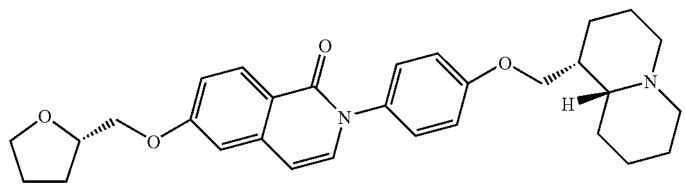 [SMILES: O=c1c2ccc(OC[C@@H]3CCCO3)cc2ccn1-c1ccc(OC[C@@H]2CCCN3CCCC[C@H]23)cc1] | C30H36N2O4 | 488.63 | 489 |
| 58 | 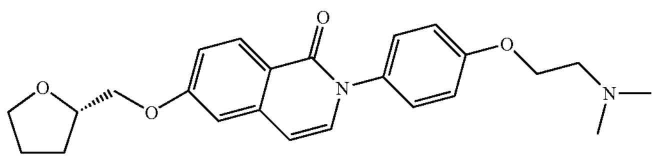 [SMILES: CN(C)CCOc1ccc(-n2ccc3cc(OC[C@@H]4CCCO4)ccc3c2=O)cc1] | C24H28N2O4 | 408.50 | 409 |
| 59 | 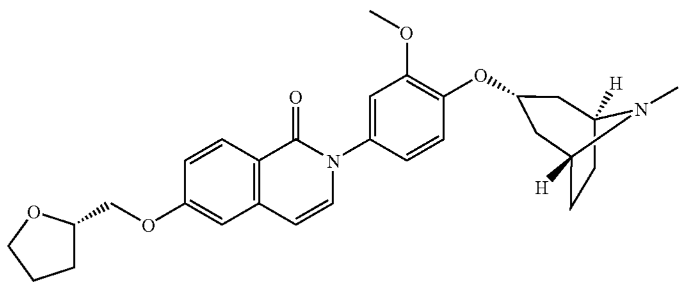 [SMILES: COc1cc(-n2ccc3cc(OC[C@@H]4CCCO4)ccc3c2=O)ccc1O[C@H]1C[C@H]2CC[C@@H](C1)N2C] | C29H34N2O5 | 490.60 | 491 |
| 60 | 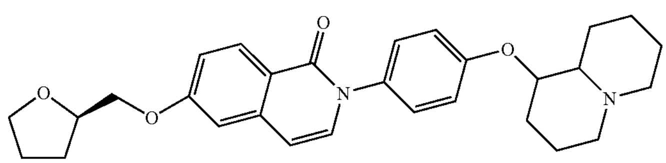 [SMILES: O=c1c2ccc(OC[C@H]3CCCO3)cc2ccn1-c1ccc(OC2CCCN3CCCCC23)cc1] | C29H34N2O4 | 474.61 | 475 |
| 61 | 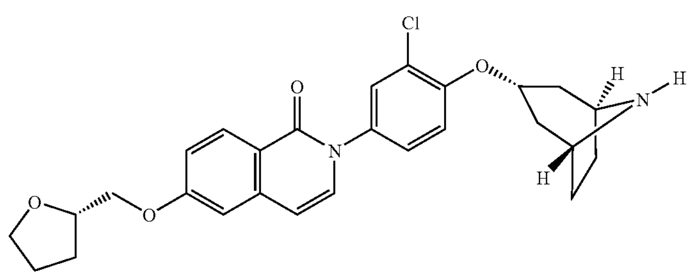 [SMILES: O=c1c2ccc(OC[C@@H]3CCCO3)cc2ccn1-c1ccc(O[C@H]2C[C@H]3CC[C@@H](C2)N3)c(Cl)c1] | C27H29ClN2O4 | 481.00 | 481 |
| 62 | 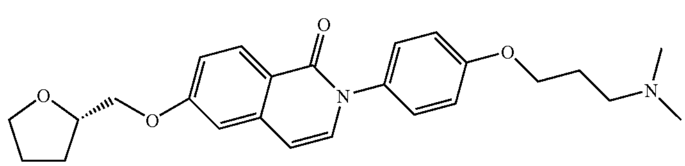 [SMILES: CN(C)CCCOc1ccc(-n2ccc3cc(OC[C@@H]4CCCO4)ccc3c2=O)cc1] | C25H30N2O4 | 422.53 | 423 |
| 63 | 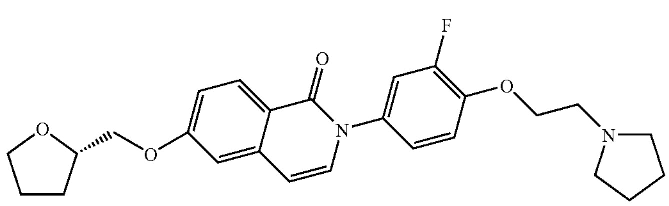 [SMILES: O=c1c2ccc(OC[C@@H]3CCCO3)cc2ccn1-c1ccc(OCCN2CCCC2)c(F)c1] | C26H29FN2O4 | 452.53 | 453 |

TABLE 5-continued

| EX. No. | Structure | Molecular formula | Molecular weight | ESI-MS [M + H]+ |
|---|---|---|---|---|
| 64 | 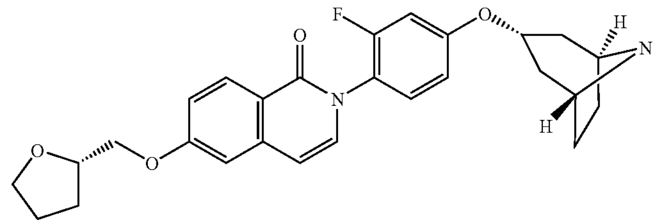 [SMILES: O=c1c2ccc(OC[C@@H]3CCCO3)cc2ccn1-c1ccc(O[C@H]2C[C@H]3CC[C@@H](C2)N3)cc1F] | C28H31FN2O4 | 478.57 | 479 |
| 65 | 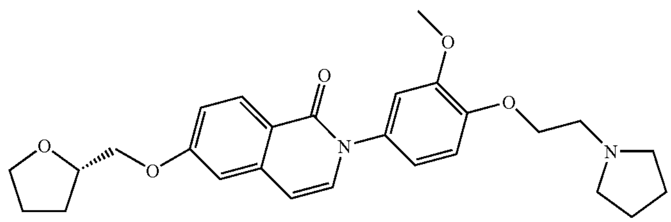 [SMILES: COc1cc(-n2ccc3cc(OC[C@@H]4CCCO4)ccc3c2=O)ccc1OCCN1CCCC1] | C27H32N2O5 | 464.57 | 465 |
| 66 | 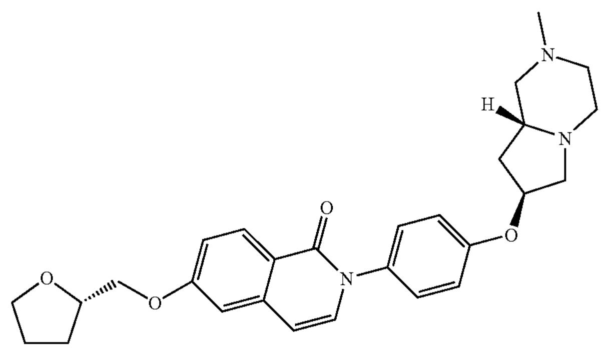 [SMILES: CN1CCN2C[C@@H](Oc3ccc(-n4ccc5cc(OC[C@@H]6CCCO6)ccc5c4=O)cc3)C[C@@H]2C1] | C28H33N3O4 | 475.59 | 476 |
| 67 | 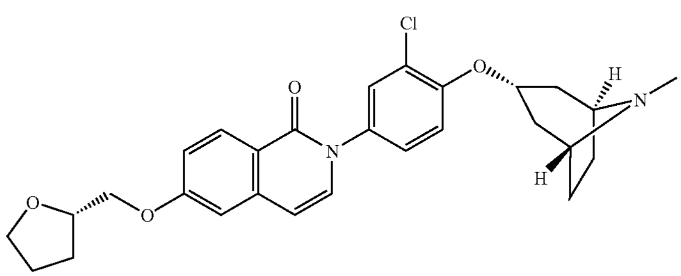 [SMILES: CN1[C@@H]2CC[C@H]1C[C@@H](Oc1ccc(-n3ccc4cc(OC[C@@H]5CCCO5)ccc4c3=O)cc1Cl)C2] | C28H31ClN2O4 | 495.02 | 495 |
| 68 | 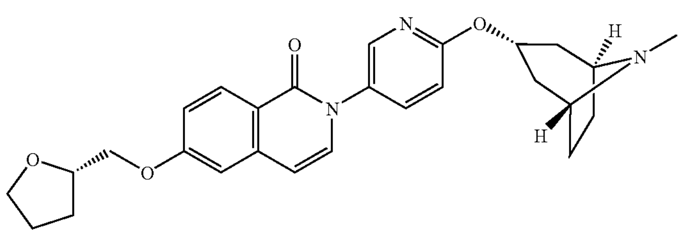 [SMILES: CN1[C@@H]2CC[C@H]1C[C@@H](Oc1ccc(-n3ccc4cc(OC[C@@H]5CCCO5)ccc4c3=O)cn1)C2] | C27H31N3O4 | 461.57 | 462 |
| 69 | 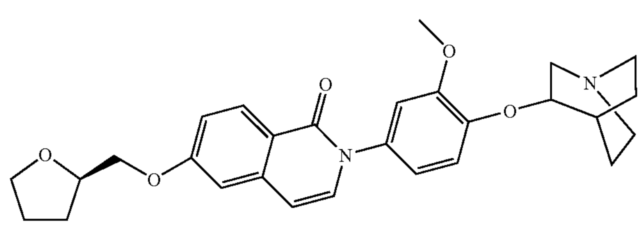 [SMILES: COc1cc(-n2ccc3cc(OC[C@H]4CCCO4)ccc3c2=O)ccc1OC1CN2CCC1CC2] | C28H32N2O5 | 476.58 | 477 |

TABLE 5-continued

| EX. No. | Structure | Molecular formula | Molecular weight | ESI-MS [M + H]+ |
|---|---|---|---|---|
| 70 | 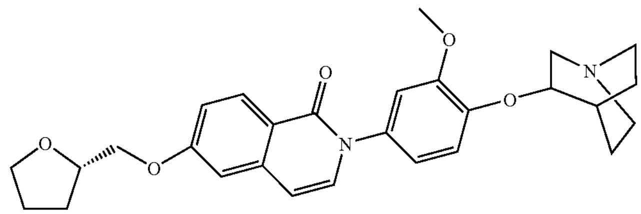 [SMILES: COc1cc(-n2ccc3cc(OC[C@@H]4CCCO4)ccc3c2=O)ccc1OC1CN2CCC1CC2] | C28H32N2O5 | 476.58 | 477 |
| 71 | 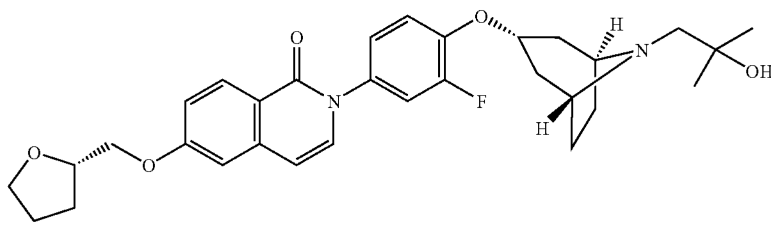 [SMILES: CC(C)(O)CN1[C@@H]2CC[C@H]1C[C@@H](Oc1ccc(-n3ccc4cc(OC[C@@H]5CCCO5)ccc4c3=O)cc1F)C2] | C31H37FN2O5 | 536.64 | 537 |
| 72 | 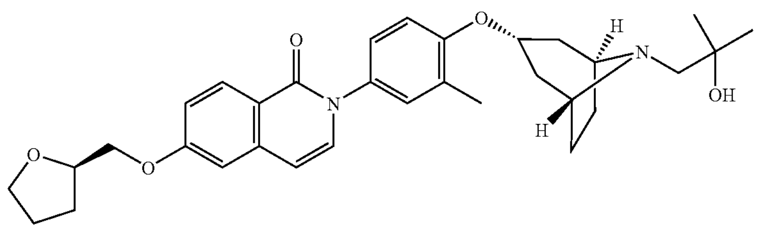 [SMILES: Cc1cc(-n2ccc3cc(OC[C@H]4CCCO4)ccc3c2=O)ccc1O[C@H]1C[C@H]2CC[C@@H](C1)N2CC(C)(C)O] | C32H40N2O5 | 532.68 | 533 |
| 73 | 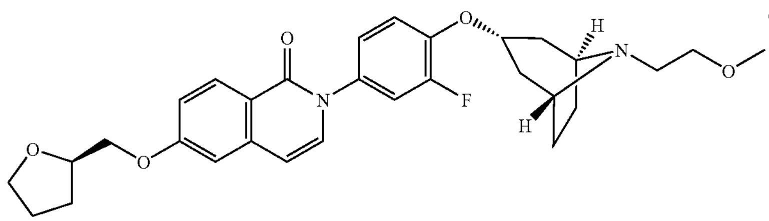 [SMILES: COCCN1[C@@H]2CC[C@H]1C[C@@H](Oc1ccc(-n3ccc4cc(OC[C@H]5CCCO5)ccc4c3=O)cc1F)C2] | C30H35FN2O5 | 522.62 | 523 |
| 74 | 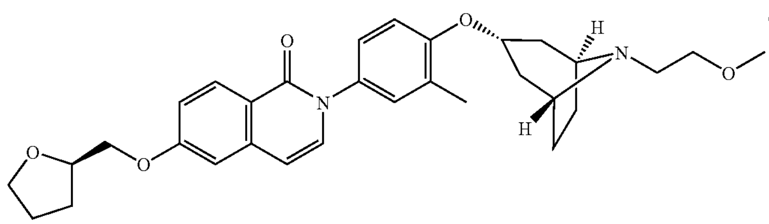 [SMILES: COCCN1[C@@H]2CC[C@H]1C[C@@H](Oc1ccc(-n3ccc4cc(OC[C@H]5CCCO5)ccc4c3=O)cc1C)C2] | C31H38N2O5 | 518.65 | 519 |
| 75 | 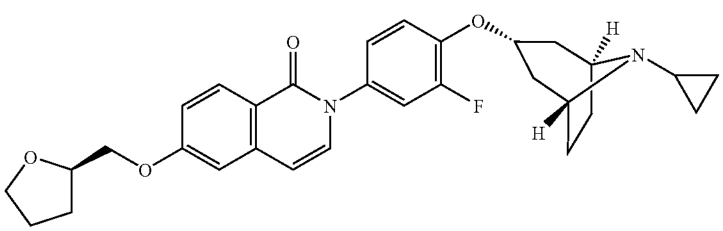 [SMILES: O=c1c2ccc(OC[C@H]3CCCO3)cc2ccn1-c1ccc(O[C@H]2C[C@H]3CC[C@@H](C2)N3C2CC2)c(F)c1] | C30H33FN2O4 | 504.60 | 505 |

1-[(1S,3R,5R)-3-(4-Amino-2-fluorophenoxy)-8-azabicyclo[3.2.1]oct-8-yl]-2-methylpropan-2-ol 1-[(1S,3R,5R)-3-(2-Fluoro-4-nitrophenoxy)-8-azabicyclo[3.2.1]oct-8-yl]-2-methylpropan-2-ol was reduced by method F. The product with the molecular weight of 308.40 (C17H25FN2O2) was obtained in this way; MS (ESI): 309 (M+H+).

Method P

1-[(1S,3R,5R)-3-(2-Fluoro-4-nitrophenoxy)-8-azabicyclo[3.2.1]oct-8-yl]-2-methylpropan-2-ol A mixture of (1S,3R,5R)-3-(2-fluoro-4-nitrophenoxy)-8-azabicyclo[3.2.1]octane (399.17 mg), isobutylene oxide (865.4 mg) and cesium carbonate (977.5 mg) in DMF (5 mL) was heated at 80° C. overnight. The reaction mixture was then diluted with ethyl acetate and water, and the aqueous phase was extracted several times with ethyl acetate. The combined organic phases were dried over sodium sulfate, and the solvent was removed in vacuo. The product with the molecular weight of 338.38 (C17H23FN2O4) was obtained in this way; MS (ESI): 339 (M+H+).

Method Q

(1S,3R,5R)-3-(2-Fluoro-4-nitrophenoxy)-8-azabicyclo[3.2.1]octane

Trifluoroacetic acid (20.5 mL) was added to a solution of (1S,3R,5R)-3-(2-fluoro-4-nitrophenoxy)-8-azabicyclo[3.2.1]octane-8-carboxylic acid tert-butyl ester (4.9 g) in methylene chloride (34.4 mL). The reaction mixture was stirred at room temperature for 30 min. The solvent was then removed in vacuo. The product with the molecular weight of 266.27 (C13H15FN2O3) was obtained in this way; MS (ESI): 267 (M+H+).

(1S,3R,5R)-3-(2-Fluoro-4-nitrophenoxy)-8-azabicyclo[3.2.1]octane-8-carboxylic acid tert-butyl ester (1S,3R,5R)-3-Hydroxy-8-azabicyclo[3.2.1]octane-8-carboxylic acid tert-butyl ester was reacted with 3,4-difluoronitrobenzene by method E. The product with the molecular weight of 366.39 (C18H23FN2O5) was obtained in this way; MS (ESI): 367 (M+H+).

(1S,3R,5R)-3-Hydroxy-8-azabicyclo[3.2.1]octane-8-carboxylic acid tert-butyl ester A solution of (1S,3R,5R)-8-azabicyclo[3.2.1]octan-3-ol (10 g) in THF (100 mL) was added to a solution of sodium hydroxide (3.15 g) in water (50 mL). Di-tert-butyl dicarbonate (17.2 g) was then added, and the reaction mixture was stirred at room temperature for 2 h. The THF was removed in vacuo and the residue was mixed with water and ethyl acetate. The aqueous phase was extracted several times with ethyl acetate. The combined organic phases were dried over sodium sulfate and the solvent was removed in vacuo. The product with the molecular weight of 227.30 (C12H21NO3) was obtained in this way; MS (ESI): 228 (M+H+).

3-Fluoro-4-[(1S,3R,5R)-8-(2-methoxyethyl)-8-azabicyclo[3.2.1]oct-3-yloxy]phenylamine (1S,3R,5R)-3-(2-Fluoro-4-nitrophenoxy)-8-(2-methoxyethyl)-8-azabicyclo[3.2.1]octane was reduced by method F. The product with the molecular weight of 294.37 (C16H23FN2O2) was obtained in this way; MS (ESI): 295 (M+H+).

(1S,3R,5R)-3-(2-Fluoro-4-nitrophenoxy)-8-(2-methoxyethyl)-8-azabicyclo[3.2.1]octane (1S,3R,5R)-3-(2-Fluoro-4-nitrophenoxy)-8-azabicyclo[3.2.1]octane was reacted with 2-bromoethyl methyl ether by method G. The product with the molecular weight of 324.35 (C16H21FN2O4) was obtained in this way; MS (ESI): 325 (M+H+).

4-((1S,3R,5R)-8-Cyclopropyl-8-azabicyclo[3.2.1]oct-3-yloxy)-3-fluorophenylamine was reduced by method F. The product with the molecular weight of 276.35 (C16H21FN2O) was obtained in this way; MS (ESI): 277 (M+H+).

4-((1S,3R,5R)-8-Cyclopropyl-8-azabicyclo[3.2.1]oct-3-yloxy)-3-fluorophenylamine A 1M solution of sodium cyanoborohydride in THF (6 mL) was added to a mixture of 4-[(1S,3R,5R)-(8-azabicyclo[3.2.1]oct-3-yl)oxy]-3-fluorophenylamine (399.2 mg), (1-ethoxycyclopropoxy)trimethylsilane (1.3 g), acetic acid (0.86 mL) in methanol (5 mL). The reaction mixture was heated at 60° C. for 8 h. The solvent was then removed in vacuo, and the residue was taken up in ethyl acetate and water. The ethyl acetate phase was washed with water and dried over sodium sulfate, and the solvent was removed in vacuo. The product with the molecular weight of 306.34 (C16H19FN2O3) was obtained in this way; MS (ESI): 307 (M+H+).

Other alkoxy substituted aromatic amines which were employed for the compound of table 5 were prepared by reacting the corresponding fluoronitro aromatic compounds with the corresponding alcohols according to method E and subsequent reduction according to method D.

The compounds 72 and 74 were prepared in analogy to compounds 71 and 73 by using 1-Fluoro-2-methyl-4-nitrobenzene.

Example 76

2-{3-Fluoro-4-[(1S,3R,5R)-8-(2-fluoroethyl)-8-azabicyclo[3.2.1]oct-3-yloxy]phenyl}-6-[(R)-1-(tetrahydrofuran-2-yl)methoxy]-2H-isoquinolin-1-one

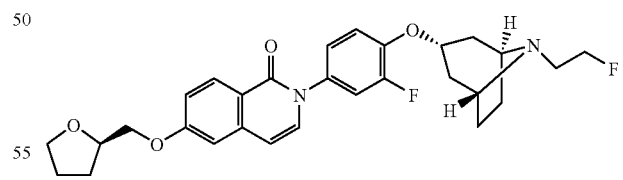

A mixture of 2-{4-[(1S,3R,5R)-(8-azabicyclo[3.2.1]oct-3-yl)oxy]-3-fluorophenyl}-6-[(R)-1-(tetrahydrofuran-2-yl)methoxy]-2H-isoquinolin-1-one (46.4 mg), 1-bromo-2-fluoroethane (31.7 mg), potassium carbonate (41.5 mg) and sodium iodide (1.5 mg) in DMF (0.5 mL) was heated at 60° C. for 6 h. The reaction mixture was then mixed with ethyl acetate and water, and the aqueous phase was extracted several times with ethyl acetate. The combined organic phases were dried over sodium sulfate and the solvent was removed in vacuo. The product was purified by preparative HPLC. The product with the molecular weight of 510.58 (C29H32F2N2O4) was obtained in this way; MS (ESI): 511 (M+H+).

2-{4-[(1S,3R,5R)-8-(2-Fluoroethyl)-8-azabicyclo[3.2.1]oct-3-yloxy]-3-methylphenyl}-6-[(R)-1-(tetrahydrofuran-2-yl)methoxy]-2H-isoquinolin-1-one was synthesized analogously (example 77).

2-{4-[(1S,3R,5R)-(8-Aza-bicyclo[3.2.1]oct-3-yl)oxy]-3-fluoro-phenyl}-6-[(R)-1-(tetrahydrofuran-2-yl)methoxy]-2H-isoquinolin-1-one (1S,3R,5R)-3-(2-Fluoro-4-{1-oxo-6-[(R)-1-(tetrahydrofuran-2-yl)methoxy]-1H-isoquinolin-2-yl}phenoxy)-8-azabicyclo[3.2.1]octane-8-carboxylic acid tert-butyl ester was reacted with 6-[(R)-1-(tetrahydrofuran-2-yl)methoxy]isochromen-1-one by method K. The product with the molecular weight of 464.21 (C27H29FN2O4) was obtained in this way; MS (ESI): 465 (M+H+).

(1S,3R,5R)-3-(4-Amino-2-fluoro-phenoxy)-8-azabicyclo[3.2.1]octane-8-carboxylic acid tert-butyl ester (1S,3R,5R)-3-Hydroxy-8-aza-bicyclo[3.2.1]octane-8-carboxylic acid tert-butyl ester was reacted with 3,4-Difluoronitrobenzol in NMP according to method E. The product with the molecular weight of 366.39 (C18H23FN2O5) was obtained in this way; 367 (M+H+).

Example 78

2-[4-((1S,3R,5R)-8-Cyclopropylmethyl-8-azabicyclo[3.2.1]oct-3-yloxy)-3-fluorophenyl]-6-[(R)-1-(tetrahydrofuran-2-yl)methoxy]-2H-isoquinolin-1-one

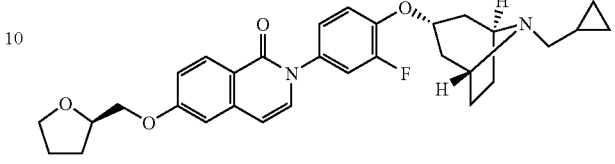

A 1M sodium cyanoborohydride solution in THF (0.6 mL) was added to a mixture of 2-{4-[(1S,3R,5R)-(8-azabicyclo[3.2.1]oct-3-yl)oxy]-3-fluorophenyl}-6-[(R)-1-(tetrahydrofuran-2-yl)methoxy]-2H-isoquinolin-1-one (111.1 mg), cyclopropanecarbaldehyde (30.2 mg), acetic acid (12.3 µL) in methanol (2.2 mL)/methylene chloride (1.4 mL). The reaction mixture was stirred at room temperature for 8 h. The solvent was then removed in vacuo and the residue was taken up in ethyl acetate and water. The aqueous phase was extracted several times with ethyl acetate. The combined organic phases were dried over sodium sulfate and the solvent was removed in vacuo. The crude product was purified by preparative HPLC. The product with the molecular weight of 518.26 (C31H35FN2O4) was obtained in this way; MS (ESI): 519 (M+H+).

The compounds in table 6 were synthesized analogously.

TABLE 6

| EX. No. | Structure | Molecular formula | Molecular weight | ESI-MS [M + H]+ |
|---|---|---|---|---|
| 79 | 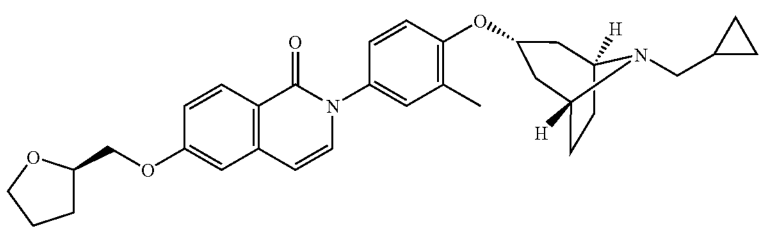 [SMILES: Cc1cc(-n2ccc3cc(OC[C@H]4CCCO4)ccc3c2=O)ccc1O[C@H]1C[C@H]2CC[C@@H](C1)N2CC1CC1] | C32H38N2O4 | 514.66 | 515 |
| 80 | 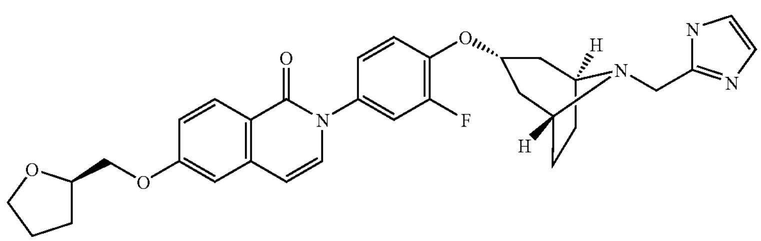 [SMILES: O=c1c2ccc(OC[C@H]3CCCO3)cc2ccn1-c1ccc(O[C@H]2C[C@H]3CC[C@@H](C2)N3Cc2ncc[nH]2)c(F)c1] | C31H33FN4O4 | 544.63 | 545 |
| 81 | 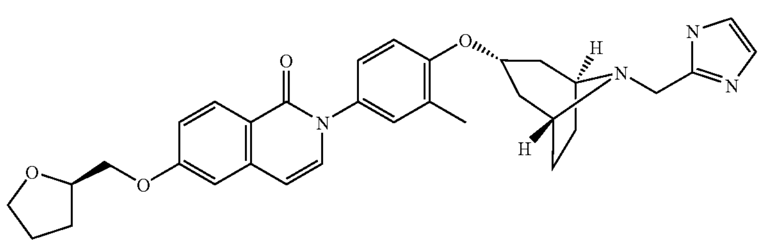 [SMILES: Cc1cc(-n2ccc3cc(OC[C@H]4CCCO4)ccc3c2=O)ccc1O[C@H]1C[C@H]2CC[C@@H](C1)N2Cc1ncc[nH]1] | C32H36N4O4 | 540.66 | 541 |

Example 82

6-((S)-2-Hydroxybutoxy)-2-[3-methoxy-4-(2-pyrrolidin-1-ylethoxy)phenyl]-2H-isoquinolin-1-one

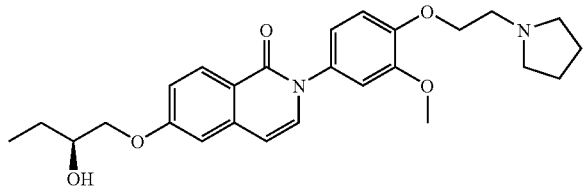 [SMILES: CC[C@H](O)COc1ccc2c(=O)n(-c3ccc(OCCN4CCCC4)c(OC)c3)ccc2c1]

6-((S)-2-Hydroxybutoxy)isochromen-1-one and 3-methoxy-4-(2-pyrrolidin-1-ylethoxy)phenylamine were reacted by method K. The product with the molecular weight of 452.56 (C26H32N2O5) was obtained in this way; MS (ESI): 453 (M+H+).

Method R

A mixture of 6-hydroxyisochromen-1-one (405 mg), (S)-(−)-1,2-epoxybutane (361 mg), cesium fluoride (1.1 g) and DMF (3 mL) was stirred at 130° C. for 4 h. Addition of water was followed by extraction with dichloromethane, drying over magnesium sulfate and concentration. The residue was purified by preparative HPLC. The product with the molecular weight of 234.25 (C13H14O4) was obtained in this way; MS (ESI): 235 (M+H+).

Example 83

2-{4-[2-(3-Azabicyclo[3.2.0]hept-3-yl)ethoxy]-3-methoxyphenyl}-6-[(S)-1-(tetrahydrofuran-2-yl)methoxy]-2H-isoquinolin-1-one

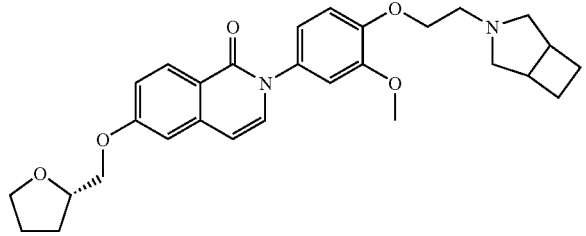 [SMILES: COc1cc(-n2ccc3cc(OC[C@@H]4CCCO4)ccc3c2=O)ccc1OCCN1CC2CCC2C1]

Method S

A solution of (2-methoxy-4-{1-oxo-6-[(S)-1-(tetrahydrofuran-2-yl)methoxy]-1H-isoquinolin-2-yl}phenoxy)acetaldehyde (27 mg), 3-azabicyclo[3.2.0]heptane (18 mg; M. Rice et al., J. Org. Chem. 1957, 22, 1100-1103) and sodium cyanoborohydride (10 mg) in THF (1 mL) was stirred at room temperature for 3 h. The solvent was removed in vacuo. The residue was purified by preparative HPLC. The product with the molecular weight of 490.60 (C29H34N2O5) was obtained in this way; MS (ESI): 491 (M+H+).

(2-Methoxy-4-{1-oxo-6-[(S)-1-(tetrahydrofuran-2-yl)methoxy]-1H-isoquinolin-2-yl}phenoxy)acetaldehyde Method T A solution of 2-[4-(2,2-dimethoxyethoxy)-3-methoxyphenyl]-6-[(S)-1-(tetrahydrofuran-2-yl)methoxy]-2H-isoquinolin-1-one (94 mg) in 10:10:1 TFA/dichloromethane/water (2 mL) was stirred at room temperature for 2 h. The solvent was removed in vacuo. The product with the molecular weight of 409.44 (C23H23NO6) was obtained in this way; MS (ESI): 428 (M+water+H+).

2-[4-(2,2-Dimethoxyethoxy)phenyl]-3-methoxy-6-[(S)-1-(tetrahydrofuran-2-yl)methoxy]-2H-isoquinolin-1-one 6-[(S)-1-(Tetrahydrofuran-2-yl)methoxy]isochromen-1-one and 4-(2,2-dimethoxyethoxy)-3-methoxyphenylamine were reacted by method K. The product with the molecular weight of 227.26 (C11H17NO4) was obtained in this way; MS (ESI): 228 (M+H+).

4-(2,2-Dimethoxyethoxy)-3-methoxyphenylamine

Method U

Palladium on carbon (550 mg) was added to a suspension of 1-methoxy-2-(2-methoxy-4-nitrophenoxy)ethanolmethane (4.40 g) in methanol (50 mL), and the mixture was stirred under a hydrogen atmosphere for 8 h. The mixture was filtered and the filtrate was concentrated. The product with the molecular weight of 257.25 (C11H15NO6) was obtained in this way; MS (ESI): 258 (M+H+).

1-Methoxy-2-(2-methoxy-4-nitrophenoxy)ethanolmethane

Method V

A solution of 2-methoxy-4-nitrophenol (3 g), bromoacetaldehyde dimethyl acetal (5 g) and cesium carbonate (8.7 g) in DMF (10 mL) was stirred at 130° C. for 8 h. Addition of water was followed by extraction with ethyl acetate, drying over magnesium sulfate and concentration. The product with the molecular weight of 257.25 (C11H15NO6) was obtained in this way; MS (ESI): 258 (M+H+).

The compounds in table 7 were obtained analogously

TABLE 7

| EX. No. | Structure | Molecular formula | Molecular weight | ESI-MS [M + H]+ |
|---|---|---|---|---|
| 84 | 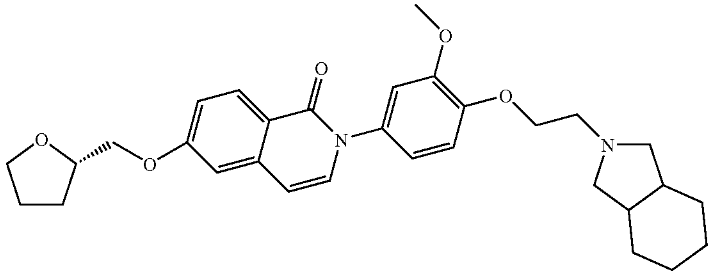 [SMILES: COc1cc(-n2ccc3cc(OC[C@@H]4CCCO4)ccc3c2=O)ccc1OCCN1CC2CCCCC2C1] | C31H38N2O5 | 518.66 | 519 |

TABLE 7-continued

| EX. No. | Structure | Molecular formula | Molecular weight | ESI-MS [M + H]+ |
|---|---|---|---|---|
| 85 | 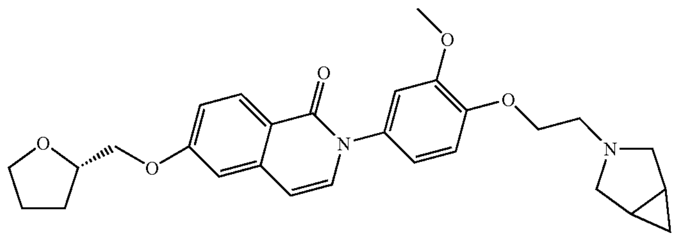 [SMILES: COc1cc(-n2ccc3cc(OC[C@@H]4CCCO4)ccc3c2=O)ccc1OCCN1CC2CC2C1] | C28H32N2O5 | 476.58 | 477 |
| 86 | 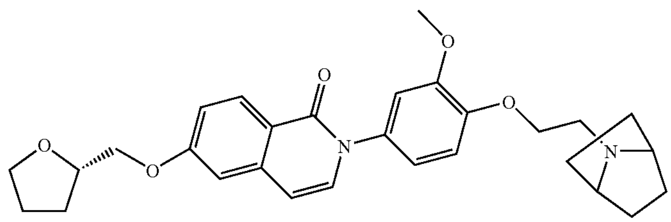 [SMILES: COc1cc(-n2ccc3cc(OC[C@@H]4CCCO4)ccc3c2=O)ccc1OCCN1C2CCC1CC2] | C29H34N2O5 | 490.60 | 491 |

3-Azabicyclo[3.1.0]hexane

Pd/C (5%) (7.4 mg) was added to a solution of 3-benzyl-3-azabicyclo[3.1.0]hexane (240 mg) in methanol (20 mL). The solution was stirred under a hydrogen atmosphere (atmospheric pressure) at room temperature for 6 h. The reaction mixture was filtered through Celite and the solvent was removed in vacuo. The product with the molecular weight of 83.07 (C5H9N) was obtained in this way; MS (ESI): 84 (M+H+).

3-Benzyl-3-azabicyclo[3.1.0]hexane

A solution of iodine (2.27 g) in THF (27.9 mL) was added dropwise to a mixture of sodium borohydride (818 mg) in dry THF (45 mL) at 0° C. over the course of 40 min. Subsequently, at this temperature, a solution of 3-benzyl-3-azabicyclo[3.1.0]hexane-2,4-dione (750 mg) in THF (11.1 mL) was added dropwise. The reaction mixture was then heated under reflux for 6 h. The mixture was cooled to 0° C. and 3N HCl was cautiously added. The reaction solution was then neutralized with 2N sodium hydroxide solution. The aqueous phase was extracted three times with ethyl acetate. The combined organic phases were dried over sodium sulfate and the solvent was removed in vacuo. The crude product was purified by preparative HPLC. The product with the molecular weight of 173.12 (C12H15N) was obtained in this way; MS (ESI): 174 (M+H+).

Example 87
2-{4-[(1R,3R,5S)-(8-Azabicyclo[3.2.1]oct-3-yl)oxy]phenyl}-6-[(S)-1-(tetrahydrofuran-2-yl)methoxy]-3,4-dihydro-2H-isoquinolin-1-one

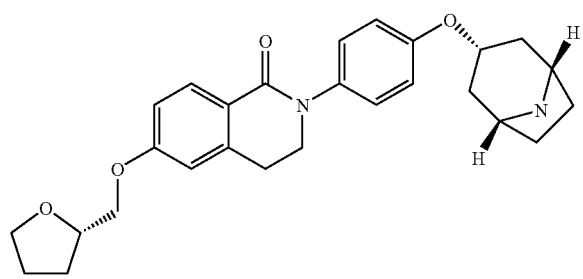 [SMILES: O=C1c2ccc(OC[C@@H]3CCCO3)cc2CCN1c1ccc(O[C@H]2C[C@H]3CC[C@@H](C2)N3)cc1]

2-{4-[(1R,3R,5S)-(8-Azabicyclo[3.2.1]oct-3-yl)oxy]-3-chlorophenyl}-6-[(S)-1-(tetrahydrofuran-2-yl)methoxy]-2H-isoquinolin-1-one was hydrogenated by method U. The product with the molecular weight of 448.57 (C27H32N2O4) was obtained in this way; MS (ESI): 449 (M+H+).

Example 88

6-Butoxy-2-[3-methoxy-4-((1R,3R,5S)-8-methyl-8-azabicyclo[3.2.1]oct-3-yloxy)phenyl]-3,4-dihydro-2H-isoquinolin-1-one

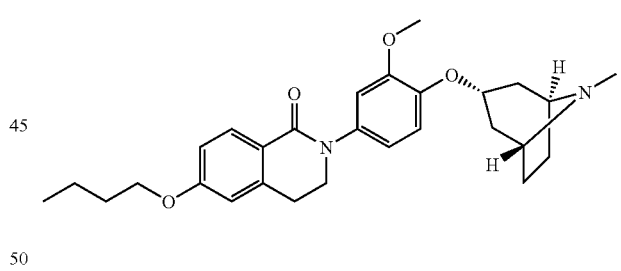

4-Butoxy-2-(2-chloroethyl)benzoyl chloride was reacted with 3-methoxy-4-((1R,3R,5S)-8-methyl-8-azabicyclo[3.2.1]oct-3-yloxy)phenylamine by method A using potassium tert-butoxide as base. The product with the molecular weight of 464.61 (C28H36N2O4) was obtained in this way; MS (ESI): 465 (M+H+).

3-Methoxy-4-((1R,3R,5S)-8-methyl-8-azabicyclo[3.2.1]oct-3-yloxy)phenylamine

Firstly tropine was reacted with 1-fluoro-2-methoxy-4-nitrobenzene by method E, and the resulting nitro compound was then hydrogenated by method F. The product with the molecular weight of 262.35 (C15H22N2O2) was obtained in this way: MS (ESI): 263 (M+H+).

Example 89

6-Butoxy-2-{4-[(1R,3R,5S)-8-(3-fluoropropyl)-8-azabicyclo[3.2.1]oct-3-yloxy]phenyl}-3,4-dihydro-2H-isoquinolin-1-one

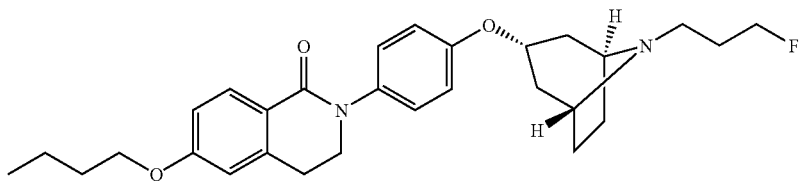 [SMILES: CCCCOc1ccc2c(c1)CCN(c1ccc(O[C@H]3C[C@H]4CC[C@@H](C3)N4CCCF)cc1)C2=O]

4-Butoxy-2-(2-chloroethyl)benzoyl chloride was reacted with 4-[(1R,3R,5S)-8-(3-fluoropropyl)-8-azabicyclo[3.2.1]oct-3-yloxy]phenylamine by method A using potassium tert-butoxide as base. The product with the molecular weight of 480.63 (C29H37FN2O3) was obtained in this way; MS (ESI): 481 (M+H+).

4-[(1R,3R,5S)-8-(3-Fluoropropyl)-8-azabicyclo[3.2.1]oct-3-yloxy]phenylamine

A mixture of nortropine (382 mg), 1-bromo-3-fluoropropane (634 mg), triethylamine (0.42 mL) and DMF was heated at 60° C. for 10 hours and then volatiles were removed. The crude mixture was reacted with 4-fluoronitrobenzene by method E. The nitro compound obtained in this way was hydrogenated by method F. The product with the molecular weight of 278.37 (C16H23FN2O) was obtained in this way; MS (ESI): 279 (M+H+).

Example 90

2-[3-Methoxy-4-(2-pyrrolidin-1-ylethoxy)phenyl]-6-[(S)-1-(tetrahydrofuran-2-yl)methoxy]-3,4-dihydro-2H-isoquinolin-1-one

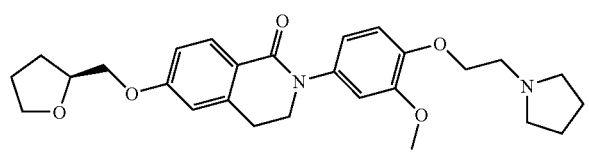 [SMILES: COc1cc(N2CCc3cc(OC[C@@H]4CCCO4)ccc3C2=O)ccc1OCCN1CCCC1]

6-[(S)-1-(Tetrahydrofuran-2-yl)methoxy]isochroman-1-one was firstly converted with thionyl chloride by method B into the corresponding dichloride, and then reacted with 3-methoxy-4-(2-pyrrolidin-1-ylethoxy)phenylamine by method A. The product with the molecular weight of 466.58 (C27H34N2O5) was obtained in this way; MS (ESI): 467 (M+H+).

6-[(S)-1-(Tetrahydrofuran-2-yl)methoxy]isochroman-1-one

A mixture of 6-hydroxyisochroman-1-one (332 mg), methanesulfonic acid (S)-1-(tetrahydrofuran-2-yl)methyl ester (284 mg), cesium carbonate (1.28 g) and DMF (8 mL) was heated at 70° C. for 7 hours. The cooled reaction mixture was partitioned between water and ethyl acetate. The organic phase was dried and concentrated. The crude product was purified by chromatography on silica gel. The product with the molecular weight of 248.28 (C14H16O4) was obtained in this way; MS (ESI): 249 (M+H+).

6-Hydroxyisochroman-1-one

6-Methoxyisochroman-1-one was treated with boron tribromide by method M.

Table 8 summarizes the results which were obtained by the above described calcium immobilization assay.

TABLE 8

| Bsp. No. | $IC_{50}/\mu M$ |
|---|---|
| 01 | 0.93 |
| 06 | 0.27 |
| 09 | 0.87 |
| 15 | 5.44 |
| 17 | 1.14 |
| 26 | 14.84 |
| 34 | 1.15 |
| 42 | 0.78 |
| 45 | 1.11 |
| 55 | 4.90 |
| 56 | 0.16 |
| 65 | 0.13 |
| 69 | 1.18 |
| 72 | 0.49 |
| 74 | 0.14 |
| 75 | 5.01 |
| 81 | 0.46 |
| 83 | 0.84 |
| 84 | 0.25 |
| 86 | 0.21 |
| 89 | 4.39 |

We claim:
1. A compound of formula (I)

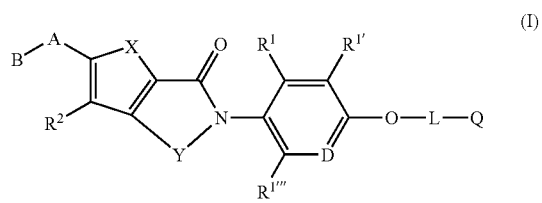

wherein:
D is N or C(R1");
R1, R1', R1" and R1''' are
independently of one another H, F, Cl, Br, I, OH, CF$_3$, NO$_2$, CN, OCF$_3$, O—(C$_1$-C$_6$)-alkyl, O—(C$_1$-C$_4$)- alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R3)(R4), $SO_2$—$CH_3$, COOH, COO—$(C_1-C_6)$-alkyl, CON(R5)(R6), N(R7)CO(R8), N(R9)$SO_2$(R10), CO(R11), or $(C(R12)(R13))_x$-O(R14);

R3, R4, R5, R6, R7 and R9 are
    independently of one another H or $(C_1-C_8)$-alkyl,
or
R3 and R4, or R5 and R6
    independently of one another, taken together with the nitrogen atom to which they are bonded form a 5-6 membered ring which optionally comprises one additional heteroatom selected from the group consisting of NH, N—$(C_1-C_6)$-alkyl, oxygen and sulfur;

R8, R10 and R11 are
    independently of one another H, $(C_1-C_8)$-alkyl, or aryl;
R12 and R13 are
    independently of one another H, or $(C_1-C_8)$-alkyl;
R14 is H, $(C_1-C_6)$-alkyl, or aryl;
x is 0, 1, 2, 3, 4, 5 or 6;
R2 is H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), or $(C(R24)(R25))_{x'}$-O(R26);

R15, R16, R17, R18, R19 and R21 are
    independently of one another H, or $(C_1-C_8)$-alkyl,
or
R15 and R16, or R17 and R18
    independently of one another, taken together with the nitrogen atom to which they are bonded form a 5-6 membered ring which optionally comprises one additional heteroatom from the group consisting of NH, N—$(C_1-C_6)$-alkyl, oxygen and sulfur;

R20, R22 and R23 are
    independently of one another H, $(C_1-C_8)$-alkyl, or aryl;
R24 and R25 are
    independently of one another H, or $(C_1-C_8)$-alkyl;
R26 is H, $(C_1-C_6)$-alkyl, or aryl;
x' is 0, 1, 2, 3, 4, 5 or 6;
Y is C(R27)(R27')C(R28)(R28'), or C(R29)=C(R29');
R27, R27', R28, R28', R29 and R29' are
    independently of one another H, or $(C_1-C_8)$-alkyl;
X is C(R30)=C(R30');
R30 and R30' are
    independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), or $(C(R24)(R25))_x$-O(R26);

A is a linker having 2 to 8 members, where the members are selected from the group consisting of O, S, CO, C(R32)(R33), C(R34)=C(R34'), cyclopropylene, resulting in a chemically reasonable radical;

R34 and R34' are
    independently of one another H or $(C_1-C_8)$-alkyl;
R32 and R33 are
    independently of one another H, $(C_1-C_6)$OH, or O—$(C_1-C_6)$-alkyl;
B is $(C_1-C_4)$-alkoxy-$(C_1-C_4)$alkyl, $(C_2-C_8)$-alkenyl, $(C_2-C_8)$-alkynyl, or a 3 to 10-membered mono-, bi-, tri- or spirocyclic ring which may comprise 0 to 4 heteroatoms selected from the group consisting of oxygen, nitrogen and sulfur, where the ring system is optionally substituted one or more times by F, Cl, Br, $CF_3$, $NO_2$, CN, $(C_1-C_6)$-alkyl, O—$(C_1-C_8)$-alkyl-(C-$C_4$)-alkoxy-$(C_1-C_4)$-alkyl, hydroxy-(C-$C_4$)-alkyl, oxo, CO(R37), CON(R38)(R39), hydroxy, COO(R40), N(R41)CO$(C_1-C_6)$-alkyl, N(R42)(R43), $SO_2CH_3$;

R37, R38, R39, R40, R41, R42 and R43
    independently of one another H or $(C_1-C_8)$-alkyl,
or
R38 and R39, or R42 and R43
    independently of one another taken together with the nitrogen atom to which they are bonded form a 5-6 membered ring which optionally comprises one additional heteroatom selected from the group consisting of NH, N—$(C_1-C_6)$-alkyl, oxygen and sulfur;

L is a bond or (C1-C3)-alkylene;
Q is N(R53')(R54'), or a bi-, tri- or spirocyclic saturated or partly unsaturated ring structure having one nitrogen atom and 0-3 additional heteroatoms selected from the group consisting of N, O and S, where the rings of the structure may be spiro-linked, fused or bridged, and where the ring system is optionally substituted one or more times by F, OH, $CF_3$, CN, $OCF_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R44), $(C(R45)(R46))_o$-R47, or CO$(C(R45)(R46))_p$-R48;

R44 is H, $(C_1-C_8)$-alkyl;
R45 and R46 are
    independently of one another H, $(C_1-C_8)$-alkyl OH, $(C_3-C_8)$-cycloalkyl, or $(C_1-C_4)$-alkoxy-$(C_1-C_4)$-alkyl;
o and p are independently of one another 0, 1, 2, 3, 4, 5 or 6;
R47 and R48 are
    independently of one another OH, F, O—$(C_1-C_8)$-alkyl, CON(R49)(R50), N(R51)CO(R52), N(R53)(R54), $CO_2$(R55), $SO_2$Me, CN, or a 3-10 membered ring system having 0 to 3 heteroatoms selected from the group consisting of N, O and S, which is optionally substituted one or more times by F, Cl, Br, $CF_3$, $(C_1-C_8)$-alkyl, O—$(C_1-C_8)$-alkyl, $(C_1-C_4)$-alkoxy-$(C_1-C_4)$-alkyl, CO(R56), oxo, or OH;
R49, R50, R51, R52, R55 and R56 are
    independently of one another H or $(C_1-C_8)$-alkyl,
or
R49 and R50
    taken together with the nitrogen atom to which they are bonded form a 5-6 membered ring which optionally comprises one additional heteroatom selected from the group consisting of NH, N—$(C_1-C_6)$-alkyl, oxygen and sulfur;
R53, R54, R53' and R54' are
    independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R57), $(C(R58)(R59))_q$-R60, CO(C(R61)(R62))_r$-R63, or CO—$(CH_2)_o$-O—$(C_1-C_6)$-alkyl, or R53 and R54, or R53' and R54'
taken together with the nitrogen atom to which they are bonded form a 4 to 10-membered mono-, bi- or spirocyclic ring which optionally comprises 1 to 3 additional heteroatoms selected from the group consisting of N, O and S, and which is optionally substituted one or more times by F, Cl, Br, $CF_3$, O—($C$-$C_8$)-alkyl, ($C_1$-$C_6$)-alkyl, CO(R64), oxo, OH, ($C_1$-$C_4$)-alkoxy-($C_1$-$C_4$)-alkyl, hydroxy-($C_1$-$C_4$)-alkyl, CON(R65)(R66), N(R67)CO(R68), N(R69)(R70), $CO_2$(R71), or $SO_2$($C_1$-$C_6$)-alkyl;

o' is 0, 1, 2, 3, 4, 5 or 6;

R58 and R59 are
independently of one another H, ($C_1$-$C_6$)-alkyl, or OH;

R57, R61, R62, R64, R65, R66, R67, R68, R69, R70 and R71
independently of one another H, or ($C_1$-$C_6$)-alkyl, or R69 and R70
taken together with the nitrogen atom to which they are bonded form a 5-6 membered ring which optionally comprises one additional heteroatom selected from the group of NH, N—($C_1$-$C_6$)-alkyl, oxygen and sulfur;

q and r are independently of one another 0, 1, 2, 3, 4, 5 or 6;

R60 and R63 are
independently of one another OH, F, O—($C_1$-$C_6$)-alkyl, CN, COO(R78), N(R74)CO($C_1$-$C_6$)-alkyl, N(R76)(R77), CON(R72)(R73), $SO_2$($C_1$-$C_6$)-alkyl, or a 3-12 membered mono-, bi- or spirocyclic ring which optionally comprises one or more heteroatoms from the group of N, O and S, and the 3-12 membered ring is optionally substituted by F, Cl, Br, OH, $CF_3$, $NO_2$, CN, $OCF_3$, oxo, O—($C_1$-$C_6$)-alkyl, ($C_1$-$C_4$)-alkoxy-($C_1$-$C_4$)-alkyl, S—($C_1$-$C_6$)-alkyl, ($C_1C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, N(R76)(R77), COO(R78), $SO_2$($C_1$-$C_6$)-alkyl or COOH; and R72, R73, R74, R76, R77 and R78 are
independently of one another H, or ($C_1$-$C_8$)-alkyl, or R72 and R73, or R76 and R77
independently of one another taken together with the nitrogen atom to which they are bonded form a 5-6 membered ring which optionally comprises one additional heteroatom from the group of NH, N—($C_1$-$C_6$)-alkyl, oxygen and sulfur;

provided that when L is ($C_1$-$C_3$)-alkylene, then B is not an aromatic radical, a cycloalkyl radical, an alk-2-en-1-yl radical or a cycloalk-2-en-1-yl radical, and A does not contain the moiety C(R34')C(R34');

or a pharmaceutically acceptable salt thereof.

2. The compound according to claim 1, wherein
B is ($C_1$-$C_4$)alkoxy-($C_1$-$C_4$)-alkyl, ($C_2$-$C_8$)-alkenyl, ($C_2$-$C_8$)-alkynyl, or a 3 to 10-membered mono-, bi-, tri- or spirocyclic nonaromatic ring which optionally comprises 0 to 4 heteroatoms selected from the group consisting of oxygen, nitrogen and sulfur, where the ring system is optionally substituted one or more times by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO(R37), CON(R38)(R39), hydroxy, COO(R40), N(R41)CO($C_1$-$C_6$)-alkyl, N(R42)(R43), or $SO_2CH_3$;

or a pharmaceutically acceptable salt thereof.

3. The compound according to claim 1, wherein
B is ($C_1$-$C_4$)-alkoxy-($C_1$-$C_4$)-alkyl, ($C_2$-$C_8$)-alkenyl, ($C_2$-$C_8$)-alkynyl, or a 3 to 10-membered mono-, bi-, tri- or spirocyclic nonaromatic ring which optionally comprises 0 to 3 heteroatoms selected from the group consisting of oxygen, nitrogen and sulfur, where the ring system is optionally substituted one or more times by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO(R37), CON(R38)(R39), hydroxy, COO(R40), N(R41)CO($C_1$-$C_6$)-alkyl, N(R42)(R43) or $SO_2CH_3$;

or a pharmaceutically acceptable salt thereof.

4. The compound according to claim 1, wherein
B is ($C_1$-$C_4$)-alkoxy-($C_1$-$C_4$)-alkyl, or a 3 to 10-membered mono-, bi- or spirocyclic nonaromatic ring which optionally comprises 0 to 3 heteroatoms selected from the group consisting of oxygen, nitrogen and sulfur, where the ring system is optionally substituted one or more times by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO(R37), hydroxy, COO(R40), N(R41)CO($C_1$-$C_6$)-alkyl, N(R42)(R43) or $SO_2CH_3$;

or a pharmaceutically acceptable salt thereof.

5. The compound according to claim 1, wherein
B is ($C_1$-$C_4$)-alkoxy-($C_1$-$C_4$)-alkyl, or a 3 to 10-membered mono-, bi- or spirocyclic nonaromatic ring which optionally comprises 0 to 3 heteroatoms selected from the group consisting of oxygen, nitrogen and sulfur, where the ring system is optionally substituted one or more times by F, Cl, $CF_3$, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO(R37), hydroxy, N(R41)CO($C_1$-$C_6$)-alkyl or $SO_2CH_3$;

or a pharmaceutically acceptable salt thereof.

6. The compound according to claim 1, wherein
Q is N(R53')(R54') or a group selected from

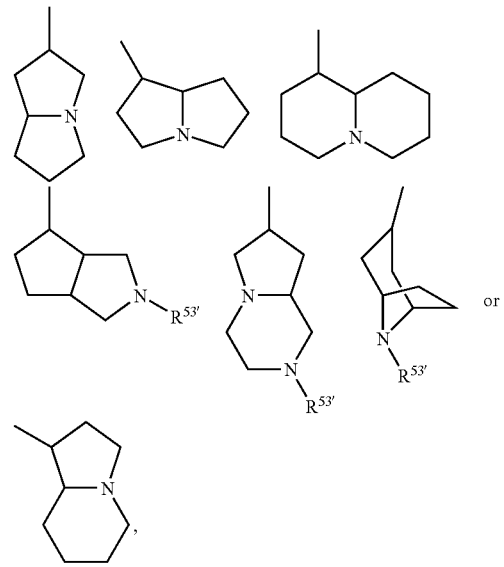

wherein the group is optionally substituted one or more times by F, OH, oxo, ($C_1$-$C_8$)-alkyl, O—($C_1$-$C_8$)-alkyl, or ($C_1$-$C_4$)-alkoxy-($C_1$-$C_4$)-alkyl;

R53' is H, ($C_1$-$C_8$)-alkyl, (C(R58)(R59))$_q$-R60, ($C_1$-$C_4$)-alkoxy-($C_1$-$C_4$)-alkyl, ($C_3$-$C_8$)-alkenyl, ($C_3$-$C_8$)-alkynyl, CO—(C₁-C₈)-alkyl, CO—(CH₂)ₒ'—O—(C₁-C₆)-alkyl, or CO(C(R61)(R62))ᵣN(R76)(R77), R54' is (C₁-C₈)-alkyl, (C(R58)(R59))_q-R60, (C₁-C₄)-alkoxy-(C₁-C₄)-alkyl, (C₃-C₈)-alkenyl, or (C₃-C₈)-alkynyl;

or

R53' and R54' taken together with the nitrogen atom to which they are bonded form a 4 to 10-membered mono-, bi- or spirocyclic ring which optionally comprises 1 to 3 additional heteroatoms selected from the group consisting of oxygen, nitrogen and sulfur, where the heterocyclic ring system is optionally substituted by F, Cl, Br, CF₃, NO₂, CN, (C₁-C₆)-alkyl, O—(C₁-C₈)-alkyl, (C₁-C₄)-alkoxy-(C₁-C₄)-alkyl, hydroxy-(C₁-C₄)-alkyl, oxo, CO(R64), CON(R65)(R66), hydroxy, COO(R71), N(R67)CO(C₁-C₆)-alkyl, N(R69)(R70) or SO₂(C₁-C₆)-alkyl;

o' is 0, 1, 2, 3, 4, 5 or 6; and q and r are independently of one another 0, 1, 2, 3, 4, 5 or 6;

or a pharmaceutically acceptable salt thereof.

7. The compound according to claim 1, wherein
Q is N(R53')(R54') or a group selected from:

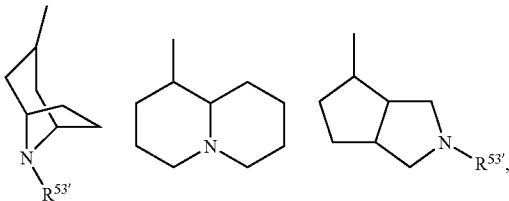

wherein the group is optionally substituted one or more times by F, OH, oxo, (C₁-C₈)-alkyl, O—(C₁-C₈)-alkyl, or (C₁-C₄)-alkoxy-(C₁-C₄)-alkyl;

or a pharmaceutically acceptable salt thereof.

8. The compound according to claim 1, wherein Q is:

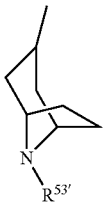

or a pharmaceutically acceptable salt thereof

9. The compound according to claim 1, wherein
R53' is (C₁-C₈)-alkyl, (C(R58)(R59))_q-R60, (C₁-C₄)-alkoxy-(C₁-C₄)-alkyl, (C₃-C₈)-alkenyl, (C₃-C₈)-alkynyl, CO—(C₁-C₈)-alkyl, CO—(CH₂)ₒ'—O—(C₁-C₆)-alkyl, or CO(C(R61)(R62))ᵣN(R76)(R77), R54' is (C₁-C₈)-alkyl, (C(R58)(R59))_q-R60, (C₁-C₄)-alkoxy-(C₁-C₄)-alkyl, (C₃-C₈)-alkenyl, or (C₃-C₈)-alkynyl, or R53' and R54' taken together with the nitrogen atom to which they are bonded form a 4 to 10-membered mono-, bi- or spirocyclic ring which optionally comprises 0 to 3 additional heteroatoms selected from the group consisting of oxygen, nitrogen and sulfur, where the heterocyclic ring system is optionally substituted by F, Cl, Br, CF₃, NO₂, CN, (C₁-C₆)-alkyl, O—(C₁-C₈)-alkyl, (C₁-C₄)-alkoxy-(C₁-C₄)-alkyl, hydroxy-(C₁-C₄)-alkyl, oxo, CO(R64), CON(R65)(R66), hydroxy, COO(R71), N(R67)CO(C₁-C₆)-alkyl, N(R69)(R70) or SO₂(C₁-C₆)-alkyl;

o' is 0, 1, 2, 3, 4, 5 or 6; and q and r are independently of one another 0, 1, 2, 3, 4, 5 or 6;

or a pharmaceutically acceptable salt thereof.

10. The compound according to claim 1, wherein
R53' and R54' independently of one another are (C₁-C₈)-alkyl, (C(R58)(R59))_q-R60, or (C₁-C₄)-alkoxy-(C₁-C₄)-alkyl, or R53' and R54' taken together with the nitrogen atom to which they are bonded form a 4 to 10-membered mono-, bi- or spirocyclic ring which optionally comprises 1 to 2 additional heteroatoms selected from the group consisting of oxygen, nitrogen and sulfur, where the heterocyclic ring system is optionally substituted by F, Cl, Br, CF₃, (C₁-C₆)-alkyl, O—(C₁-C₈)-alkyl, (C₁-C₄)-alkoxy-(C₁-C₄)-alkyl, hydroxy-(C₁-C₄)-alkyl, oxo, CO(R64), hydroxy, N(R67)CO(C₁-C₆)-alkyl, or SO₂ (C₁-C₆)-alkyl; and R60 is OH, F, O—(C₁-C₆)-alkyl, N(R74)CO(C₁-C₆)-alkyl, SO₂(C₁-C₆)-alkyl, or a 3-12 membered mono-, bi- or spirocyclic ring which optionally comprises one or more heteroatoms from the group consisting of N, O and S, and the 3-12 membered ring is optionally substituted by F, Cl, Br, OH, CF₃, NO₂, CN, OCF₃, oxo, O—(C₁-C₆)-alkyl, (C₁-C₄)-alkoxy-(C₁-C₄)-alkyl, (C₁-C₆)-alkyl, (C₂-C₆)-alkenyl, (C₂-C₆)-alkynyl, N(R76)(R77) or SO₂(C₁-C₆)-alkyl;

or a pharmaceutically acceptable salt thereof.

11. The compound according to claim 1, wherein
R53' and R54' taken together with the nitrogen atom to which they are bonded form a 4 to 7-membered monocyclic ring which optionally comprises 1 to 2 additional heteroatoms selected from the group consisting of oxygen, nitrogen and sulfur, where the heterocyclic ring system is optionally substituted by F, Cl, Br, CF₃, NO₂, CN, (C₁-C₆)-alkyl, O—(C₁-C₈)-alkyl, (C₁-C₄)-alkoxy-(C₁-C₄)-alkyl, hydroxy-(C₁-C₄)-alkyl, oxo, CO(R64), CON(R65)(R66), hydroxy, COO(R71), N(R67)CO(C₁-C₆)-alkyl, N(R69)(R70) or SO₂(C₁-C₆)-alkyl;

or a pharmaceutically acceptable salt thereof.

12. The compound according to claim 1, wherein
R53' and R54' taken together with the nitrogen atom to which they are bonded form a 6 to 10-membered bi- or spirocyclic ring which optionally comprises 1 to 3 additional heteroatoms selected from the group consisting of oxygen, nitrogen and sulfur, where the heterocyclic ring system is optionally substituted by F, Cl, Br, CF₃, NO₂, CN, (C₁-C₆)-alkyl, O—(C₁-C₈)-alkyl, (C₁-C₄)-alkoxy-(C₁-C₄)-alkyl, hydroxy-(C₁-C₄)-alkyl, oxo, CO(R64), CON(R65)(R66), hydroxy, COO(R71), N(R67)CO(C₁-C₆)-alkyl, N(R69)(R70) or SO₂(C₁-C₆)-alkyl;

or a pharmaceutically acceptable salt thereof.

13. The compound according to claim 1, wherein
R53' and R54' taken together with the nitrogen atom to which they are bonded form a 6 to 10-membered bi- or spirocyclic ring which optionally comprises 1 to 3 additional heteroatoms selected from the group consisting of oxygen, nitrogen and sulfur, where the heterocyclic ring system is optionally substituted by F, Cl, Br, CF₃, NO₂, CN, (C₁-C₆)-alkyl, O—(C₁-C₈)-alkyl, (C₁-C₄)-alkoxy-(C₁-C₄)-alkyl, hydroxy-(C₁-C₄)-alkyl, oxo, CO(R64), CON(R65)(R66), hydroxy, COO(R71), N(R67)CO($C_1$-$C_6$)-alkyl, N(R69)(R70) or $SO_2$($C_1$-$C_6$)-alkyl;
or a pharmaceutically acceptable salt thereof.

14. The compound according to claim 1, wherein R53' and R54' taken together with the nitrogen atom to which they are bonded form a 6 to 10-membered bi- or spirocyclic non aromatic ring selected from the group consisting of

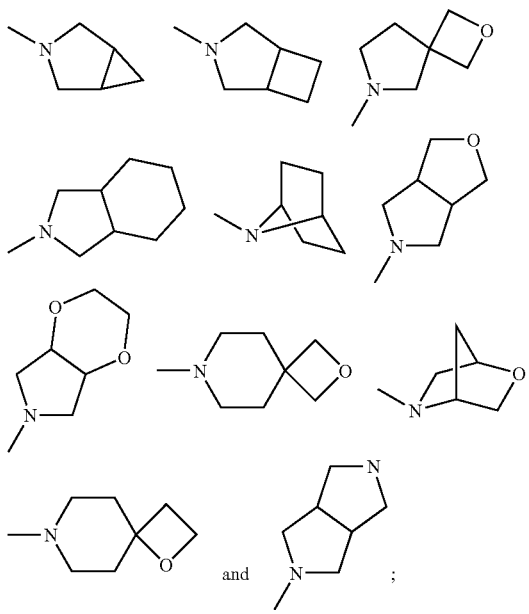

or a pharmaceutically acceptable salt thereof.

15. The compound according to claim 1, wherein O-L-Q is

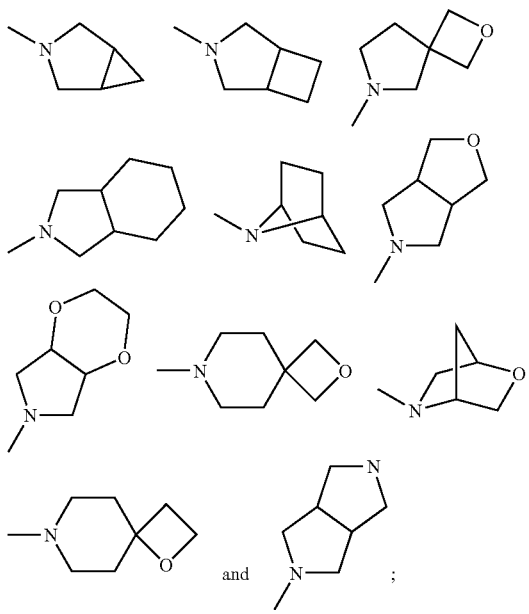

R53' is ($C_1$-$C_8$)-alkyl, (C(R58)(R59))$_q$-R60, ($C_1$-$C_4$)-alkoxy-($C_1$-$C_4$)-alkyl, ($C_3$-$C_8$)-alkenyl, ($C_3$-$C_8$)-alkynyl, CO—($C_1$-$C_8$)-alkyl, CO—($CH_2$)$_o$—O—($C_1$-$C_6$)-alkyl, or CO(C(R61)(R62))$_r$N(R76)(R77), R54' is (C(R58)(R59))$_q$-R60,($C_1$-$C_4$)-alkoxy-($C_1$-$C_4$)-alkyl, ($C_3$-$C_8$)-alkenyl, or ($C_3$-$C_8$)-alkynyl, or R53' and R54' taken together with the nitrogen atom to which they are bonded form a 6 to 10-membered bi- or spirocyclic nonaromatic ring which optionally comprises 1 to 3 additional heteroatoms selected from the group consisting of oxygen, nitrogen and sulfur, where the heterocyclic ring system is optionally substituted by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO(R64), CON(R65)(R66), hydroxy, COO(R71), N(R67)CO($C_1$-$C_6$)-alkyl, N(R69)(R70) or $SO_2$($C_1$-$C_6$)-alkyl;
or a pharmaceutically acceptable salt thereof.

16. The compound according to claim 1, wherein O-L-Q is:

each of which is optionally substituted one or more times by F, OH, oxo, ($C_1$-$C_8$)-alkyl, O—($C_1$-$C_8$)-alkyl, or ($C_1$-$C_4$)-alkoxy-($C_1$-$C_4$)-alkyl; and R53' is ($C_1$-$C_8$)-alkyl, ($C_1$-$C_4$)-alkoxy-($C_1$-$C_4$)-alkyl, ($C_3$-$C_8$)-alkenyl, ($C_3$-$C_8$)-alkynyl, CO—($C_1$-$C_8$)-alkyl, (C(R58)(R59))$_q$-R60, CO(C(R61)(R62))$_r$-N(R76)(R77), or CO—($CH_2$)$_o$—O—($C_1$-$C_6$)-alkyl;
or a pharmaceutically acceptable salt thereof.

17. The compound according to claim 1, wherein O-L-Q is:

which is optionally substituted one or more times by F, OH, oxo, ($C_1$-$C_8$)-alkyl, O—($C_1$-$C_8$)-alkyl, or ($C_1$-$C_4$)-alkoxy-($C_1$-$C_4$)-alkyl; and R53' is ($C_1$-$C_8$)-alkyl, ($C_1$-$C_4$)-alkoxy-($C_1$-$C_4$)-alkyl, ($C_3$-$C_8$)-alkenyl, ($C_3$-$C_8$)-alkynyl, CO—($C_1$-$C_8$)-alkyl, (C(R58)(R59))$_q$-R60, CO(C(R61)(R62))$_r$-N(R76)(R77), or CO—($CH_2$)$_o$—O—($C_1$-$C_6$)-alkyl;
or a pharmaceutically acceptable salt thereof.

18. The compound according to claim 1, wherein
X is C(R30)=C(R30');
Y is C(R29)=C(R29');
O-L-Q is R53' is ($C_1$-$C_8$)-alkyl, (C(R58)(R59))$_q$-R60, ($C_1$-$C_4$)-alkoxy-($C_1$-$C_4$)-alkyl, ($C_3$-$C_8$)-alkenyl, ($C_3$-$C_8$)-alkynyl, CO—($C_1$-$C_8$)-alkyl, CO—($CH_2$)$_o$—O—($C_1$-$C_6$)-alkyl, or CO(C(R61)(R62))$_r$N(R76)(R77), R54' is (C(R58)(R59))$_q$-R60, ($C_1$-$C_4$)-alkoxy-($C_1$-$C_4$)-alkyl, ($C_3$-$C_8$)-alkenyl, or ($C_3$-$C_8$)-alkynyl, or R53' and R54' taken together with the nitrogen atom to which they are bonded form a 6 to 10-membered bi- or spirocyclic nonaromatic ring which optionally comprises 1 to 3 additional heteroatoms selected from the group consisting of oxygen, nitrogen and sulfur, where the heterocyclic ring system is optionally substituted by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl;

R60 is OH, F, O—(C$_1$-C$_6$)-alkyl, N(R74)CO(C$_1$-C$_6$)-alkyl, or 3-12 membered mono-, bi- or spirocyclic non-aromatic ring which optionally comprises one or more heteroatoms from the group consisting of N, O and S, and the 3-12 membered ring is optionally substituted by F, Cl, Br, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, N(R76)(R77) or SO$_2$(C$_1$-C$_6$)-alkyl;

or a pharmaceutically acceptable salt thereof.

19. A compound of formula (I)

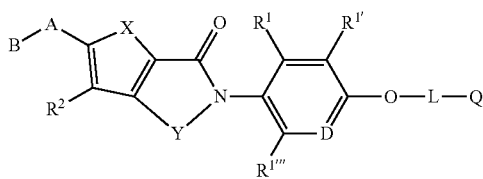

wherein

D is N or C(R1''');

R1, R1', R1'' and R1''' are independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R3)(R4), SO$_2$-CH$_3$, COOH, COO—(C$_1$-C$_6$)-alkyl, CON(R5)(R6), N(R7)CO(R8), N(R9)SO$_2$(R10), CO(R11), or (C(R12)(R13))$_x$-O(R14);

R3, R4, R5, R6, R7 and R9 are independently of one another H or (C$_1$-C$_8$)-alkyl, or R3 and R4, or R5 and R6 independently of one another, taken together with the nitrogen atom to which they are bonded form a 5-6 membered ring which optionally comprises one additional heteroatom selected from the group consisting of NH, N—(C$_1$-C$_6$)-alkyl, oxygen and sulfur;

R8, R10 and R11 are independently of one another H, (C$_1$-C$_8$)-alkyl, or aryl;

R12 and R13 are independently of one another H, or (C$_1$-C$_8$)-alkyl;

R14 is H, (C$_1$-C$_6$)-alkyl, or aryl;

x is 0, 1, 2, 3, 4, 5 or 6;

R2 is H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$—CH$_3$, COOH, COO—(C$_1$-C$_6$)-alkyl, CON(R17)(R18), N(R19)CO(R20), N(R21)SO$_2$(R22), CO(R23), or (C(R24)(R25))$_x$-O(R26);

R15, R16, R17, R18, R19 and R21 are independently of one another H, or (C$_1$-C$_8$)-alkyl, or R15 and R16, or R17 and R18 independently of one another, taken together with the nitrogen atom to which they are bonded form a 5-6 membered ring which optionally comprises one additional heteroatom from the group consisting of NH, N—(C$_1$-C$_6$)-alkyl, oxygen and sulfur;

R20, R22 and R23 are independently of one another H, (C$_1$-C$_8$)-alkyl, or aryl;

R24 and R25 are independently of one another H, or (C$_1$-C$_8$)-alkyl;

R26 is H, (C$_1$-C$_6$)-alkyl, or aryl;

x' is 0, 1, 2, 3, 4, 5 or 6;

Y is C(R27)(R27')C(R28)(R28');

R27, R27', R28, R28'are independently of one another H, or (C$_1$-C$_8$)-alkyl;

X is C(R30)=C(R30');

R30 and R30' are independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$-CH$_3$, COOH, COO—(C$_1$-C$_6$)-alkyl, CON(R17)(R18), N(R19)CO(R20), N(R21)SO$_2$(R22), CO(R23), or (C(R24)(R25))$_{x'}$-O(R26);

A is a bond or a linker having 1 to 8 members, where the members are selected from the group consisting of O, S, SO$_2$, N(R31), CO, C(R32)(R33), C(R34)=C(R34'), cyclopropylene, and C≡C, resulting in a chemically reasonable radical;

R31, R34 and R34' are independently of one another H or (C$_1$-C$_8$)-alkyl;

R32 and R33 are independently of one another H, (C$_1$-C$_6$)-alkyl, OH, or O—(C$_1$-C$_6$)-alkyl;

B is H, N(R35)(R36), hydroxy-(C$_1$-C$_4$)-alkyl, (C$_1$-C$_8$)-alkyl, (C$_1$-C$_4$)-alkoxy-(C$_1$-C$_4$)-alkyl, (C$_2$-C$_8$)-alkenyl, (C$_2$-C$_8$)-alkynyl, or a 3 to 10-membered mono-, bi-, tri- or spirocyclic ring which may comprise 0 to 4 heteroatoms selected from the group consisting of oxygen, nitrogen and sulfur, where the ring system is optionally substituted one or more times by F, Cl, Br, CF$_3$, NO$_2$, CN, (C$_1$-C$_6$)-alkyl, O—(C$_1$-C$_8$)-alkyl, (C$_1$C$_4$)alkoxy-(C$_1$-C$_4$)-alkyl, hydroxy-(C$_1$-C$_4$)-alkyl, oxo, CO(R37), CON(R38)(R39), hydroxy, COO(R40), N(R41)CO(C$_1$-C$_6$)-alkyl, N(R42)(R43), SO$_2$CH$_3$, SCF$_3$ or S—(C$_1$-C$_6$)-alkyl;

R35, R36, R37, R38, R39, R40, R41, R42 and R43 independently of one another H or (C$_1$-C$_8$)-alkyl, or R38 and R39, or R42 and R43 independently of one another taken together with the nitrogen atom to which they are bonded form a 5-6 membered ring which optionally comprises one additional heteroatom selected from the group consisting of NH, N—(C$_1$-C$_6$)-alkyl, oxygen and sulfur;

L is a bond or (C1-C3)-alkylene;

Q is N(R53')(R54'), or a bi-, tri- or spirocyclic saturated or partly unsaturated ring structure having one nitrogen atom and 0-3 additional heteroatoms selected from the group consisting of N, O and S, where the rings of the structure may be spiro-linked, fused or bridged, and where the ring system is optionally substituted one or more times by F, OH, CF$_3$, CN, OCF$_3$, oxo, O—(C$_1$-C$_8$)-alkyl, (C$_1$-C$_4$)-alkoxy-(C$_1$-C$_4$)-alkyl, (C$_1$-C$_6$)- alkyl, $(C_2-C_6)$-alkenyl, $(C_2-C_6)$-alkynyl, CO(R44), $(C(R45)(R46))_o$-R47, or $CO(C(R45)(R46))_p$-R48;

R44 is H, $(C_1-C_8)$-alkyl;

R45 and R46 are independently of one another H, $(C_1-C_8)$-alkyl, OH, $(C_3-C_8)$-cycloalkyl, or $(C_1-C_4)$-alkoxy-$(C_1-C_4)$-alkyl;

o and p are independently of one another 0, 1, 2, 3, 4, 5 or 6;

R47 and R48 are independently of one another OH, F, O—$(C_1-C_8)$-alkyl, CON(R49)(R50), N(R51)CO(R52), N(R53)(R54), $CO_2$(R55), $SO_2$Me, CN, or a 3-10 membered ring system having 0 to 3 heteroatoms selected from the group consisting of N, O and S, which is optionally substituted one or more times by F, Cl, Br, $CF_3$, $(C_1-C_8)$-alkyl, O—$(C_1-C_8)$-alkyl, $(C_1-C_4)$-alkoxy-$(C_1-C_4)$-alkyl, CO(R56), oxo, or OH;

R49, R50, R51, R52, R55 and R56 are independently of one another H or $(C_1-C_8)$-alkyl, or R49 and R50 taken together with the nitrogen atom to which they are bonded form a 5-6 membered ring which optionally comprises one additional heteroatom selected from the group consisting of NH, N—$(C_1-C)$-alkyl, oxygen and sulfur;

R53, R54, R53' and R54' are independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R57), $(C(R58)(R59))_q$-R60, $CO(C(R61)(R62))_r$-R63, or CO—$(CH_2)_{o'}$—O—$(C_1-C_6)$-alkyl, or R53 and R54, or R53' and R54' taken together with the nitrogen atom to which they are bonded form a 4 to 10-membered mono-, bi- or spirocyclic ring which optionally comprises 1 to 3 additional heteroatoms selected from the group consisting of N, O and S, and which is optionally substituted one or more times by F, Cl, Br, $CF_3$, O—$(C_1-C_8)$-alkyl, $(C_1-C_6)$-alkyl, CO(R64), oxo, OH, $(C_1-C_4)$-alkoxy-$(C_1-C_4)$-alkyl, hydroxy-$(C_1-C_4)$-alkyl, CON(R65)(R66), N(R67)CO(R68), N(R69)(R70), $CO_2$(R71), or $SO_2(C_1-C_6)$-alkyl;

o' is 0, 1, 2, 3, 4, 5 or 6;

R58 and R59 are independently of one another H, $(C_1-C_6)$-alkyl, or OH;

R57, R61, R62, R64, R65, R66, R67, R68, R69, R70 and R71 independently of one another H, or $(C_1-C_6)$-alkyl, or

R69 and R70 taken together with the nitrogen atom to which they are bonded form a 5-6 membered ring which optionally comprises one additional heteroatom selected from the group of NH, N—$(C_1-C_6)$-alkyl, oxygen and sulfur;

q and r are independently of one another 0, 1, 2, 3, 4, 5 or 6;

R60 and R63 are independently of one another OH, F, O—$(C_1-C_6)$-alkyl, COO(R78), N(R74)CO$(C_1-C_6)$-alkyl, N(R76)(R77), CON(R72)(R73), $SO_2(C_1-C_6)$-alkyl, or a 3-12 membered mono-, bi- or spirocyclic ring which optionally comprises one or more heteroatoms from the group of N, O and S, and the 3-12 membered ring is optionally substituted by F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, N(R76)(R77), COO(R78), $SO_2(C_1-C_6)$-alkyl or COOH; and R72, R73, R74, R76, R77 and R78 are independently of one another H, or $(C_1-C_8)$-alkyl, or R72 and R73, or R76 and R77 independently of one another taken together with the nitrogen atom to which they are bonded form a 5-6 membered ring which optionally comprises one additional heteroatom from the group of NH, N—$(C_1-C_6)$-alkyl, oxygen and sulfur;

provided that when L is $(C_1-C_3)$-alkylene, then B is not an aromatic radical, a cycloalkyl radical, an alk-2-en-1-yl radical or a cycloalk-2-en-1-yl radical, and A does not contain the moiety C(R34')C(R34');

or a pharmaceutically acceptable salt thereof.

20. The compound according to claim 1, wherein

Y is C(R29)=C(R29'); and

R29 and R29' are H;

or a pharmaceutically acceptable salt thereof.

21. The compound according to claim 1, wherein

R30 and R30' are independently from another H, F, Cl, O—$(C_1-C_6)$-Alkyl, or $(C_1-C_6)$-Alkyl;

or a pharmaceutically acceptable salt thereof.

22. The compound according to claim 1, wherein

R27, R27', R28, R28', R29, R29', R30 and R30' are H;

or a pharmaceutically acceptable salt thereof.

23. The compound according to claim 1, wherein

R2 is H;

or a pharmaceutically acceptable salt thereof

24. The compound according to claim 1, which is a compound of formula (Ia)

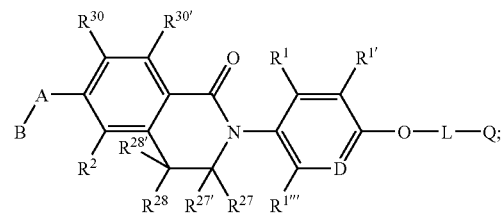

(Ia)

or a pharmaceutically acceptable salt thereof.

25. A compound of formula (I)

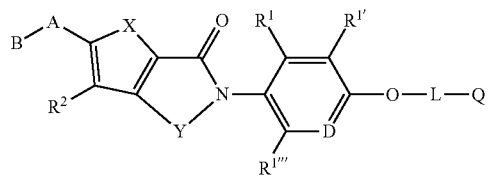

(I)

wherein

D is N or C(R1");

R1, R1', R1" and R1''' are independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R3)(R4), $SO_2$-$CH_3$, COOH, COO—$(C_1-C_6)$-alkyl, CON(R5)(R6), N(R7)CO(R8), N(R9)$SO_2$(R10), CO(R11), or $(C(R12)(R13))_x$-O(R14);

R3, R4, R5, R6, R7 and R9 are independently of one another H or $(C_1-C_8)$-alkyl, or R3 and R4, or R5 and R6 independently of one another, taken together with the nitrogen atom to which the are bonded form a 5-6 membered ring which optionally comprises one additional heteroatom selected from the group consisting of NH, N—$(C_1-C_6)$-alkyl, oxygen and sulfur;

R8, R10 and R11 are independently of one another H, $(C_1-C_8)$-alkyl, or aryl;

R12 and R13 are independently of one another H, or $(C_1-C_8)$-alkyl;

R14 is H, $(C_1-C_6)$-alkyl, or aryl;

x is 0, 1, 2, 3, 4, 5 or 6;

R2 is H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), or $(C(R24)(R25))_{x'}$-O(R26);

R15, R16, R17, R18, R19 and R21 are independently of one another H, or $(C_1-C_8)$-alkyl, or R15 and R16, or R17 and R18 independently of one another, taken together with the nitrogen atom to which they are bonded form a 5-6 membered ring which optionally comprises one additional heteroatom from the group consisting of NH, N—$(C_1-C_6)$-alkyl, oxygen and sulfur;

R20, R22 and R23 are independently of one another H, $(C_1-C_8)$-alkyl, or aryl;

R24 and R25 are independently of one another H, or $(C_1-C_8)$-alkyl;

R26 is H, $(C_1-C_6)$-alkyl, or aryl;

x' is 0, 1, 2, 3, 4, 5 or 6;

Y is C(R27)(R27')C(R28)(R28'), or C(R29)=C(R29');

R27, R27', R28, R28', R29 and R29' are independently of one another H, or $(C_1-C_8)$-alkyl;

X is C(R30)=C(R30');

R30 and R30' are independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), or $(C(R24)(R25))_{x'}$-O(R26);

B-A is

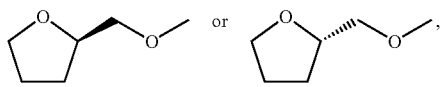

wherein the tetrahydrofuranyl ring is optionally substituted once by methyl or OH;

L is a bond or (C1-C3)-alkylene;

Q is N(R53')(R54'), or a bi-, tri- or spirocyclic saturated or partly unsaturated ring structure having one nitrogen atom and 0-3 additional heteroatoms selected from the group consisting of N, O and S, where the rings of the structure may be spiro-linked, fused or bridged, and where the ring system is optionally substituted one or more times by F, OH, $CF_3$, CN, $OCF_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R44)(C(R45) R46))$_o$-R47 or CO(C(R45)(R46))$_p$-R48;

R44 is H, $(C_1-C_8)$-alkyl;

R45 and R46 are independently of one another H, $(C_1-C_8)$-alkyl, OH, $(C_3-C_8)$-cycloalkyl, or $(C_1-C_4)$-alkoxy-$(C_1-C_4)$-alkyl;

o and p are independently of one another 0, 1, 2, 3, 4, 5 or 6;

R47 and R48 are independently of one another OH, F, O—$(C_1-C_8)$-alkyl, CON(R49)(R50), N(R51)CO(R52), N(R53)(R54), $CO_2$(R55), $SO_2$Me, CN, or a 3-10 membered ring system having 0 to 3 heteroatoms selected from the group consisting of N, O and S, which is optionally substituted one or more times by F, Cl, Br, $CF_3$, $(C_1-C_8)$-alkyl, O—$(C_1-C_8)$-alkyl, $(C_1-C_4)$-alkoxy-$(C_1-C_4)$-alkyl, CO(R56), oxo, or OH;

R49, R50, R51, R52, R55 and R56 are independently of one another H or $(C_1-C_8)$-alkyl, or R49 and R50 taken together with the nitrogen atom to which they are bonded form a 5-6 membered ring which optionally comprises one additional heteroatom selected from the group consisting of NH, N—$(C_1-C_6)$-alkyl, oxygen and sulfur;

R53, R54, R53' and R54' are independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R57), (C(R58)(R59))$_q$-R60, CO(C(R61)(R62))$_r$-R63, or CO—(CH$_2$)$_{o'}$—O—$(C_1-C_6)$-alkyl, or R53 and R54, or R53' and R54' taken together with the nitrogen atom to which they are bonded form a 4 to 10-membered mono-, bi- or spirocyclic ring which optionally comprises 1 to 3 additional heteroatoms selected from the group consisting of N, O and S, and which is optionally substituted one or more times by F, Cl, Br, $CF_3$, O—$(C_1-C_8)$-alkyl, $(C_1-C_6)$-alkyl, CO(R64), oxo, OH, $(C_1-C_4)$-alkoxy-$(C_1-C_4)$-alkyl, hydroxy-$(C_1-C_4)$-alkyl, CON(R65)(R66), N(R67)CO(R68), N(R69)(R70), $CO_2$(R71), or $SO_2(C_1-C_6)$-alkyl;

o' is 0, 1, 2, 3, 4, 5 or 6;

R58 and R59 are independently of one another H, $(C_1-C_6)$-alkyl, or OH;

R57, R61, R62, R64, R65, R66, R67, R68, R69, R70 and R71 independently of one another H, or $(C_1-C_6)$-alkyl, or R69 and R70 taken together with the nitrogen atom to which they are bonded form a 5-6 membered ring which optionally comprises one additional heteroatom selected from the group of NH, N—$(C_1-C_6)$-alkyl, oxygen and sulfur;

q and r are independently of one another 0, 1, 2, 3, 4, 5 or 6;

R60 and R63 are independently of one another OH, F, O—$(C_1-C_6)$-alkyl, CN, COO(R78), N(R74)CO(C$_1$-C$_6$)-alkyl, N(R76)(R77), CON(R72)(R73), $SO_2(C_1-C_6)$-alkyl, or a 3-12 membered mono-, bi- or spirocyclic ring which optionally comprises one or more heteroatoms from the group of N, O and S, and the 3-12 membered ring is optionally substituted by F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, N(R76)(R77), COO(R78), $SO_2$($C_1$-$C_6$)-alkyl or COOH; and R72, R73, R74, R76, R77 and R78 are independently of one another H, or ($C_1$-$C_8$)-alkyl, or R72 and R73, or R76 and R77 independently of one another taken together with the nitrogen atom to which they are bonded form a 5-6 membered ring which optionally comprises one additional heteroatom from the group of NH, N—($C_1$-$C_6$)-alkyl, oxygen and sulfur;

provided that when L is ($C_1$-$C_3$)-alkylene, then B is not an aromatic radical, a cycloalkyl radical, an alk-2-en-1-yl radical or a cycloalk-2-en-1-yl radical, and A does not contain the moiety C(R34')C(R34');

or a pharmaceutically acceptable salt thereof.

26. The compound according to claim 1, wherein B-A is

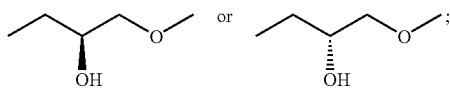

or a pharmaceutically acceptable salt thereof.

27. The compound according to claim 1, wherein
A is $CH_2$—O, $CH_2CH_2$O, $COCH_2$O, O—CO—$CH_2$—O, $CH_2CH_2CH_2$O, or $COCH_2CH_2$O;
or a pharmaceutically acceptable salt thereof.

28. The compound according to claim 1, wherein
B is ($C_1$-$C_4$)-alkoxy-($C_1$-$C_4$)-alkyl, or a monocyclic ring selected from the group consisting of

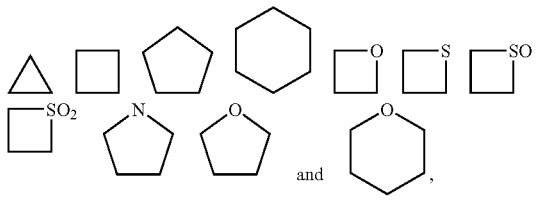

where the monocyclic ring is optionally substituted once or twice by F, $CF_3$, CN, methyl, ethyl, methoxy, oxo, hydroxy, or $SO_2$-methyl;
or a pharmaceutically acceptable salt thereof.

29. A compound of formula (Ib)

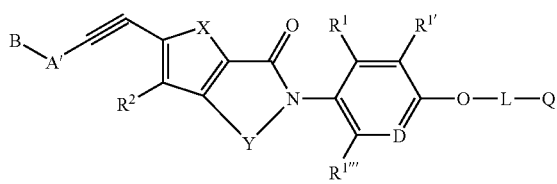

(Ib)

wherein:
D is N or C(R1");
R1, R1', R1" and R1''' are independently of one another H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R3)(R4), $SO_2$—$CH_3$, COOH, COO—($C_1$-$C_6$)-alkyl, CON(R5)(R6), N(R7)CO(R8), N(R9)$SO_2$(R10), CO(R11), or $(C(R12)(R13))_x$-O(R14);

R3, R4, R5, R6, R7 and R9 are independently of one another H or ($C_1$-$C_8$)-alkyl, or R3 and R4, or R5 and R6 independently of one another, taken together with the nitrogen atom to which they are bonded form a 5-6 membered ring which optionally comprises one additional heteroatom selected from the group consisting of NH, N—($C_1$-$C_6$)-alkyl, oxygen and sulfur;

R8, R10 and R11 are independently of one another H, ($C_1$-$C_8$)-alkyl, or aryl;

R12 and R13 are independently of one another H, or ($C_1$-$C_8$)-alkyl;

R14 is H, ($C_1$-$C_6$)-alkyl, or aryl;

x is 0, 1, 2, 3, 4, 5 or 6;

R2 is H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R15)(R16), $SO_2$—$CH_3$, COOH, COO—($C_1$-$C_6$)-alkyl, CON(R17)(R18), N(R19)CO(R20), N(R21)$SO_2$(R22), CO(R23), or $(C(R24)(R25))_x$-O(R26);

R15, R16, R17, R18, R19 and R21 are independently of one another H, or ($C_1$-$C_8$)-alkyl, or R15 and R16, or R17 and R18 independently of one another, taken together with the nitrogen atom to which they are bonded form a 5-6 membered ring which optionally comprises one additional heteroatom from the group consisting of NH, N—($C_1$-$C_6$)-alkyl, oxygen and sulfur;

R20, R22 and R23 are independently of one another H, ($C_1$-$C_8$)-alkyl, or aryl;

R24 and R25 are independently of one another H, or ($C_1$-$C_8$)-alkyl;

R26 is H, ($C_1$-$C_6$)-alkyl, or aryl;

x' is 0, 1, 2, 3, 4, 5 or 6;

Y is C(R27)(R27')C(R28)(R28'), or C(R29)=C(R29');

R27, R27', R28, R28', R29 and R29' are independently of one another H, or ($C_1$-$C_8$)-alkyl;

X is C(R30)=C(R30');

R30 and R30' are independently of one another H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R15)(R16), $SO_2$—$CH_3$, COOH, COO—($C_1$-$C_6$)-alkyl, CON(R17)(R18), N(R19)CO(R20), NCR21)$SO_2$(R22), CO(R23), or $(C(R24)(R25))_x$-O(R26);

A' is a bond or a linker having 1 to 5 members, where the members are selected from the group consisting of O, N(R31), CO, and (C(R32)R(R33)), resulting in a chemically reasonable radical;

R31 is H or ($C_1$-$C_8$)-alkyl;

R32 and R33 are independently of one another H, ($C_1$-$C_6$)-alkyl, OH, or O—($C_1$-$C_6$)-alkyl;

B is H, N(R35)(R36), hydroxy-($C_1$-$C_4$)-alkyl, ($C_1$-$C_8$)-alkyl, ($C_1$-$C_4$)-alkoxy-($C_1$-$C_4$)-alkyl, ($C_2$-$C_8$)-alkenyl, ($C_2$-$C_8$)-alkynyl, or a 3 to 10-membered mono-, bi-, trior spirocyclic ring which may comprise 0 to 4 heteroatoms selected from the group consisting of oxygen, nitrogen and sulfur, where the ring system is optionally substituted one or more times by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO($C_1$-$C_6$)-alkyl, N(R42)(R43), $SO_2CH_3$, $SCF_3$ or S—$(C_1$-$C_6)$-alkyl;

R35, R36, R37, R38, R39, R40, R41, R42 and R43 independently of one another H or $(C_1-C_8)$-alkyl, or R38 and R39, or R42 and R43 independently of one another taken together with the nitrogen atom to which they are bonded form a 5-6 membered ring which optionally comprises one additional heteroatom selected from the group consisting of NH, N—$(C_1-C_6)$-alkyl, oxygen and sulfur;

L is a bond or (C1-C3)-alkylene;

Q is N(R53')(R54'), or a bi-, tri- or spirocyclic saturated or partly unsaturated ring structure having one nitrogen atom and 0-3 additional heteroatoms selected from the group consisting of N, O and S, where the rings of the structure may be spiro-linked, fused or bridged, and where the ring system is optionally substituted one or more times by F, OH, $CF_3$, CN, $OCF_3$, oxo, O—$(C_1$-$C_8)$-alkyl, $(C_1-C_4)$-alkoxy-$(C_1-C_4)$-alkyl, $(C_1-C_4)$-alkyl, $(C_2-C_6)$-alkenyl, $(C_2-C_6)$-alkynyl, (CO(R44)), $(C(R45)(R46))_o$-R47, or $CO(C(R45)(R46))_p$-R48;

R44 is H, $(C_1-C_8)$-alkyl;

R45 and R46 are independently of one another H, $(C_1-C_8)$-alkyl, OH, $(C_3-C_8)$-cycloalkyl, or $(C_1-C_4)$-alkoxy-$(C_1$-$C_4)$-alkyl;

o and p are independently of one another 0, 1, 2, 3, 4, 5 or 6;

R47 and R48 are independently of one another OH, F, O—$(C_1-C_8)$-alkyl, CON(R49)(R50), N(R51)CO(R52), N(R53)(R54), $CO_2$(R55), $SO_2Me$, CN, or a 3-10 membered ring system having 0 to 3 heteroatoms selected from the group consisting of N, O and S, which is optionally substituted one or more times by F, Cl, Br, $CF_3$, $(C_1-C_8)$-alkyl, O—$(C_1-C_8)$-alkyl, $(C_1-C_4)$-alkoxy-$(C_1$-$C_4)$-alkyl, CO(R56), oxo, or OH;

R49, R50, R51, R52, R55 and R56 are independently of one another H or $(C_1-C_8)$-alkyl, or R49 and R50 taken together with the nitrogen atom to which they are bonded form a 5-6 membered ring which optionally comprises one additional heteroatom selected from the group consisting of NH, N—$(C_1-C_6)$-alkyl, oxygen and sulfur;

R53, R54, R53' and R54' are independently of one another H, $(C_1-C_8)$-alkyl, $(C_1-C_4)$-alkoxy-$(C_1-C_4)$-alkyl, $(C_3$-$C_8)$-alkenyl, $(C_3-C_8)$-alkynyl, CO(R57), (C(R58)(R59))$_q$-R60, $CO(C(R61)(R62))_r$-R63, or CO—$(CH_2)_{o'}$—O—$(C_1-C_6)$-alkyl, or R53 and R54, or R53' and R54' taken together with the nitrogen atom to which they are bonded form a 4 to 10-membered mono-, bi- or spirocyclic ring optionally comprises 1 to 3 additional heteroatoms selected from the group consisting of N, O and S, and which is optionally substituted one or more times by F, Cl, Br, $CF_3$, O—$(C_1-C_8)$-alkyl, $(C_1-C_6)$-alkyl, CO(R64), oxo, OH, $(C_1-C_4)$-alkoxy-$(C_1-C_4)$-alkyl, hydroxy-$(C_1-C_4)$-alkyl, CON(R65)(R66), N(R67)CO (R68), N(R69)(R70), $CO_2$(R71), or $SO_2(C_1-C_6)$-alkyl;

o' is 0, 1, 2, 3, 4, 5 or 6;

R58 and R59 are independently of one another H, $(C_1-C_6)$-alkyl, or OH;

R57, R61, R62, R64, R65, R66, R67, R68, R69, R70 and R71 independently of one another H, or $(C_1-C_6)$-alkyl, or R69 and R70 taken together with the nitrogen atom to which they are bonded form a 5-6 membered ring which optionally comprises one additional heteroatom selected from the group of NH, N—$(C_1-C_6)$-alkyl, oxygen and sulfur;

q and r are independently of one another 0, 1, 2, 3, 4, 5 or 6;

R60 and R63 are independently of one another OH, F, O—$(C_1-C_6)$-alkyl, CN, COO(R78), N(R74)CO($C_1$-$C_6)$-alkyl, N(R76)(R77), CON(R72)(R73), $SO_2(C_1$-$C_6)$-alkyl, or a 3-12 membered mono-, bi- or spirocyclic ring which optionally comprises one or more heteroatoms from the group of N, O and S, and the 3-12 membered ring is optionally substituted by F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, N(R76)(R77), COO(R78), $SO_2$ $(C_1-C_6)$-alkyl or COOH; and R72, R73, R74, R76, R77 and R78 are independently of one another H, or $(C_1-C_8)$-alkyl, or R72 and R73, or R76 and R77 independently of one another taken together with the nitrogen atom to which they are bonded form a 5-6 membered ring which optionally comprises one additional heteroatom from the group of NH, N—$(C_1-C_6)$-alkyl, oxygen and sulfur;

provided that when L is $(C_1-C_3)$-alkylene, then B is not an aromatic radical, a cycloalkyl radical, an alk-2-en-1-yl radical or a cycloalk-2-en-1-yl radical, and A does not contain the moiety C(R34')C(R34');

or a pharmaceutically acceptable salt thereof.

30. The compound according to claim 1, wherein

A is a linker having 2 to 4 members, where the members are selected from the group consisting of O, CO, and C(R32)(R33) resulting in a chemically reasonable radical, provided that the linker has no CO—O or O—CO groups;

or a pharmaceutically acceptable salt thereof.

31. A pharmaceutical composition comprising the compound according to claim 1 or a pharmaceutically acceptable salt thereof, in combination with at least one pharmaceutically acceptable carrier.

32. A pharmaceutical composition comprising the compound according to claim 1 or a pharmaceutically acceptable salt thereof, and at least one additional active ingredient which has beneficial effect on metabolic disturbance or a disorder associated therewith.

33. A pharmaceutical composition comprising the compound according to claim 1 or a pharmaceutically acceptable salt thereof, and at least one antidiabetic active ingredient.

34. A pharmaceutical composition comprising the compound according to claim 1 or a pharmaceutically acceptable salt thereof, and at least one lipid modulator.

35. A pharmaceutical composition comprising the compound according to claim 1 or a pharmaceutically acceptable salt thereof, and at least one antiobesity active ingredient.

36. The compound according to claim 1, wherein of formula (I)

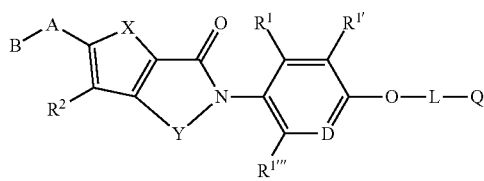

D is N or C(R1'');

R1, R1', R1'' and R1''' are independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)alkynyl, (C$_0$-C$_8$)-alkylene-aryl, O—(C$_0$-C$_8$)-alkylene-aryl, S-aryl, N(R3)(R4), SO$_2$—CH$_3$, COOH, COO—(C$_1$-C$_6$)-alkyl, CON(R5)(R6), N(R7)CO(R8), N(R9)SO$_2$(R10), CO(R11), or (C(R12)(R13))$_x$-O(R14);

R3, R4, R5, R6, R7 and R9 are independently of one another H or (C$_1$-C$_8$)-alkyl, or R3 and R4, or R5 and R6 independently of one another, taken together with the nitrogen atom to which they are bonded form a 5-6 membered ring which optionally comprises one additional heteroatom selected from the group consisting of NH, N—(C$_1$-C$_6$)-alkyl, oxygen and sulfur;

R8, R10 and R11 are independently of one another H, (C$_1$-C$_8$-alkyl, or aryl;

R12 and R13 are independently of one another H, or (C$_1$-C$_8$)-alkyl;

R14 is H, (C$_1$-C$_6$)-alkyl, or aryl;

x is 0, 1, 2, 3, 4, 5 or 6;

R2 is H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$—CH$_3$, COOH, COO—(C$_1$-C$_6$)-alkyl, CON(R17)(R18), N(R19)CO(R20), N(R21)SO$_2$(R22), CO(R23), or (C(R24)(R25))$_{x'}$-O(R26);

R15, R16, R17, R18, R19 and R21 are independently of one another H, or (C$_1$-C$_8$)-alkyl, or R15 and R16, or R17 and R18 independently of one another, taken together with the nitrogen atom to which they are bonded form a 5-6 membered ring which optionally comprises one additional heteroatom from the group consisting of NH, N—(C$_1$-C$_6$)-alkyl, oxygen and sulfur;

R20, R22 and R23 are independently of one another H, (C$_1$-C$_8$)-alkyl, or aryl;

R24 and R25 are independently of one another H, or (C$_1$-C$_8$)-alkyl;

R26 is H, (C$_1$-C$_6$)-alkyl, or aryl;

x' is 0, 1, 2, 3, 4, 5 or 6;

Y is C(R29)=C(R29');

R27, R27', R28, R28', R29 and R29' are independently of one another H, or (C$_1$-C$_8$)-alkyl;

X is C(R30)=C(R30');

R30 and R30' are independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$—CH$_3$, COOH, COO—(C$_1$-C$_6$)-alkyl, CON(R17)(R18), N(R19)CO(R20), N(R21)SO$_2$(R22), CO(R23), or (C(R24)(R25))$_{x'}$-O(R26);

A is C(R34)=C(R34');

R34 and R34' are independently of one another H or (C$_1$-C$_8$)-alkyl;

B is a 3 to 10-membered mono-, bi-, tri- or spirocyclic non-aromatic ring which may comprise 0 to 4 heteroatoms selected from the group consisting of oxygen, nitrogen and sulfur, where the ring system is optionally substituted one or more times by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), CON(R38)(R39), hydroxy, COO(R40), N(R41)CO(C$_1$-C$_6$)-alkyl, N(R42)(R43), SO$_2$CH$_3$, SCF$_3$ or S—(C$_1$-C$_6$)-alkyl;

R37, R38, R39, R40, R41, R42 and R43 independently of one another H or (C$_1$-C$_8$)-alkyl, or R38 and R39, or R42 and R43 independently of one another taken together with the nitrogen atom to which they are bonded form a 5-6 membered ring which optionally comprises one additional heteroatom selected from the group consisting of NH, N—(C$_1$-C$_6$)-alkyl, oxygen and sulfur;

L is a bond or (C1-C3)-alkylene;

Q is N(R53')(R54'), or a bi-, tri- or spirocyclic saturated or partly unsaturated ring structure having one nitrogen atom and 0-3 additional heteroatoms selected from the group consisting of N, O and S, where the rings of the structure may be spiro-linked, fused or bridged, and where the ring system is optionally substituted one or more times by F, OH, CF$_3$, CN, OCF$_3$, oxo, O—(C$_1$-C$_8$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, CO(R44), (C(R45)(R46))$_o$-R47, or CO(C(R45)(R46))$_p$-R48;

R44 is H, (C$_1$-C$_8$)-alkyl;

R45 and R46 are independently of one another H, (C$_1$-C$_8$)-alkyl, OH, (C$_3$-C$_8$)-cycloalkyl, or (C$_1$-C$_4$)-alkoxy-(C$_1$-C$_4$)-alkyl;

o and p are independently of one another 0, 1, 2, 3, 4, 5 or 6;

R47 and R48 are independently of one another OH, F, O—(C$_1$-C$_8$)-alkyl, CON(R49)(R50), N(R51)CO(R52), N(R53)(R54), CO$_2$(R55), SO$_2$Me, CN, or a 3-10 membered ring system having 0 to 3 heteroatoms selected from the group consisting of N, O and S, which is optionally substituted one or more times by F, Cl, Br, CF$_3$, (C$_1$-C$_8$)-alkyl, O—(C$_1$-C$_8$)-alkyl, (C$_1$-C$_4$)-alkoxy-(C$_1$-C$_4$)-alkyl, CO(R56), oxo, or OH;

R49, R50, R51, R52, R55 and R56 are independently of one another H or (C$_1$-C$_8$)-alkyl, or R49 and R50 taken together with the nitrogen atom to which they are bonded form a 5-6 membered ring which optionally comprises one additional heteroatom selected from the group consisting of NH, N—(C$_1$-C$_6$)-alkyl, oxygen and sulfur;

R53, R54, R53' and R54' are independently of one another H, (C$_1$-C$_8$)-alkyl, (C$_1$-C$_4$)-alkoxy-(C$_1$-C$_4$)-alkyl, (C$_3$-

$C_8$)-alkenyl, ($C_3$-$C_8$)-alkynyl, CO(R57), (C(R58)(R59))$_q$-R60, CO(C(R61)(R62))$_r$-R63, or CO—($CH_2$)$_{o'}$—O—($C_1$-$C_6$)-alkyl, or R53 and R54, or R53' and R54' taken together with the nitrogen atom to which they are bonded form a 4 to 10-membered mono-, bi- or spirocyclic ring which optionally comprises 1 to 3 additional heteroatoms selected from the group consisting of N, O and S, and which is optionally substituted one or more times by F, Cl, Br, $CF_3$, O—($C_1$-$C_8$)alkyl, ($C_1$-$C_6$)-alkyl, CO(R64), oxo, OH, ($C_1$-$C_4$)-alkoxy-($C_1$-$C_4$)-alkyl, hydroxy-($C_1$-$C_4$)-alkyl, CON(R65)(R66), N(R67)CO(R68), N(R69)(R70), $CO_2$(R71), or $SO_2$($C_1$-$C_6$)-alkyl;

o' is 0, 1, 2, 3, 4, 5 or 6;

R58 and R59 are independently of one another H, ($C_1$-$C_6$)-alkyl, or OH;

R57, R61, R62, R64, R65, R66, R67, R68, R69, R70 and R71 independently of one another H, or ($C_1$-$C_6$)-alkyl, or

R69 and R70 taken together with the nitrogen atom to which they are bonded form a 5-6 membered ring which optionally comprises one additional heteroatom selected from the group of NH, N—($C_1$-$C_6$)-alkyl, oxygen and sulfur;

q and r are independently of one another 0, 1, 2, 3, 4, 5 or 6;

R60 and R63 are independently of one another OH, F, O—($C_1$-$C_6$)-alkyl, CN, COO(R78), N(R74)CO($C_1$-$C_6$)-alkyl, N(R76)(R77), CON(R72)(R73), $SO_2$($C_1$-$C_6$)-alkyl, or a 3-12 membered mono-, bi- or spirocyclic ring which optionally comprises one or more heteroatoms from the group of N, O and S, and the 3-12 membered ring is optionally substituted by F, Cl, Br, OH, $CF_3$, $NO_2$, CN, $OCF_3$, oxo, O—($C_1$-$C_6$)-alkyl, ($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, N(R76)(R77), COO(R78), $SO_2$($C_1$-$C_6$)-alkyl or COOH; and R72, R73, R74, R76, R77 and R78 are independently of one another H, or ($C_1$-$C_8$)-alkyl, or R72 and R73, or R76 and R77 independently of one another taken together with the nitrogen atom to which they are bonded form a 5-6 membered ring which optionally comprises one additional heteroatom from the group of NH, N—($C_1$-$C_6$)-alkyl, oxygen and sulfur;

provided that when L is ($C_1$-$C_3$)-alkylene, then B is not an aromatic radical, a cycloalkyl radical, an alk-2-en-1-yl radical or a cycloalk-2-en-1-yl radical, and A does not contain the moiety C(R34')C(R34');

or a pharmaceutically acceptable salt thereof.

* * * * *